United States Patent [19]
Chang et al.

[11] Patent Number: 5,994,306
[45] Date of Patent: *Nov. 30, 1999

[54] FINE-TUNED PROTEGRINS

[75] Inventors: Conway C. Chang, San Francisco; Chee Liang Gu, Saratoga; Jie Chen, Belmont; Deborah A. Steinberg, Saratoga; Robert I. Lehrer, Santa Monica; Sylvia S.L. Harwig, deceased, late of Woodland Hills, all of Calif., by John Harwig, executor

[73] Assignee: IntraBiotics Pharmaceuticals, Inc., Mountain View, Calif.

[*] Notice: This patent is subject to a terminal disclaimer.

[21] Appl. No.: 08/752,852

[22] Filed: Nov. 21, 1996

Related U.S. Application Data

[63] Continuation-in-part of application No. 08/690,921, Aug. 1, 1996, abandoned, which is a continuation-in-part of application No. 08/649,811, May 17, 1996, abandoned, which is a continuation-in-part of application No. 08/562,346, Nov. 22, 1995, abandoned, which is a continuation-in-part of application No. 08/499,523, Jul. 7, 1995, Pat. No. 5,804,558, which is a continuation-in-part of application No. 08/451,832, May 26, 1995, abandoned, which is a continuation-in-part of application No. PCT/US94/08305, Jul. 20, 1994, and application No. 08/243,879, May 17, 1994, Pat. No. 5,708,145, which is a continuation-in-part of application No. 08/182,483, Jan. 13, 1994, Pat. No. 5,693,486, which is a continuation-in-part of application No. 08/095,769, Jul. 26, 1993, Pat. No. 5,464,823, which is a continuation-in-part of application No. 08/093,926, Jul. 20, 1993, abandoned.

[51] Int. Cl.⁶ .......................... A61K 38/04; A01N 25/00; C12N 15/12; C12N 15/13
[52] U.S. Cl. .............................. 514/13; 514/12; 530/326; 424/405; 536/23.5; 435/252.3; 435/320.1
[58] Field of Search ...................... 514/12, 13; 435/64.1, 435/252.3, 320.1; 530/326; 536/23.5; 424/405

[56] References Cited

U.S. PATENT DOCUMENTS

| | | | |
|---|---|---|---|
| 4,543,252 | 9/1985 | Lehrer et al. | 514/12 |
| 4,652,639 | 3/1987 | Stabinsky | 435/91.52 |
| 4,659,692 | 4/1987 | Lehrer et al. | 514/12 |
| 4,705,777 | 11/1987 | Lehrer et al. | 514/12 |
| 5,087,569 | 2/1992 | Gabay et al. | 435/212 |
| 5,102,870 | 4/1992 | Florine et al. | 514/12 |
| 5,126,257 | 6/1992 | Gabay et al. | 435/212 |
| 5,171,739 | 12/1992 | Scott et al. | 514/12 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,338,724 | 8/1994 | Gabay et al. | 514/12 |

(List continued on next page.)

FOREIGN PATENT DOCUMENTS

| | | |
|---|---|---|
| 272489 | 6/1988 | European Pat. Off. . |
| 545730 | 6/1993 | European Pat. Off. . |
| 89/11291 | 11/1989 | WIPO . |
| 93/01723 | 2/1993 | WIPO . |
| 93/19087 | 9/1993 | WIPO . |
| 93/24139 | 12/1993 | WIPO . |
| WO 94/02589 | 2/1994 | WIPO . |
| 94/21672 | 9/1994 | WIPO . |
| WO 94/28921 | 12/1994 | WIPO . |
| 95/03325 | 2/1995 | WIPO . |
| 95/10534 | 4/1995 | WIPO . |
| WO 95/26747 | 10/1995 | WIPO . |
| WO 96/04373 | 12/1996 | WIPO . |

OTHER PUBLICATIONS

Simmaco, M., et al., The Journal of Biological Chemistry, vol. 269, "Antimicrobial peptides from skin secretions of Rana esculenta", pp. 11956–11961, 1994.

(List continued on next page.)

*Primary Examiner*—Ponnathapura Achutamurthy
*Assistant Examiner*—William W. Moore
*Attorney, Agent, or Firm*—Pennie & Edmonds LLP

[57] ABSTRACT

The invention is directed to antimicrobial peptides related to naturally-occurring protegrin peptides, and methods of using the peptides in a variety of contexts, including the treatment or prevention of infections.

42 Claims, 9 Drawing Sheets

U.S. PATENT DOCUMENTS

| | | | |
|---|---|---|---|
| 5,432,270 | 7/1995 | Zasloff et al. | 536/23.5 |
| 5,447,914 | 9/1995 | Travis et al. | 514/16 |
| 5,458,874 | 10/1995 | Pereira et al. | 424/85.1 |
| 5,459,235 | 10/1995 | Selsted et al. | 530/300 |
| 5,464,823 | 11/1995 | Lehrer et al. | 514/13 |
| 5,484,885 | 1/1996 | Pereira et al. | 530/326 |
| 5,607,916 | 3/1997 | Periera et al. | 514/12 |
| 5,693,486 | 12/1997 | Lehrer et al. | 435/69.1 |
| 5,708,145 | 1/1998 | Lehrer et al. | 530/387.1 |

OTHER PUBLICATIONS

Bateman et al. 1992, "The levels and biologic action of the human neutrophil granule peptide HP–1 in lung tumors," *Peptides* 13:133–139.

Bilgrami, S. et al., 1992, "Capnocytophaga Bacteremia in Patient with Hodgkin's Disease following Bone Marrow Transplantation: Case Report and Review," *Clinical Infectious Diseases* 14:1045–1049.

Broekaert et al., 1992, *Biochemistry* 31:4308–4314.

Cornelissen et al., 1993, *Plant Physiol.* 101:709–712.

Diamond et al., 1991, *Proc. Natl. Acad. Sci. U.S.A.* 88:3952–3956.

Donnelley, J.P. et al., 1993, "Failure of Clindamycin to Influence the Course of Severe Oromucostis Associated with Streptococcal Bactaeremia in Allogeneic Bone Marrow Transplant Recipients," *Scand J. Infect. Dis.* 25:43–50.

Elsbach et al., 1993, *Current Opinion in Immunology* 5:103–107.

Haln et al., 1993, *Nature* 361:153–156.

Harwig et al., 1994, "Gallacins: cysteine–rich antimicrobial peptides of chicken leukocytes," *FEBS Lett.* 342:281–285.

Harwig et al., 1995, *J. Peptide Sci.* 3:207–215.

Harwig et al., 1995, *FEBS Lett.* 362:65–69.

Hoess et al., 1993, *EMBO Journal* 12:3351–3356.

Kokryakov et al., 1993, *FEBS Lett.* 327:231–236.

Lambert et al., 1989, *Proc. Natl. Acad. Sci. U.S.A.* 88:262–265.

Lehrer et al., 1985, *J. Virol.* 54:467–472.

Lehrer et al., 1991, *Cell* 64:229–230.

Lehrer et al., 1993, *Ann. Rev. Immunol.* 11:105–128.

Lerner, 1982, *Nature* 299:592–596.

Maloy & Kari, 1995, "Structure–activity studies on maganins and other host defense peptides," *Biopolymers (Peptide Science)* 37:105–122.

Masera et al., 1996, "Corticostatins/defensins inhibit in vitro NK activity and cytokine production by human peripheral blood mononuclear cells," *Regulatory Peptides* 62:13–21.

Masuda et al., 1992, "A novle anti–HIV synthetic peptide T–22 ([Tyr5, 12, Lys7]–polyphemusin II)," *Biochem. Biophys. Res. Commun.* 189:845–850.

Matsumoto et al., 1982, *Chem. and Pharma. Bulletin* 40(10):2701–2706.

Matsuzaki et al., 1991, "Interactions of an antimicrobial peptide, tachyplesin I, with lipid membranes," *Biochim. Biophys. Acta* 1070:259–264.

Matsuzaki et al., 1993, *Biochemistry* 32:11704–11710.

Mirgorodskaya et al., 1993, *FEBS Lett.* 330:339–342.

Miyata et al., 1989, *J. Biochem.* 106:663–668.

Morimoto et al., 1991, *Chemotherapy* 37:206–211.

Murakami et al., 1991, *Chemotherapy* 37:327–334.

Nakamura et al., 1988, *J. Biol. Chem.* 263:16709–16713.

Nakashima et al., 1992, *Antimicrobial Agents and Chemotherapy* pp. 1249–1255.

Olsson et al., 1991, *Biochim. Biophys. Acta* 1097:37–44.

Park et al., 1992, "Conformation of tachyplesin I from Tachypleus tridentatus when interacting with lipid matrices," *Biochemsitry* 31:12241–12247.

Pongor et al., 1987, *Methods in Enzymology* 154:450–473.

Robson et al., 1986, *Introduction to Proteins and Protein Engineering,* Elksevier, New York, p. 41.

Rustici et al., 1993, *Science* 259:361–364.

Schulesener et al., 1993, "Leukocyte antimicrobial peptides kill autoimmune T cells," *Journal of Neuroimmunology* 47:199–202.

Selsted et al., 1985, *J. Biol. Chem.* 260(8):4579–4584.

Selsted et al., 1992, "Enteric defensins: Antiobiotic peptide components of intestinal host defense," *J. Cell Biol.* 118:929–936.

Selsted et al., 1993, *J. Biol. Chem.* 268:6641–6648.

Storici et al., 1993, *Biochem. Biophys. Res. Commun.* 196:1363–1368.

Tamamura et al., 1993, "Antimicrobial activity and conformation of tachyplesin I and its analogs," *Chemical and Pharmaceutical Bulletin* 41:978–980.

Tamamura et al., 1993, "A comparative study of the solution structure of tachyplesin I and a novel anti–HIV synthetic peptide, T22, determined by nuclear magnetic resonance," *Biochim. Biophys. Acta* 1163:209–216.

Tamamura et al., 1995, "Synthesis of protegrin–related peptides and their antibacterial and anti–Human Immunodeficiency Virus activity," *Chemical and Pharmaceutical Bulletin* 43:853–858.

Zhao et al., 1994, *FEBS Lett.* 346:285–288.

Zhao et al., 1995, *FEBS Lett.* 368:197–202.

Zhao et al., 1995, *FEBS Lett.* 376:130–134.

Harwig, S. S.L. et al., 1996, "Intramolecular disulfide bonds enhance the antimicrobial and lytic activities of protegrins at physiological sodium chloride concentrations," *Eur. J. Biochem.* 240:352–357.

Yasin, B. et al., 1996, "Protegrins: Structural requirements for inactivating elementary bodies of Chlamydia trachomatis," *Infection and Immunity* 64(11):4863–4866.

```
ATGGAGACCCAGAGAGCCAGCCTGTGCCTGGGGCGCTGGTCACTGTGGCTTCTGCTGCTG    60
 M   E   T   Q   R   A   S   L   C   L   G   R   W   S   L   W   L   L   L   L
                                                                          G5
GCACTCGTGGTGCCCTCGGCCAGCGCCCAGGCCCTCAGCTACAGGGAGGCCGTGCTTCGT   120
 A   L   V   V   P   S   A   S   A   Q   A   L   S   Y   R   E   A   V   L   R
                                                                          G5
GCTGTGGATCGCCTCAACGAGCAGTCCTCGGAAGCTAATCTCTACCGCCTCCTGGAGCTG   180
 A   V   D   R   L   N   E   Q   S   S   E   A   N   L   Y   R   L   L   E   L
GACCAGCCGCCCAAGGCCgtgagtcgggcaggggctcaggaggggctgggggcggggc      240
 D   Q   P   P   K   A
tgtccccacccgccccggggctccctgtccctcccccctgctcaggctgtccctcctgcc   300 aggaaggcacttgtccctctaaggggggaccccctctgccaggaaaccttcccagagctgg   360 gtgccctgcccgcgtgagagcttcccgccttagcctctgggctgtgggctcagggccctg   420 cacagcctgtgaggcaggagcgggctctgtcccctcccctgtgcacccagcaccaagccc...480 agggccaggctcccagcaggggctgcagaggctgctgtctaggtgggggcggggaggggg   540 tgacagatccgagggggaagcctgagccccgagtcccatctccccactttgatccttgacc  600
                                A5
agGACGAGGACCCGGGCACCCCGAAACCTGTGAGCTTCACGGTGAAGGAGACTGTGTGTC   660
   D   E   D   P   G   T   P   K   P   V   S   F   T   V   K   E   T   V   C
CCAGGCCGACCCGGCAGCCCCCGGAGCTGTGTGACTTCAAGGAGAACGGGgtgaggctgg   720
 P   R   P   T   R   Q   P   P   E   L   C   D   F   K   E   N   G
gggctgggggcgctggcggatgcttcccaaggagctgaacaggagagcctgctggggaag   780 atgtccaggccctggggtgaggctgggagctcatggatggaggaggggggggtcccagttt   840
                                    t3
gaccttgagtctccccttccagCGGGTGAAACAGTGTGTGGGGACAGTCACCCTGGATCA   900
                       R   V   K   Q   C   V   G   T   V   T   L   D   Q
GATCAAGGACCCGCTCGACATCACCTGCAATGAGgtgagtggccccttattggtgtcaag   960
   I   K   D   P   L   D   I   T   C   N   E
ttgctaatgggttggtgtggggaactccttgggagtgttacccgctgccccatccagggc  1020 gtggaaaggccctcctaccccggcccttccctcacctcggccccagggctccaggtctgg  1080 ctctgtcatccttagggccgcggttccctcaatggggtccccccctcgtatttgtcagaa  1140
                                                           g3.5
aggcacatttcaggccccaccccgaccctctgaatcacactcttgggtggagcccagcct  1200 tgtctcttctcccaagatcccagcggggttcttcctgtgctgtcggctgagaggcagtgac 1260
```

FIG.1A cggactaatggacttgcaggccctgctcctggccagctttgcggggctgggtttgggacc 1320 ctggcaaggccccagccatctctgggcctgagtccacttatgtgtctgtgggggattcca 1381
                                      g3.5
                                      t5
ccacgtgctccaaaggtcacagccagaggtggaccagggcccccaagcctcttactgtttc 1440 cccattcagggattttttctagtctggagggagggttcttgtcttgacccttggacagacc 1500
                                            G3
ccacccgaaacctgtttctcttggtcacagGTTCAAGGTGTCAGGGGAGGTCGCCTGTGC 1560
                                V  Q  G  V  R  G  G  R  L  C
                                                            G3

C5                  T5
TATTGTAGGCGTAGGTTCTGCGTCTGTGTCGGACGAGGATGACGGTTGCGACGGCAGGCT 1620
 Y  C  R  R  R  F  C  V  C  V  G  R  G ***
                P5
TTCCCTCCCCCAATTTTTCCCGGGGCCAGGTTTCCGTCCCCCAATTTTTCCGCCTCCACCT 1680

TTCCGGCCCGCACCATTCGGTCCACCAAGGTTCCCTGGTAGACGGTGAAGGATTTGCAGG 1740
                            C3.5
CAACTCACCCAGAAGGCCTTTCGGTACATTAAAATCCCAGCAAGGAGACCTAAGCATCTG 1800

CTTTGCCCAGGCCCGCATCTGTCAAATAAATTCTTGTGAAACC 1843

FIG.1B

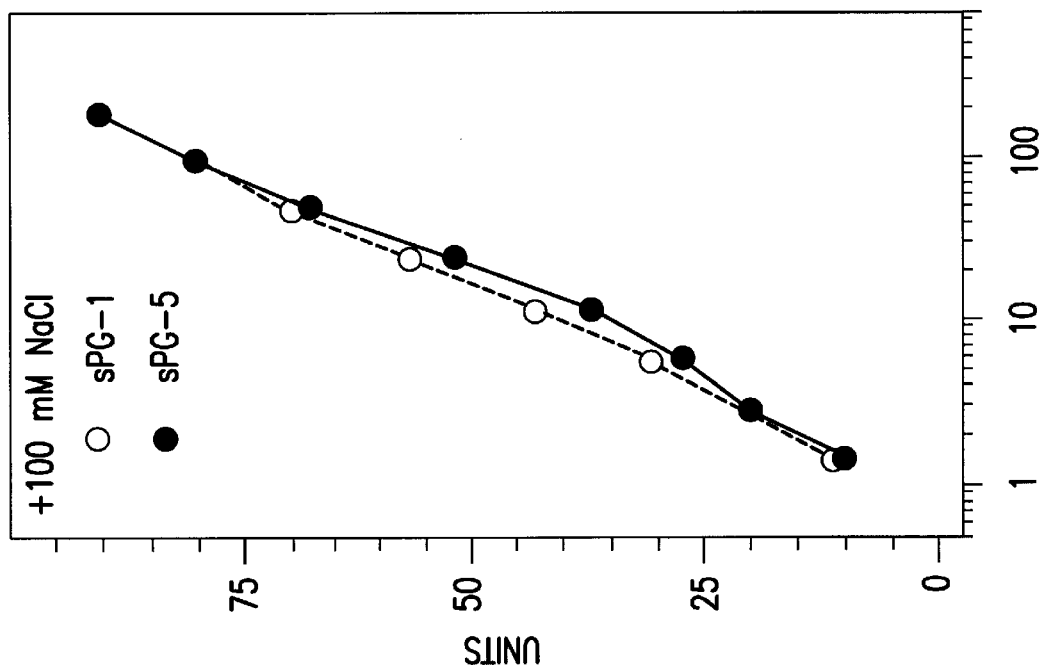
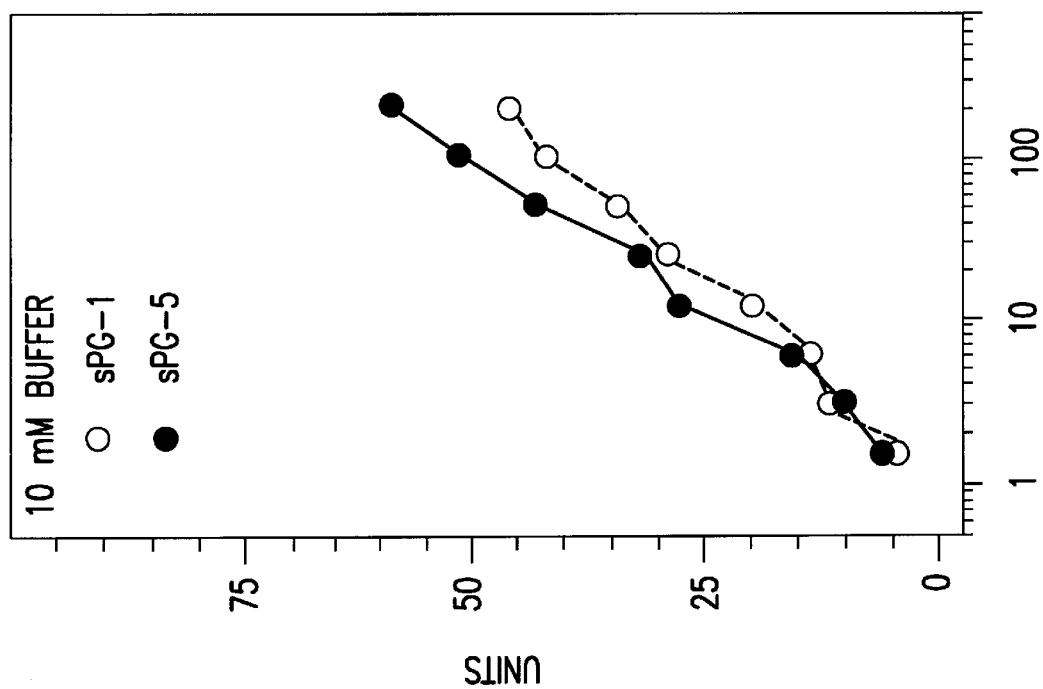

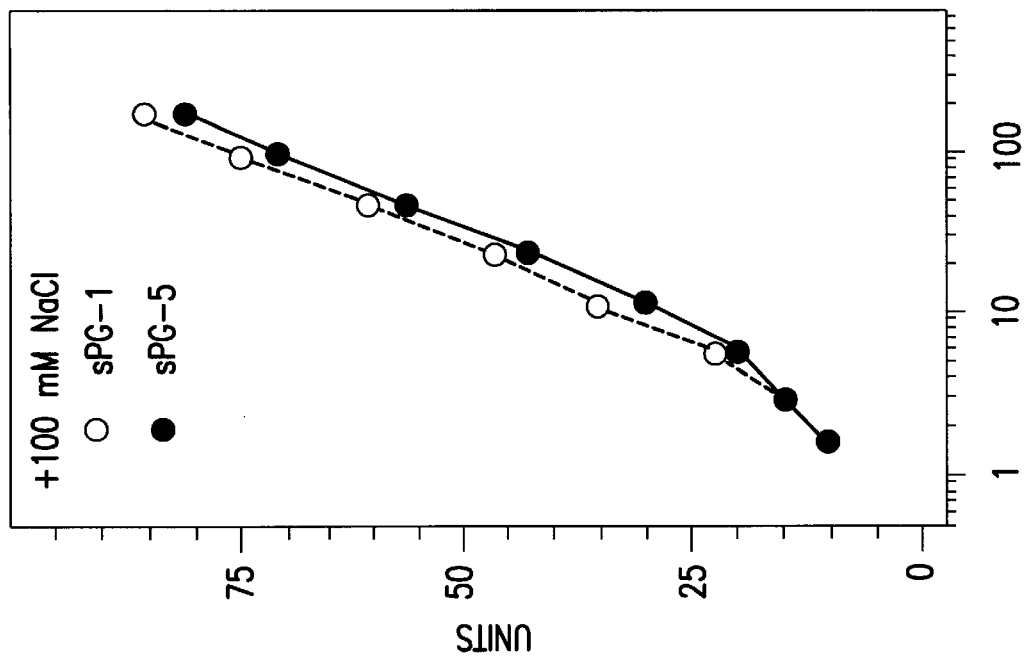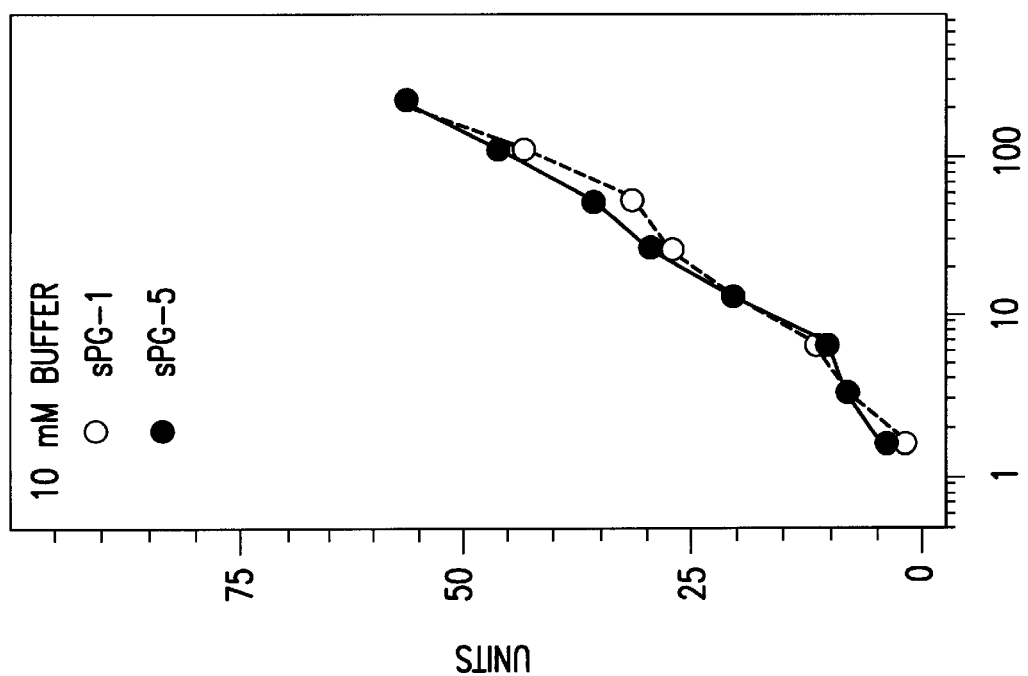

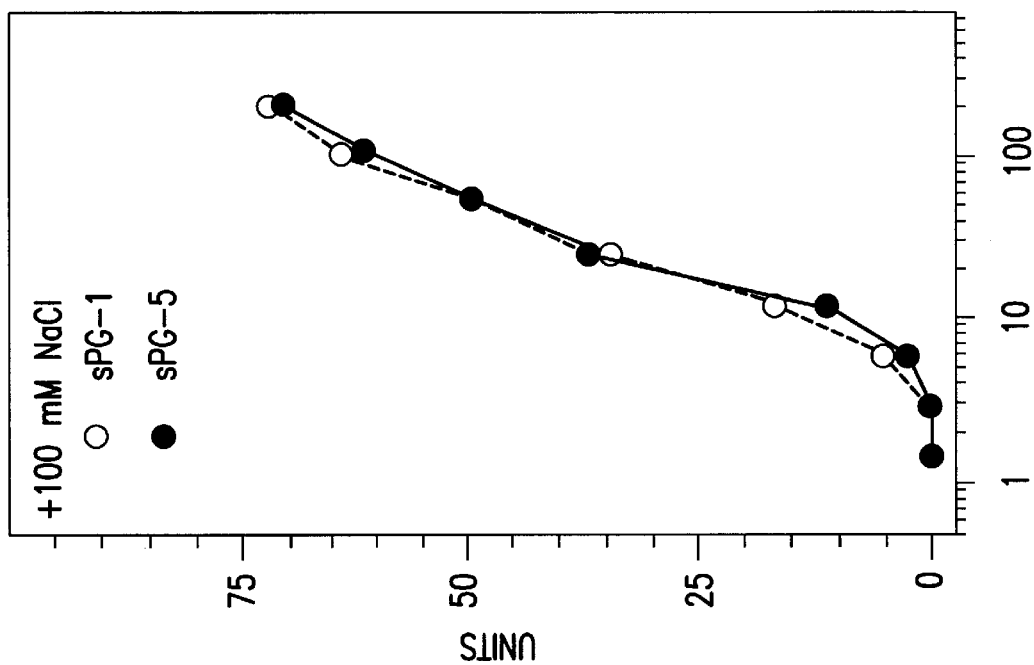
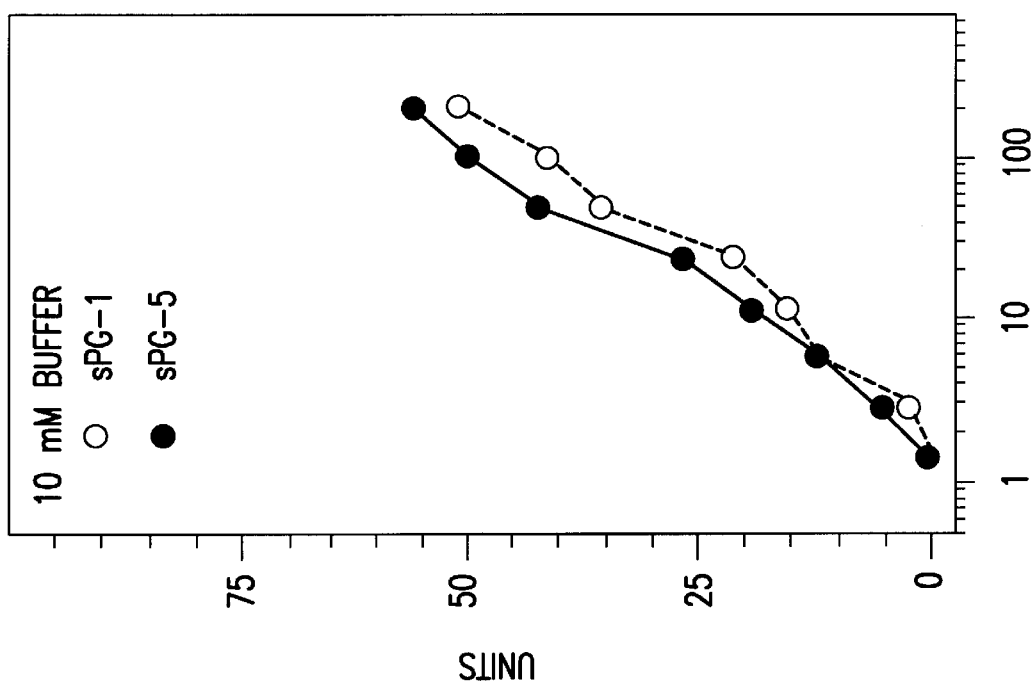

FINE-TUNED PROTEGRINS

1. CROSS-REFERENCE TO RELATED APPLICATIONS

This application is a continuation-in-part of U.S. Ser. No. 08/690,921 filed Aug. 1, 1996, and now abandoned which is a continuation-in-part of U.S. Ser. No. 08/649,811 filed May 17, 1996, and now abandoned which is a continuation-in-part of U.S. Ser. No. 08/562,346 filed Nov. 22, 1995, and now abandoned which is a continuation-in-part of U.S. Ser. No. 08/499,523 filed Jul. 7, 1995, which was issued as U.S. Pat. No. 5,804,558 and which is a continuation-in-part of U.S. Ser. No. 08/451,832 filed May 26, 1995 and now abandoned which claims priority as a continuation-in-part from PCT/US94/08305 filed Jul. 20, 1994, (WO 95/03325) and which is a continuation-in-part of U.S. Ser. No. 08/243,879 filed May 17, 1994, which was issued as U.S. Pat. No. 5,708,145 and which is a continuation-in-part of U.S. Ser. No. 08/182,483 filed Jan. 13, 1994, which was issued as U.S. Pat. No. 5,693,486 and which is a continuation-in-part of U.S. Ser. No. 08/095,769 filed Jul. 26, 1993, which was issued as U.S. Pat. No. 5,464,823 and which is a continuation-in-part of U.S. Ser. No. 08/093,926 filed Jul. 20, 1993, now abandoned. Benefit is claimed under 35 U.S.C. §120 with respect to U.S. Ser. Nos. 08/960,921, 08/649,811 and 08/562,346. The contents of these applications are incorporated herein by reference in their entireties.

This invention was made with funding from NIH Grant No. A122839. The U.S. Government has certain rights in this invention.

2. FIELD OF THE INVENTION

The invention relates to the field of antimicrobial peptides. In particular, the invention concerns short peptides, designated "protegrins," that have a wide range of antimicrobial activities.

3. BACKGROUND OF THE INVENTION

One of the defense mechanisms against infection by both animals and plants is the production of peptides that have antimicrobial and antiviral activity. Various classes of these peptides have been isolated from tissues of both plants and animals. PCT application WO 95/03325 (published Feb. 2, 1995) contains a review of the literature on this subject. Such peptides include tachyplesins, which are 17–18 amino acid peptides containing four invariant cysteines, the defensins, β-defensins, and insect defensins, which are somewhat longer peptides characterized by six invariant cysteines and antifungal and antibacterial peptides and proteins which have been found in plants.

The parent applications provide a new class of antimicrobial peptides, designated "protegrins," representative members of which have been isolated from porcine leukocytes. The protegrin peptides, which are generally amphiphilic in nature, exhibit broad spectrum antimicrobial activity. Thus, these peptides are useful as antibacterial, anti-fungal and antiviral agents in both plants and animals.

The isolation of some of the protegrin peptides of the invention was reported by the present applicants in a paper by Kokryakov, V. N. et al., 1993, *FEBS Lett* 337:231–236 (July issue). A later publication of this group described the presence of a new protegrin whose sequence, and that of its precursor, was deduced from its isolated cDNA clone. Zhao, C. et al., 1994, *FEBS Lett* 346:285–288. An additional paper disclosing cationic peptides from porcine neutrophils was published by Mirgorodskaya, O. A. et al., 1993, *FEBS Lett* 330:339–342. Storici, P. et al., 1993, *Biochem Biophys Res Comm* 196:1363–1367, report the recovery of a DNA sequence which encodes a pig leukocyte antimicrobial peptide with a cathelin-like prosequence. The peptide is reported to be one of the protegrins disclosed hereinbelow. Additional publications related to protegrins are Harwig, S. S. L., et al., 1995, *J Peptide Sci* 3:207; Zhao, C., et al., 1995, *FEBS Lett* 376:130–134; Zhao, C. et al., 1995, *FEBS Lett* 368:197–202; Miyakawa, Y. et al., 1996, *Infect Immun* 64:926–932; Yasin, B. et al., 1996, *Infect Immun* 64:709–713; Qu, X -D et al., 1996, *Infect Immun* 64:1240–1245; Aumelas, A. et al., 1996, *Eur J. Biochem* 237:575–583; Mangoni, M. E. et al., 1996, *FEBS Lett* 383:93–98; Steinberg et al., 1996, "Protegrins: Fast Acting Bacterial Peptides," presented at *8th Intl. Symposium on Staphylococci and Staphylococcal Infections,* Aix les Bains, France, Jun. 23–26, 1996; Steinberg et al., 1996, "Broad Spectrum Antimicrobial Activity of Protegrin Peptides," presented at *36th Interscience Conference on Antimicrobial Agents and Chemotherapy,* New Orleans, La., Sep. 15–18, 1996; Kung et al., 1996, "Protegrin Protects Mice From Systemic Infection By Antibiotic-Resistant Pathogens," presented at *36th Interscience Conference on Antimicrobial Agents and Chemotherapy,* New Orleans, La., Sep. 15–18, 1996; and Steinberg et al., 1996, "In Vitro Efficacy of Protegrins Against *Helicobacter Pylori,*" presented at *36th Interscience Conference on Antimicrobial Agents and Chemotherapy,* New Orleans, La., Sep. 15–18, 1996.

The protegrins have also been found to bind to endotoxins—i.e., the lipopolysaccharide (LPS) compositions derived from Gram-negative bacteria which are believed responsible for Gram-negative sepsis. The protegrins are also effective in inhibiting the growth of organisms that are associated with sexually transmitted diseases such as *Chlamydia trachomatis* and *Neisseria gonorrhoeae.*

The present invention is directed to a new set of protegrins which offer properties of being rapid acting microbicides having a broad spectrum of activity with a low likelihood of resistance. In addition, the class of protegrins of the present invention offers an additional opportunity to adjust the spectrum of activity with respect to the type of microbe or virus most effectively inhibited and with respect to the conditions under which this inhibition occurs. The protegrins in this case differ from those of the parent applications either by deletion of at least one of the four N-terminal amino acids, or of certain other designated residues and/or by replacement of certain amino acids with those of other classes.

4. SUMMARY OF THE INVENTION

In one aspect, the present invention is directed to antimicrobial peptides containing about 10–30 amino acid residues characterized by a "core" structure having two main elements: a reverse-turn bracketed by two strands that form an anti-parallel β-sheet. Generally, the β-sheet region of the molecule is amphiphilic, one surface being net hydrophobic in character, the other being net hydrophilic in character. The peptides contain at least one basic amino acid residue in the reverse-turn region, and have a net charge of at least +1 at physiological pH. The antimicrobial peptides may optionally be acylated at the N-terminus and/or amidated or esterified at the C-terminus, and may contain zero, one or two disulfide bridges.

In one illustrative embodiment, the invention provides antimicrobial peptides comprising about 10–30 amino acid residues and containing the amino acid sequence:

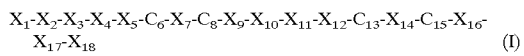

(I)

or a pharmaceutically acceptable salt or N-terminal acylated or C-terminal amidated or esterified form thereof, wherein:

each of $C_8$ and $C_{13}$ is independently present or notpresent, and if present each is independently a cysteine-like, basic, small, polar/large or hydrophobic;

each of $C_6$ and $C_{15}$ is independently a cysteine-like, basic, small, polar/large or hydrophobic amino acid;

each of $X_1-X_5$ is independently present or not present, and if present each is independently a basic, hydrophobic, polar/large, or small amino acid;

each of $X_7$ and $X_{14}$ is independently a hydrophobic or a small amino acid;

each of $X_9$ and $X_{12}$ is independently present or not present;

$X_9-X_{12}$ taken together are capable of effecting a reverse-turn when contained in the amino acid sequence of formula (I) and at least one of $X_9-X_{12}$ must be a basic amino acid;

each of $X_{16}-X_{18}$ is independently present or not present, and if present each is independently a basic, hydrophobic, polar/large or small amino acid;

and wherein at least about 15% up to about 50% of the amino acids comprising the antimicrobial peptide are basic amino acids such that the antimicrobial peptide has a net charge of at least +1 at physiological pH.

The peptides of the invention exhibit broad spectrum antimicrobial activity, being biocidal against a wide range of microbial targets, including Gram-positive bacteria, Gram-negative bacteria, yeast, fungi and protozoa. Accordingly, the peptides can be used as antimicrobial agents in a wide variety of applications. For example, the peptides can be used to preserve or disinfect a variety of materials, including medical equipment, foodstuffs, cosmetics, contact lens solutions, medicaments or other nutrient-containing materials. The peptides are also useful for the prophylaxis or treatment of microbial infections or diseases related thereto in both plants and animals.

In another aspect, the invention is directed to recombinant materials useful for the production of certain of the peptides of the invention as well as plants or animals modified to contain expression systems for the production of these peptides.

In another aspect, the invention is directed to pharmaceutical compositions and to compositions for application to plants containing the peptides of the invention as active ingredients or compositions which contain expression systems for production of the peptides or for in situ expression of the nucleotide sequence encoding these peptides.

In still another aspect, the invention is directed to methods of preparing the invention peptides synthetically, to antibodies specific for these peptides, and to the use of the peptides as preservatives.

In yet another aspect, the present invention is directed to methods of using the above-described peptides, or compositions thereof, to inhibit microbial growth. The method generally involves contacting a microbe with an antimicrobially effective amount of one or more of the peptides or compositions of the invention. In a preferred embodiment, a bacteria is contacted with a bactericidally effective amount of peptide or composition.

In a final aspect, the present invention is directed to methods of using the above-described peptides, or compositions thereof, to prevent or treat microbial infections or diseases related thereto in both plants and animals. The method generally involves administering to a plant or animal an effective amount of one or more of the peptides or compositions of the invention. Such diseases or infections include eye infections such as conjunctivitis and keratitis, corneal ulcers, stomach ulcers associated with *H. pylori*, sexually transmitted diseases (STDs), and Gram-negative sepsis. Clinically relevant infections that can be treated or prevented by the peptides of the invention include systemic infections caused by multi-drug resistant pathogens such as vancomycin-resistant *Enterococcus faecium*, methicillin-resistant *Staphylococcus aureus* and penicillin-resistant *Streptococcus pneumoniae*.

5. BRIEF DESCRIPTION OF THE DRAWINGS

FIG. 1 shows the nucleotide sequence and the deduced amino acid sequence of the genomic DNA encoding the precursor protein for the antimicrobial compounds PG-1, PG3, and PG-5.

FIGS. 3a–3c show the antimicrobial activity of synthetically prepared PG-5 as compared to that of synthetically prepared PG-1.

FIG. 5 is an illustration of the sequences of protegrins PG-1 through PG-5; and

Figure 2:
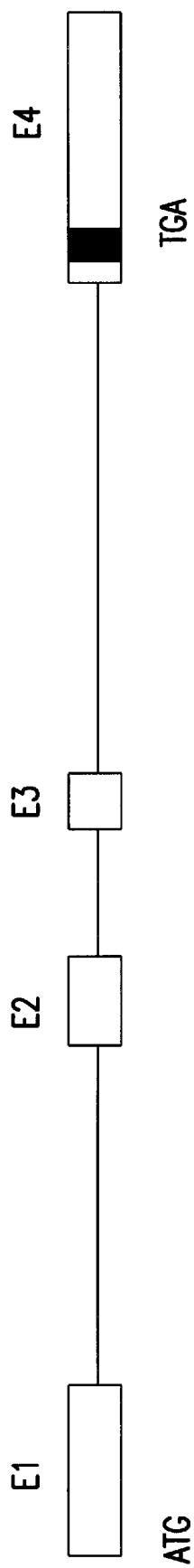
FIG. 2 shows the organization of the protegrin genomic DNA.

6. DETAILED DESCRIPTION OF THE INVENTION 6.1 Definitions

As used herein, the following terms shall have the following meanings:

"Secondary Structure:" As used herein, "secondary structure" refers to the regular local structure of segments of polypeptide chains including, but not limited to, helices such as α-helices, extended strands such as β-strands and sheets of extended strands such as β-sheets.

"Anti-Parallel β-Sheet:" As used herein "anti-parallel β-sheet" refers to a secondary structure of a polypeptide chain characterized by intermolecular backbone—backbone hydrogen bonding between anti-parallel peptide strands. An anti-parallel β-sheet may optionally contain one or two interstrand disulfide linkages.

"Amphiphilic Anti-Parallel β-Sheet:" As used herein, "amphiphilic anti-parallel β-sheet" refers to an anti-parallel β-sheet wherein one surface has a net hydrophobic character and another surface has a net hydrophilic character.

"Reverse-Turn:" As used herein, "reverse-turn" refers to a characteristic secondary structure that links adjacent strands of an anti-parallel β-sheet. Typically, a "reverse-turn" is a two to four amino acid residue peptide segment that reverses the direction of a polypeptide chain so as to allow a single polypeptide chain to adopt an anti-parallel β-sheet conformation.

Such peptide segments are well known in the art and include, by way of example and not limitation, three amino acid residue γ-turns (Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394) and four amino acid residue β-turns, as described below.

"β-Turn:" As used herein, "β-turn" refers to a recognized sub-class of reverse-turns. Typically, a "β-turn" is a four amino acid residue peptide segment that reverses the direction of a polypeptide chain so as to allow a single polypeptide chain to adopt an anti-parallel β-sheet secondary structure. Generally, the two internal amino acid residues of the β-turn are not involved in the hydrogen-bonding of the β-sheet; the two amino acid residues on either side of the internal residues are included in the hydrogen-bonding of the β-sheet. The term "β-turn" expressly includes all types of peptide β-turns commonly known in the art including, but not limited to, type-I, type-II, type-III, type-I', type-II' and type-III' β-turns (see, Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394).

"Antimicrobially Effective Amount:" As used herein, "antimicrobially effective amount" refers to an amount of peptide (or composition thereof) that is biostatic or biocidal against a target microbe. More specifically, an antimicrobially effective amount of peptide refers to an amount of peptide that inhibits the growth of, or is lethal to, a target microbe.

"Therapeutically Effective Amount" As used herein, "therapeutically effective amount" refers to an amount of peptide (or composition thereof) effective to ameliorate the symptoms of, or ameliorate, treat or prevent microbial infections or diseases related thereto in both plants and animals.

"Pharmaceutically Acceptable Salt:" As used herein, "pharmaceutically acceptable salt" refers to those salts which substantially retain the antimicrobial activity of the free bases and which are obtained by reaction with inorganic acids.

6.2 Description of the Preferred Embodiments

The present invention provides protegrin peptides having antimicrobial activity, compositions comprising the peptides, methods of using the peptides (or compositions thereof) to inhibit the growth of or kill a wide variety of microbial targets and methods of using the peptides (or compositions thereof) to treat or prevent microbial infections and diseases related thereto in both plants and animals.

The peptides of the invention exhibit broad spectrum antimicrobial activity, being biostatic or biocidal against a wide range of microbial targets, including but not limited to, Gram-positive bacteria such as *L. monocytogenes, B. subtilis, E. faecalis* (including vancomycin-sensitive (VSEF) and vancomycin-resistant (VREF) strains), *E. faecium* (including vancomycin-sensitive (VSEF) and vancomycin-resistant (VREF) strains), *S. aureus* (including methicillin-sensitive (MSSA) and methicillin-resistant (MRSA) strains), *S. epidermis* (including methicillin-sensitive (MSSE) and methicillin-resistant (MRSE) strains), *S. salivarius, C. minutissium, C. pseudodiptheriae, C. stratium,* Corynebacterium group G1, Corynebacterium group G2, *S. pneumoniae* (including penicillin-resistant (PSRP) strains), *S. mitis* and *S. sanguis;* Gram-negative bacteria including *A. calcoaceticus, E. coli, K. pneumoniae, P. aeruginosa, S. marcescens, H. influenza,* Moraxella sp., *N. meningitidis, S. typhimurium, H. pylori, H. felis,* and *C. jejuni;* as well as protozoa, yeast and certain strains of viruses and retroviruses. Significantly, the peptides described herein are biostatic or biocidal against clinically relevant pathogens exhibiting multi-drug resistance such as, among others, vancomycin-resistant *Enterococcus faecium* or *faecalis* ("VRE"), penicillin-resistant *Streptococcus pneumoniae* ("PRSP") and methicillin-resistant *Staphylococcus aureus* ("MRSA").

The peptides of the invention (or compositions thereof) are useful as biocidal or biostatic agents in a wide variety of applications. For example, the peptides can be used to disinfect or preserve a variety of materials including medical instruments, foodstuffs, medicaments, contact lens solutions, cosmetics and other nutrient-containing materials. The peptides of the invention are particularly useful as bacteriostatic or bactericidal agents against multi-drug-resistant pathogens such as VRE, MRSA and MSSE in a variety of clinical settings.

The peptides of the invention, or compositions thereof, are also useful for the prophylaxis or treatment of microbial infections and diseases related thereto in both plants and animals. Such diseases include, but are not limited to, Gram-negative and Gram-positive bacterial infections, endocarditis, pneumonia and other respiratory infections, urinary tract infections, systemic candidiasis, oral mucositis, etc.

The peptides described herein provide significant advantages over traditional antibiotics and/or other antimicrobial peptides. For example, as the peptides described herein are related to antimicrobial peptides found naturally animals, it is believed that the relatively high frequency of resistance observed for traditional antibiotics will not be observed for the peptides described herein.

A particular advantage of some of the protegrins of the invention, especially the "mini-protegrin" form having fewer than eighteen amino acids, lies in their reduced size. As a consequence, they are less costly to produce, generally are expected to provide better distribution in tissue and are less immunogenic.

6.2.1 The Peptides

Generally, the protegrin peptides of the invention include the amino acid sequence:

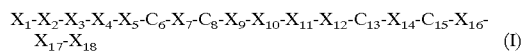

(I)

and its defined modified forms. Those peptides which may coincidentally occur in nature must be in a purified and/or isolated form or prepared synthetically or recombinantly.

The designation $X_n$ in each case represents an amino acid at the specified position in the peptide. Similarly, the designation $C_n$ represents an amino acid at the specified position and further represents those positions in the amino acid sequence of formula (I) which may optionally contain amino acid residues capable of forming disulfide interlinkages.

The amino acid residues denoted by $X_n$ or $C_n$ may be the genetically encoded L-amino acids, naturally occurring non-genetically encoded L-amino acids, synthetic L-amino acids or D-enantiomers of all of the above. The amino acid notations used herein for the twenty genetically encoded L-amino acids and common non-encoded amino acids are conventional and are as follows:

Common Amino Acid Abbreviations

| Amino Acid | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Ornithine | O | Orn |
| β-alanine | | bAla |
| 2,3-diaminopropionic acid | | Dpr |
| α-aminoisobutyric acid | | Aib |
| N-methylglycine (sarcosine) | | MeGly |
| Citrulline | | Cit |
| t-butylalanine | | t-BuA |
| t-butylglycine | | t-BuG |
| N-methylisoleucine | | MeIle |
| phenylglycine | | Phg |
| cyclohexylalanine | | Cha |
| Norleucine | | Nle |
| 1-naphthylalanine | | 1-Nal |
| 2-naphthylalanine | | 2-Nal |
| 4-chlorophenylalanine | | Phe(4-Cl) |
| 2-fluorophenylalanine | | Phe(2-F) |
| 3-fluorophenylalanine | | Phe(3-F) |
| 4-fluorophenylalanine | | Phe(4-F) |
| Penicillamine | | Pen |
| 1,2,3,4-tetrahydro-isoquinoline-3-carboxylic acid | | Tic |
| β-2-thienylalanine | | Thi |
| Methionine sulfoxide | | MSO |
| Homoarginine | | Har |
| N-acetyl lysine | | AcLys |
| 2,4-diamino butyric acid | | Dbu |
| p-aminophenylalanine | | Phe(pNH$_2$) |
| N-methylvaline | | MeVal |
| Homocysteine | | hCys |
| Homoserine | | hSer |
| ε-amino hexanoic acid | | Aha |
| δ-amino valeric acid | | Ava |
| 2,3-diaminobutyric acid | | Dab |
| Hydroxyproline | | Hyp |
| Parabenzylphenylalanine | | Pba |
| Homophenylalanine | | hPhe |
| N-methylphenylalanine | | MePhe |

The compounds of the invention are peptides which are partially defined in terms of amino acid residues of designated classes. Amino acid residues can be generally subclassified into major subclasses as follows:

Acidic: The residue has a negative charge due to loss of H$^+$ ion at physiological pH and the residue is attracted by aqueous solution so as to seek the surface positions in the conformation of a peptide in which it is contained when the peptide is in aqueous medium at physiological pH.

Basic: The residue has a positive charge due to association with H$^+$+ ion at physiological pH and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Polar/large: The residues are not charged at physiological pH, but the residue is not sufficiently repelled by aqueous solutions so that it would necessarily seek an inner position in the conformation of the peptide in which it is contained when the peptide is in aqueous medium. Depending on the conditions, and on the remaining amino acids in the sequence, the residue may reside either in the inner space or at the surface of the protein.

Cysteine-Like: Residues having a side chain capable of participating in a disulfide linkage. Thus, cysteine-like amino acids generally have a side chain containing at least one thiol (SH) group, such as cysteine, homocysteine, penicillamine, etc., with cysteine being preferred.

Small: Certain neutral amino acids having side chains that are not sufficiently large, even if polar groups are lacking, to confer hydrophobicity. "Small" amino acids are those with four carbons or less when at least one polar group is on the side chain and three carbons or less when not.

The gene-encoded secondary amino acid proline (as well as proline-like imino acids such as 3-hydroxy proline and 4-hydroxy proline) is a special case due to its known effects on the secondary conformation of peptide chains, and is not, therefore, included in a group.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues.

Certain commonly encountered amino acids which are not genetically encoded of which the peptides of the invention may be composed include, but are not limited to, β-alanine (b-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg);

cyclohexylalanine (Cha); norleucine (Nle); 1-naphthylalanine (1-Nal); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (Har); N-acetyl lysine (AcLys); 2,3-diaminobutyric acid (Dab); 2,4-diaminobutyric acid (Dbu); p-aminophenylalanine (Phe(pNH$_2$)); N-methyl valine (MeVal); homocysteine (hCys); hydroxyproline (Hyp); Parabenzylphenylalanine (Pba); Homophenylalanine (hPhe); N-methylphenylalanine (MePhe); and homoserine (hSer). These amino acids also fall conveniently into the categories defined above.

The classifications of the above-described genetically encoded and non-encoded amino acids are summarized in Table 1, below. It is to be understood that Table 1 is for illustrative purposes only and does not purport to be an exhaustive list of amino acid residues that may comprise the peptides described herein.

TABLE 1

Amino Acid Classifications

| Classification | Genetically Encoded | Non-Genetically Encoded |
|---|---|---|
| Hydrophobic | Y, V, I, L, M, F, W | Phg, 1-Nal, 2-Nal, Thi, Tic, Phe(4-Cl), Phe(2-F), Phe(3-F), Phe(4-F), t-BuA, t-BuG, MeIle, Nle, MeVal, Cha, hPhe, MePhe, Pba |
| Acidic | D, E | |
| Basic | H, K, R | Dpr, Orn, hArg, Phe(p-NH$_2$), Dbu, Dab |
| Polar/Large | Q, N | Cit, AcLys, MSO |
| Small | G, S, A, T | bAla, MeGly, Aib, hSer |
| Cysteine-Like | C | Pen, hCys |

In the peptides of formula I, the symbol "–" between amino acid residues $X_n$ and/or $C_n$ generally designates a backbone interlinkage. Thus, the symbol "–" usually designates an amide linkage (—C(O)—NH). It is to be understood, however, that in all of the peptides of the invention one or more amide linkages may optionally be replaced with a linkage other than amide. Such linkages include, but are not limited to, —CH$_2$NH—, —CH$_2$S—, —CH$_2$CH$_2$—, —CH=CH— (cis and trans), —C(O)CH$_2$—, —CH(OH)CH$_2$— and —CH$_2$SO—.

Peptides having such linkages and methods for preparing such peptides are well-known in the art (see, e.g., Spatola, 1983, *Vega Data* 1(3) (general review); Spatola, 1983, "Peptide Backbone Modifications" In: *Chemistry and Biochemistry of Amino Acids Peptides and Proteins* (Weinstein, ed.), Marcel Dekker, New York, p. 267 (general review); Morley, 1980, *Trends Pharm. Sci.* 1:463–468; Hudson et al., 1979, *Int. J. Prot. Res.* 14:177–185 (—CH$_2$NH—, —CH$_2$CH$_2$—); Spatola et al., 1986, *Life Sci.* 38:1243–1249 (—CH$_2$—S); Hann, 1982, *J. Chem. Soc. Perkin Trans. I.* 1:307–314 (—CH=CH—, cis and trans); Almquist et al., 1980, *J. Med. Chem.* 23:1392–1398 (—COCH$_2$—); Jennings-White et al., *Tetrahedron. Lett.* 23:2533 (—COCH$_2$—); European Patent Application EP 45665 (1982) CA:97:39405 (—CH(OH)CH$_2$—); Holladay et al., 1983, *Tetrahedron Lett.* 24:4401–4404 (—C(OH)CH$_2$—); and Hruby, 1982, *Life Sci.* 31:189–199 (—CH$_2$—S—).

Generally, the peptides of the invention are comprised of about 10 to 30 amino acid residues. Thus, it is to be understood that while formula (I) designates eighteen specified amino acid positions comprising the "core" peptide structure, the peptides of the invention may contain fewer than or greater than 18 amino acids without deleteriously affecting, and in some cases even enhancing, the antimicrobial or other useful properties of the peptides. For peptides containing fewer than 18 amino acid residues, certain specified amino acids are not present within the peptide sequence, as will be discussed in more detail below. For peptides containing greater than 18 amino acid residues, the amino acid sequence shown as formula (I) may contain extensions at the N- and/or C-terminus of additional amino acid residues or peptide sequence. It is to be understood that such additional amino acid residues or peptide sequences are non-interfering in that they will not significantly deleteriously affect the antimicrobial activity of the peptide as compared with naturally occurring protegrins.

The peptides of the invention are characterized by a "core" structure containing two main elements or motifs: a reverse-turn region bracketed by two strands that form an anti-parallel β-sheet. While not intending to be bound by theory, it is believed that the antimicrobial activity of the compounds of formula (I) is in part associated with such a core structure.

The β-sheet region of the peptides comprises an N-strand (residues $X_1$–$C_8$) and a C-strand (residues $C_{13}$–$X_{18}$). The N-strand and C-strand are arranged anti-parallel to one another and are non-covalently linked together via backbone-backbone hydrogen bonds (for a detailed description of the structure of β-sheets the reader is referred to Creighton, 1993, *Protein Structures and Molecular Properties,* W. H. Freeman and Co., NY, and references cited therein). While not intending to be bound by theory, it is believed that the most important residues comprising the β-sheet region are residues $X_5$–$C_8$ and $C_{13}$–$X_{16}$.

Preferably, the β-sheet region of the peptides is amphiphilic, i.e., one surface of the β-sheet has a net hydrophobic character and the other surface has a net hydrophilic character. Referring to the β-sheet structure illustrated in FIG. 6, the side chains of L-amino acid residues adjacent to one another intrastrand-wise (residues n, n+1, n+2, etc.) point in opposite directions so as to be positioned on opposite surfaces of the β-sheet. The side chains of L-amino acid residues adjacent to one another interstrand-wise (residues n and c, n+1 and c+1, etc.) point in the same direction so as to be positioned on the same surface of the β-sheet. Using this general structural motif an amphiphilic antiparallel β-sheet is obtained by selecting amino acids at each residue position so as to yield a β-sheet having hydrophobic side chains positioned on one surface of the sheet and hydrophilic side chains positioned on the other.

Of course, it will be appreciated that as the surfaces of the amphiphilic anti-parallel β-sheet region need only have net hydrophobic or net hydrophilic character, each side chain comprising a particular surface need not be hydrophobic or hydrophilic. The surfaces may contain side chains that do not significantly alter the net character of the surface. For example, both the hydrophobic and hydrophilic surfaces may contain small amino acid side chains, as these side chains do not significantly contribute to the net character of the surface.

The β-sheet region of the peptides of formula I may contain from one to four cysteine-like amino acids, designated $C_6$, $C_8$, $C_{13}$ and $C_{15}$, which may participate in interstrand disulfide bonds. The peptides of the invention that contain at least two cysteine-like amino acid residues may be in straight-chain or cyclic form, depending on the extent of disulfide bond formation. The cyclic forms are the result of the formation of disulfide linkages among all or some of the four invariant cysteine-like amino acids. Cyclic forms of the invention include all possible permutations of disulfide bond formation. The straight-chain forms are convertible to the cyclic forms, and vice versa. Methods for forming disulfide bonds to create the cyclic forms are well known in the art, as are methods to reduce disulfides to form the linear compounds.

The naturally occurring protegrins (PG-1 through PG-5) contain two disulfide bonds; one between cysteines $C_6$–$C_{15}$ and another between cysteines $C_8$–$C_{13}$ (Harwig et al., 1995, *J. Peptide Sci.* 3:207). Accordingly, in those embodiments having two disulfide linkages, the $C_6$–$C_{15}$, $C_8$–$C_{13}$ form is preferred. Such peptides are designated "native" forms. However, it has been found that forms of the protegrins containing only one disulfide linkage are active and easily prepared. Preferred among embodiments having only one disulfide linkage are those represented by $C_6$–$C_{15}$ alone and by $C_8$–$C_{13}$ alone.

Forms containing a $C_6$–$C_{15}$ disulfide as the only disulfide linkage are generally designated "bullet" forms of the protegrins; those wherein the sole disulfide is $C_8$–$C_{13}$ are designated the "kite" forms. The bullet and kite forms can most conveniently be made by replacing each of the cysteine-like amino acid residues at the positions that are not involved in a disulfide linkage with amino acids that do not participate in disulfide bonds, preferably with small amino acids such as glycine, serine, alanine or threonine. Alternatively, $C_8$ and/or $C_{13}$ may be absent.

As the linearized or "snake" forms of the native peptides have valuable activities, the peptides of the invention include linearized forms wherein the sulfhydryl (SH) groups are chemically stabilized with suitable reagents. As defined herein, "SH-stabilized" forms of the peptides of the invention contain sulfhydryl groups that have been reacted with standard reagents to prevent reformation of disulfide linkages or forms wherein the cysteine-like amino acid residues are replaced by other amino acids as set forth above. It is preferred that all four cysteine-like amino acid residues be replaced or SH-stabilized in order to minimize the likelihood of the formation of intermolecular disulfide linkages.

The sulfur atoms involved in an interstrand disulfide bridge in a β-sheet are not positioned within the plane defined by the interstrand backbone-backbone hydrogen-bonds; the sulfur atoms are at an angle with respect to the β-carbons of the bridged amino acid residues so as to be positioned on a surface of the β-sheet. Thus, the sulfur atoms of the disulfide linkages contribute to the net hydrophilicity of a surface of the β-sheet. It is to be understood that in the peptides of formula I a β-sheet region defined by the following formula is specifically contemplated to fall within the definition of amphiphilic antiparallel sheet as described herein:

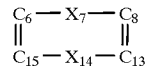

wherein $C_6$, $C_8$, $C_{13}$ and $C_{15}$ are each independently a cysteine-like amino acid, $X_7$ and $X_{14}$ are each independently a hydrophobic or small amino acid and ‖ is a disulfide bond. In a particularly preferred embodiment, $C_6$, $C_8$, $C_{13}$ and $C_{15}$ are each cysteine and $X_7$ and $X_{14}$ are each independently hydrophobic amino acids.

Figure 6:
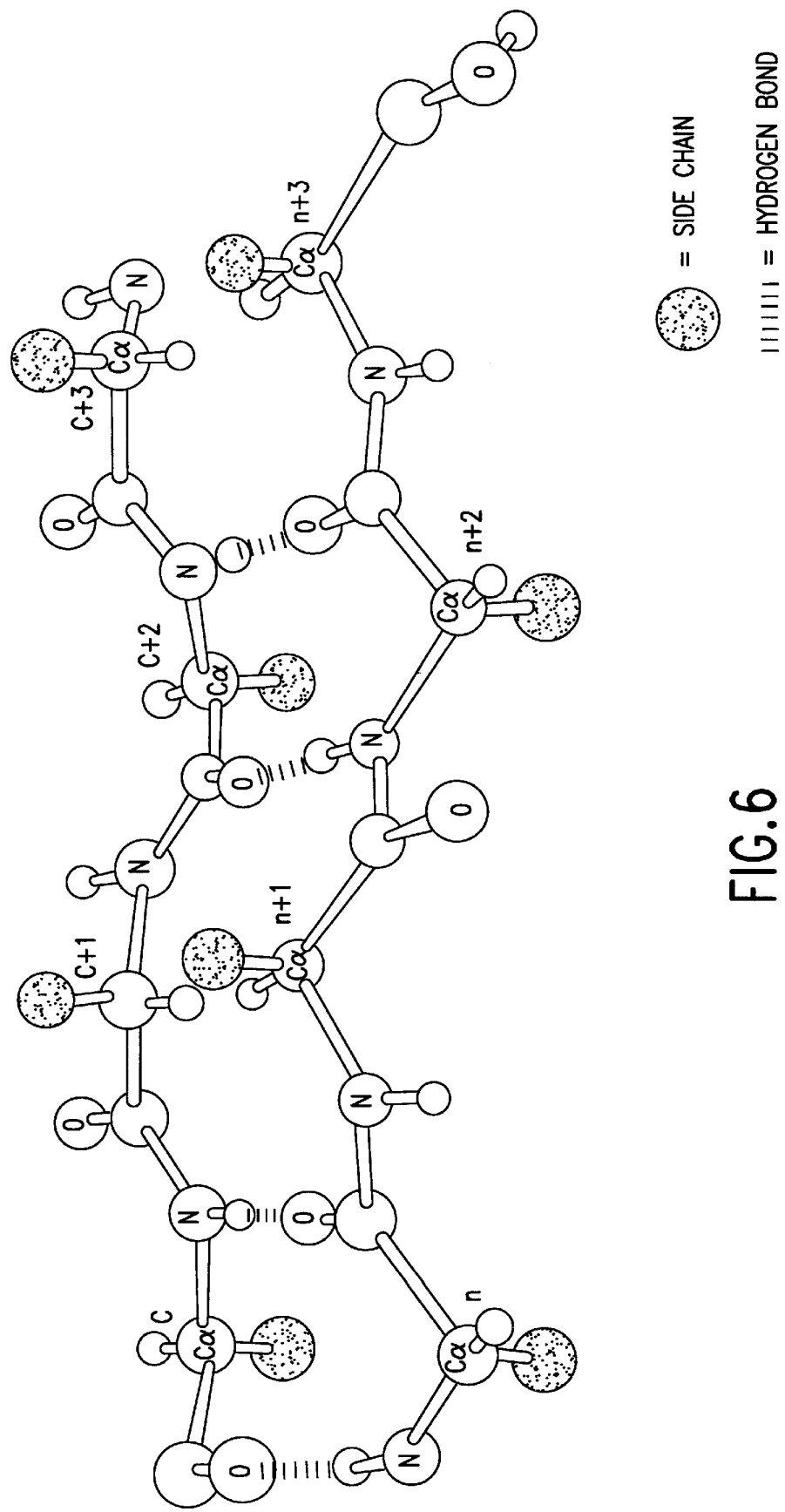
FIG. 6 is an illustration of a β-sheet secondary peptide structure.

The β-sheet secondary structure illustrated in FIG. 6 is composed entirely of L-amino acids. Those having skill in the art will recognize that substituting an L-amino acid with its corresponding D-enantiomer at a specific residue position may disrupt the structural stability or amphiphilicity of amphiphilic anti-parallel β-sheet region. The degree to which any particular enantiomeric substitution disrupts the structural stability or amphiphilicity depends, in part, on the size of the amino acid side chain and position of the residue within the β-sheet. Preferably, the β-sheet region of the peptides of formula I will contain mixtures of L- and D-amino acids that do not significantly affect the stability or amphiphilicity of the β-sheet region as compared to peptides containing the corresponding all D- or all L-enantiomeric forms of the sheet. Enantiomeric substitutions that do not substantially affect the stability or amphiphilicity of the β-sheet region will be readily apparent to those having skill in the art.

In a preferred embodiment of the invention, hydrophobic, basic, polar/large and cysteine-like amino acids comprising the p-sheet region are either all L-enantiomers or all D-enantiomers. Small amino acids comprising the β-sheet region may be either L-enantiomers or D-enantiomers.

The reverse-turn region of the peptides of formula I (residues $X_9$-$X_{10}$-$X_{11}$-$X_{12}$ taken together) links the strands of the anti-parallel β-sheet. Thus, the reverse-turn region comprises a structure that reverses the direction of the polypeptide chain so as to allow a region of the peptide to adopt an anti-parallel β-sheet secondary structure.

The reverse-turn region of the molecule generally comprises two, three or four amino acid residues (residue $X_9$ and/or $X_{12}$ may be absent). An important feature of the peptides of the invention is the presence of a positive charge in the turn region of the molecule. Thus, one of $X_9$–$X_{12}$, and preferably two of $X_9$–$X_{12}$, must be a basic amino acid. Such two, three and four amino acid segments capable of effecting a turn in a peptide are well known and will be apparent to those of skill in the art.

In a preferred embodiment of the invention, the reverse-turn is a three amino acid residue γ-turn. Virtually any γ-turn sequence known in the art may be used in the peptides of the invention, including those described, for example, in Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol* 206:759–777; and Tramontano et al., 1989, *Proteins: Struct. Funct. Genet.* 6:382–394.

In another preferred embodiment the reverse-turn is a four amino acid residue β-turn. In such structures, the two internal amino acid residues of the turn are usually not involved in the hydrogen-bonding of the anti-parallel β-sheet; the two amino acid residues on either side of the internal residues are usually included in the hydrogen-bonding of the β-sheet. While not intending to be bound by theory, it is believed that such hydrogen bonding helps stabilize the β-sheet region of the molecule.

The conformations and sequences of many peptide β-turns have been well-described in the art and include, by way of example and not limitation, type-I, type-I', type-II, type-II', type-III, type-III', type-IV, type-V, type-V', type-VIa, type-VIb, type-VII and type-VIII (see, Richardson, 1981, *Adv. Protein Chem.* 34:167–339; Rose et al., 1985, *Adv. Protein Chem.* 37:1–109; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394). All of these types of peptide β-turn structures and their corresponding sequences, as well as later discovered peptide β-turn structures and sequences, are specifically contemplated by the invention.

The specific conformations of short peptide turns such as β-turns depend primarily on the positions of certain amino acid residues in the turn (usually Gly, Asn or Pro). Generally, the type-I β-turn is compatible with any amino acid residue at positions $X_9$ through $X_{12}$, except that Pro cannot occur at position $X_{11}$. Gly predominates at position $X_{12}$ and Pro predominates at position $X_{10}$ of both type-I and type-II turns. Asp, Asn, Ser and Cys residues frequently occur at position $X_9$, where their side chains often hydrogen-bond to the NH of residue $X_{11}$.

In type-II turns, Gly and Asn occur most frequently at position $X_{11}$, as they adopt the required backbone angles most easily. Ideally, type-I' turns have Gly at positions $X_{10}$ and $X_{11}$, and type-II' turns have Gly at position $X_{10}$. Type-III turns generally can have most amino acid residues, but type-III' turns usually require Gly at positions $X_{10}$ and $X_{11}$.

Type-VIa and VIb turns generally have a cis peptide bond and Pro as an internal residue. For a review of the different types and sequences of β-turns in proteins and peptides the reader is referred to Wilmot et al., 1988, *J. Mol. Biol.* 203:221–232.

Preferred β-turn sequences are as follows (listed in order $X_9$ to $X_{12}$): ZZZG; ZZZF; ZZSG; ZZAL; ZGZL; ZFZL; ZPZV; ZPZF; ZGZY; IZGZ; LZZF; YZGZ, wherein each Z is independently an L- or D-enantiomer of R, K, Dbu or Orn.

Additional preferred β-turns include those wherein $X_{10}$ and/or $X_{11}$ are Tic or Hyp, as these residues are known to effect or induce β-turn structures in peptides and proteins.

The peptides of the invention are generally basic, i.e., they have a net positive charge at physiological pH. While not intending to be bound by theory, it is believed that the presence of positively charged amino acid residues, particularly in the turn region of the molecule, is important for antimicrobial activity.

It is understood that in a statistical collection of individual amino acid residues in a structure such as a peptide some of the amino acid residues will be positively charged, some negatively charged and some uncharged. Thus, some of the peptides will have a charge and some not. To fit the definition of "basic," an excess of amino acid residues in the peptide molecule are positively charged at physiological pH. Thus, approximately 15% but no more than up to about 50% of the amino acids must be basic amino acids, and the compounds must have a net charge of at least +1 at physiological pH. Preferably, the peptides of the invention will have a net charge of at least +3 at physiological pH.

For embodiments having as few as 10 amino acids, there may be only one basic amino acid residue; however, at least two basic residues, even in this short-chain residue, are preferred. If the protegrin peptide contains as many as 15 amino acid residues, two basic residues are required. It is preferred that at least 20% of the amino acids in the sequence be basic, with 30% basic amino acids being particularly preferred.

The amino terminus of the peptides of the invention may be in the free amino form or may be acylated by a group of the formula RCO—, wherein R represents a hydrocarbyl group of 1–25C, preferably 1–10C, more preferably 1–8C. The hydrocarbyl group can be saturated or unsaturated, straight chain, branched or cyclic, and is typically, for example, methyl, ethyl, isopropyl, t-butyl, n-pentyl, cyclohexyl, cyclohexene-2-yl, hexene-3-yl, hexyne-4-yl, octyl, decyl, eicanosyl and the like, with octyl being preferred.

Alternatively, the N-terminus may contain aromatic groups such as naphthalene, etc. Such groups may be conveniently incorporated into the peptides of the invention by using amino acids such as 1-naphthylalanine or 2-naphthylalanine as the N-terminal amino acid residue.

The N-terminus of the peptides may also be substituted to use solute-specific transmembrane channels to facilitate their entry into the bacterial periplasm. For example, the N-terminus may be conveniently modified with catechol using catechol-NHS activated ester.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. In some embodiments, it is difficult to make salts since the remainder of the molecule bears a positive charge which may repel the relevant cation. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–25C as defined and with preferred embodiments as above. Amidated forms of the peptides wherein the C-terminus has the formula $CONH_2$ are preferred.

Addition of lipophilic groups at the C- and/or N-terminus facilitates the transition of the peptide into the membrane of the target microbe and penetration into sites of infection. Choice of optimum substitution is determined by evaluation with respect to the lipid content of the target microbe.

Thus, in one illustrative embodiment, the invention provides antimicrobial peptides comprised of about 10–30 amino acid residues and containing the amino acid sequence:

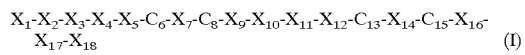

$$X_1\text{-}X_2\text{-}X_3\text{-}X_4\text{-}X_5\text{-}C_6\text{-}X_7\text{-}C_8\text{-}X_9\text{-}X_{10}\text{-}X_{11}\text{-}X_{12}\text{-}C_{13}\text{-}X_{14}\text{-}C_{15}\text{-}X_{16}\text{-}X_{17}\text{-}X_{18} \quad (I)$$

or a pharmaceutically acceptable salt or N-terminal acylated or C-terminal amidated or esterified form thereof, wherein:

each of $C_8$ and $C_{13}$ is independently present or not present, and if present each is independently a cysteine-like, basic, small, polar/large or hydrophobic;

each of $C_6$ and $C_{15}$ is independently a cysteine-like, basic, small, polar/large or hydrophobic amino acid;

each of $X_1$–$X_5$ is independently present or not present, and if present each is independently a basic, hydrophobic, polar/large, or small amino acid;

each of $X_7$ and $X_{14}$ is independently a hydrophobic or a small amino acid;

each of $X_9$ and $X_{12}$ is independently present or not present;

$X_9$–$X_{12}$ taken together are capable of effecting a reverse turn when contained in the amino acid sequence of formula (I) and at least one of $X_9$–$X_{12}$ must be a basic amino acid;

each of $X_{16}$–$X_{18}$ is independently present or not present, and if present each is independently a basic, hydrophobic, polar/large or small amino acid;

and wherein at least about 15% up to about 50% of the amino acids comprising said antimicrobial peptide are basic amino acids such that said antimicrobial peptide has a net charge of at least +1 at physiological pH.

In one class of protegrins described herein, either the hydrophobic amino acids found in the naturally occurring protegrins at $X_5$ are replaced with a basic amino acid and/or at least one of $X_1$–$X_4$ is hydrophobic and/or at least one, and preferably all four of amino acids $X_1$ and $X_4$ found in the native forms are deleted; and/or one or more of $X_5$, $C_8$, $X_9$, $X_{12}$, $C_{13}$ and $X_{16}$ is absent. By suitable manipulation of these and other features, the range of conditions under which the class of protegrins of the present invention are effective can be varied. Furthermore, the spectrum of microbes against which they are effective can also be modified.

In another class, the peptides of the invention are comprised of about 10–14 amino acid residues and each of $C_8$ and $C_{13}$ is independently present or not present, and if present each is independently a small, hydrophobic or polar/large amino acid or cysteine;

- each of $C_6$ and $C_{15}$ is independently a small, hydrophobic or polar/large amino acid or cysteine;
- each of $X_1$–$X_5$ is independently present or not present, and if present each is independently a basic or small amino acid and any two of $X_1$–$X_5$ may be a hydrophobic amino acid;
- each of $X_7$ and $X_{14}$ is independently a hydrophobic amino acid;
- each of $X_9$ and $X_{12}$ is independently present or not present, and if present each is independently a basic or hydrophobic amino acid;
- $X_{10}$ is a basic, hydrophobic or small amino acid or proline;
- $X_{16}$ is present or not present, and if present is a basic, small or hydrophobic amino acid;
- each of $X_{17}$ and $X_{18}$ is independently present or not present, and if present each is independently a basic or small amino acid.
- each of $X_{16}$–$X_{18}$ is independently present or not present, and if present each is independently a basic, hydrophobic, polar/large or small amino acid.

In another class, the peptides of the invention are comprised of about 10–18 amino acid residues and each of $C_8$ and $C_{13}$ is independently present or not present, and if present each is independently a small, hydrophobic or polar/large amino acid or cysteine;

- each of $C_6$ and $C_{15}$ is independently a small, hydrophobic or polar/large amino acid or cysteine;
- each of $X_1$–$X_4$ is independently present or not present, and if present each is independently a basic or small amino acid and any one of $X_1$–$X_4$ may be a hydrophobic amino acid;
- each of $X_5$ and $X_{16}$ is independently present or not present, and if present each is independently a hydrophobic or basic amino acid;
- each of $X_7$ and $X_{14}$ is independently a hydrophobic amino acid;
- $X_9$ is present or not present, and if present is a basic or hydrophobic amino acid;
- $X_{10}$ is a basic or small amino acid or proline;
- $X_{11}$ is a basic or hydrophobic amino acid;
- $X_{12}$ is present or not present, and if present is a hydrophobic amino acid;
- $X_{17}$ present or not present, and if present is independently a small amino acid; and
- $X_{18}$ is present or not present, and if present is a basic amino acid.

The invention peptides can be further illustrated by way of preferred embodiments. In one preferred embodiment of the invention, all of the cysteine-like amino acid residues at positions $C_6$, $C_8$, $C_{13}$ and $C_{15}$ are present as are $X_9$ and $X_{12}$.

In another set of preferred embodiments, all of $X_1$–$X_4$ are not present. In another set of preferred embodiments, at least one, and preferably two of $X_1$–$X_4$ is a hydrophobic amino acid, preferably I, V, L, Y, F or W.

In another set of preferred embodiments, $X_9$–$X_{12}$ contain at least one hydrophobic amino acid residue, preferably Phe, Tyr or Trp.

Other preferred embodiments include those peptides wherein each of $X_1$ and $X_9$ is independently selected from the group consisting of R, K, Orn, Dab and Har or hydrophobic; preferably $X_1$ is R, K, Har and $X_9$ is R, K, Har or hydrophobic, especially I, V, L, W, F or Y. However, each of $X_1$ and $X_9$ may be absent.

In another class of preferred embodiments, each of $X_2$ and $X_3$ is independently selected from the group consisting of G, A, S, T, I, V, L, F, Y and W; more preferably, $X_2$ and $X_3$ are G, W, F, Y, L, or V; however, $X_2$ and/or $X_3$ may be absent.

In another set of preferred embodiments, $X_4$ is selected from the group consisting of R, K, H, Orn, Har, Dab, G, A, S, T, F, Y and W; more preferably, $X_4$ is R, K, Orn, Dab, G or W; however, $X_4$ may be absent.

In another set of preferred embodiments, each of $X_5$ and $X_{16}$ is independently selected from the group consisting of I, V, L, Nle, W, Y, and F, preferably I, V, L, W, F and Y. However, $X_5$ and/or $X_{16}$ may be absent.

In another set of preferred embodiments, each of $X_7$ and $X_{14}$ is independently selected from the group consisting of I, V, L, W, Y and F; preferably $X_7$ is I, F, Y or W and $X_{14}$ is I, V, L, W, Y, or F.

In another set of preferred embodiments, $X_9$ is R, K, H, Orn, Dab, Har, I, V, L, Nle, W, Y or F, and $X_{12}$ is I, L, V, W, F or Y; more preferably and aromatic amino acid such as Y, W, or F.

In another set of preferred embodiments, $X_{10}$ is R, Orn, Dab, G, W or P.

In another set of preferred embodiments, $X_{11}$ is R, K, Orn, Dab, G, W or P.

In another set of preferred embodiments, $X_{17}$ is preferably absent, but when present, is preferably G, A, S or T;

In another set of preferred embodiments, $X_{18}$ is preferably absent, but when present, is preferably R, K, H, Orn, Dab or Har.

Also preferable when all four amino acids $X_1$–$X_4$ are present, $X_1$ and $X_4$ are preferably basic and $X_2$ and $X_3$ are small or hydrophobic. Preferred embodiments of $X_1$–$X_4$ include R—G—G—R, R—G—W—R, R—L—L—R and the like.

Preferred embodiments for the basic amino acid to replace cysteine-like residues are R, K, H, Orn, Dab and Har, most preferably R, K or Orn. Preferred small amino acids to replace the cysteine-like residues include G, A, S and T, most preferably A and T.

Particularly preferred peptides of the invention include the native, kite, bullet and/or snake forms of the following peptides:

| | |
|---|---|
| Form-21 | R-G-G-R-L-Z-Y-Z-R-R-R-F-Z-V-Z-V |
| | R-G-G-R-R-Z-Y-Z-R-R-R-F-Z-V-Z-V |
| | R-G-G-R-L-Z-Y-Z-R-R-R-F-Z-V-Z-R |
| | R-G-G-R-R-Z-Y-Z-R-R-R-F-Z-V-Z-R |
| | R-Z-Y-Z-R-R-R-F-Z-V-Z-V |
| | L-Z-Y-Z-R-R-R-F-Z-V-Z-R |
| | R-Z-Y-Z-R-R-R-F-Z-V-Z-R |
| | L-Z-Y-Z-R-R-R-F-Z-V-Z-V |
| Form-22 | R-G-G-R-L-Z-Y-Z-R-R-R-F-Z-I-Z-V |
| | R-G-G-R-R-Z-Y-Z-R-R-R-F-Z-I-Z-V |
| | R-G-G-R-L-Z-Y-Z-R-R-R-F-Z-I-Z-R |
| | R-G-G-R-R-Z-Y-Z-R-R-R-F-Z-I-Z-R |
| | R-Z-Y-Z-R-R-R-F-Z-I-Z-V |

|        |                                  |
|--------|----------------------------------|
|        | L-Z-Y-Z-R-R-R-F-Z-I-Z-R          |
|        | R-Z-Y-Z-R-R-R-F-Z-I-Z-R          |
|        | L-Z-Y-Z-R-R-R-F-Z-I-Z-V          |
| Form-23 | R-G-G-G-L-Z-Y-Z-R-R-R-F-Z-V-Z-V |
|        | R-G-G-G-R-Z-Y-Z-R-R-R-F-Z-V-Z-V  |
|        | R-G-G-G-L-Z-Y-Z-R-R-R-F-Z-V-Z-R  |
|        | R-G-G-G-R-Z-Y-Z-R-R-R-F-Z-V-Z-R  |
|        | R-Z-Y-Z-R-R-R-F-Z-V-Z-V          |
|        | L-Z-Y-Z-R-R-R-F-Z-V-Z-R          |
|        | R-Z-Y-Z-R-R-R-F-Z-V-Z-R          |
|        | L-Z-Y-Z-R-R-R-F-Z-V-Z-V          |
| Form-24 | R-G-G-R-L-Z-Y-Z-R-G-W-I-Z-F-Z-V |
|        | R-G-G-R-R-Z-Y-Z-R-G-W-I-Z-F-Z-V  |
|        | R-G-G-R-L-Z-Y-Z-R-G-W-I-Z-F-Z-R  |
|        | R-G-G-R-R-Z-Y-Z-R-G-W-I-Z-F-Z-R  |
|        | R-Z-Y-Z-R-G-W-I-Z-F-Z-V          |
|        | L-Z-Y-Z-R-G-W-I-Z-F-Z-R          |
|        | R-Z-Y-Z-R-G-W-I-Z-F-Z-R          |
|        | L-Z-Y-Z-R-G-W-I-Z-F-Z-V          |
| Form-25 | R-G-G-R-L-Z-Y-Z-R-P-R-F-Z-V-Z-V |
|        | R-G-G-R-R-Z-Y-Z-R-P-R-F-Z-V-Z-V  |
|        | R-G-G-R-L-Z-Y-Z-R-P-R-F-Z-V-Z-R  |
|        | R-G-G-R-R-Z-Y-Z-R-P-R-F-Z-V-Z-R  |
|        | R-Z-Y-Z-R-P-R-F-Z-V-Z-V          |
|        | L-Z-Y-Z-R-P-R-F-Z-V-Z-R          |
|        | R-Z-Y-Z-R-P-R-F-Z-V-Z-R          |
|        | L-Z-Y-Z-R-P-R-F-Z-V-Z-V          | and the N-acylated and/or C-amidated or esterified forms thereof wherein each Z is independently a hydrophobic, small or basic amino acid or cysteine, as well as the foregoing forms wherein $X_7$ is W and/or $X_{12}$ is W and/or wherein $X_{14}$ is W and/or wherein $X_{16}$ is W and/or wherein $X_{17}$ is G and $X_{18}$ is R; and/or wherein at least one of $X_5$, $X_9$, $X_{12}$ and $X_{16}$ is not present. In all of these embodiments, Z is preferably S, A, T or G, most preferably A or T.

Figure 5:
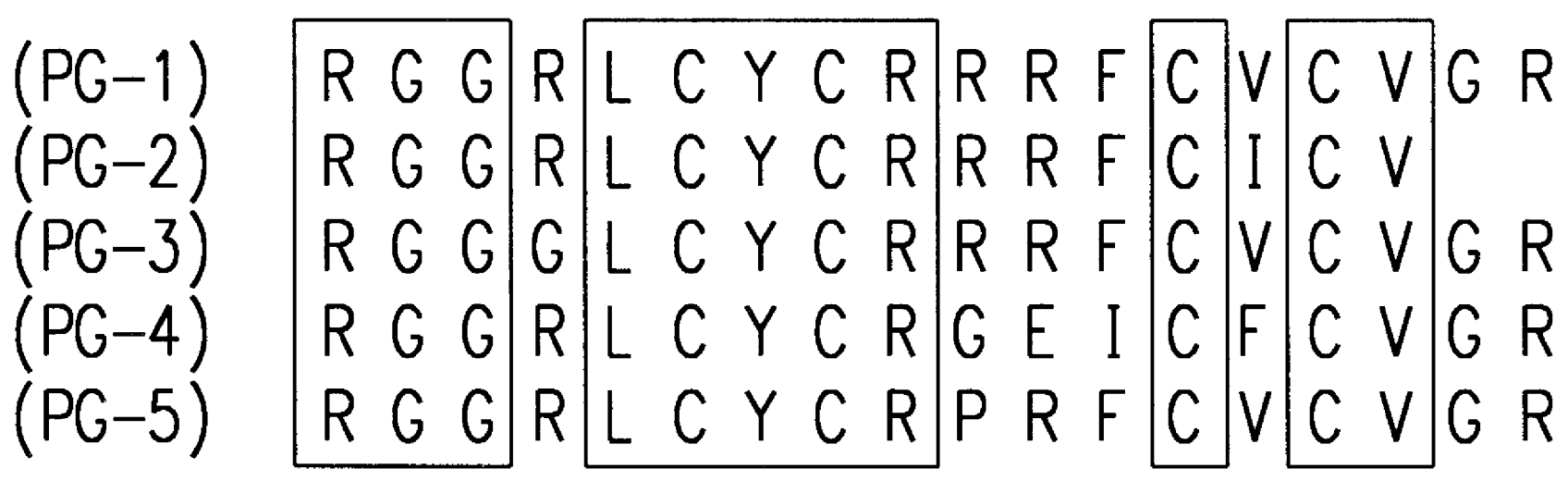

In the foregoing peptides, protegrin form 21 consists of compounds which are characteristic of the present class but which are otherwise similar to protegrin-1 (PG-1); form 22 contains the characteristics of the present class but is otherwise similar to protegrin-2 (PG-2); forms 23 through 25 are similarly related to protegrins -3, -4 and -5 (PG-3, PG-4 and PG-5) (see FIG. 5).

Another set of preferred compounds includes the native, bullet, kite and snake forms of the following peptides (sequences are shown aligned to protegrin PG-1):

| CODE | SEQUENCE | |
|------|----------|---|
| PG-1 | RGGRLCYCRRRFCVCVGR | (SEQ ID NO:1) |
|      | WLCFCRRRFCVCV | (SEQ ID NO:2) |
|      | FLCFCRRRFCVCV | (SEQ ID NO:3) |
|      | WYCYCRRRFCVCV | (SEQ ID NO:4) |
|      | WXCYCRRRFCVCV (X = Cha) | (SEQ ID NO:5) |
|      | WLCYCRRRFCVCVGR | (SEQ ID NO:6) |
|      | WXCYCRRRFCVCVGR (X = Cha) | (SEQ ID NO:7) |
|      | RLLRLCYCRRRFCVCVGR | (SEQ ID NO:8) |
|      | RGGRLCYCRRRFCXCVGR (X = MeVal) | (SEQ ID NO:9) |
|      | RGVCVCFRRRCYCLW | (SEQ ID NO:10) |
|      | RGVCVCFRRRCYCLW | (SEQ ID NO:11) |
|      | VCVCFRRRCYCLW | (SEQ ID NO:12) |
|      | FCVCFRRRCFCLF | (SEQ ID NO:13) |
|      | RGVCVCFRRRCYCRGGR | (SEQ ID NO:14) |
|      | RGVCVCFRRRCYCLRGGR (all D) | (SEQ ID NO:15) |
|      | RGVCVCFRRRCYCLW | (SEQ ID NO:16) |
|      | RGVCVCYRXRCYCLW (X = MeGly) | (SEQ ID NO:17) |
|      | WLCYCRXZYCVCVGR (X = MeGly) (Z = D-Arg) | (SEQ ID NO:18) |
|      | RGFCVCFRRVCYCLW | (SEQ ID NO:19) |
|      | WLCYCRRRFCVCVGR | (SEQ ID NO:20) |
|      | WLCYCRRXFCVCVR (X = D-Arg) | (SEQ ID NO:21) |
|      | WLCYCKKKFCVCVGK | (SEQ ID NO:22) |
|      | Octyl-WLCYCRRRFCVCVGR | (SEQ ID NO:23) |

| CODE | SEQUENCE | |
|------|----------|---|
|  | XLCYCRRRFCVCV (X = 1-Nal) | (SEQ ID NO:24) |
|  | WLC RGRF CVR | (SEQ ID NO:25) |
|  | WLC RGRF CFR | (SEQ ID NO:26) |
|  | WLCY RR VCVR | (SEQ ID NO:27) |
|  | WLCYCOOOFCVCV | (SEQ ID NO:28) |
|  | WLCYCXXXFCVCV (X = Dab) | (SEQ ID NO:29) |
|  | WLCYCRRRFCVCV (all D) | (SEQ ID NO:30) |
|  | HWRLCYCRPKFCVCV | (SEQ ID NO:31) |
|  | KWRLCYCRPKFCVCV | (SEQ ID NO:32) |
|  | OWRLCYCRPKFCVCV | (SEQ ID NO:33) |
|  | XWRLCYCRPKFCVCV (X = Dab) | (SEQ ID NO:34) |
|  | RWHLCYCRPKFCVCV | (SEQ ID NO:35) |
|  | RWKLCYCRPKFCVCV | (SEQ ID NO:36) |
|  | RWOLCYCRPKFCVCV | (SEQ ID NO:37) |
|  | RWXLCYCRPKFCVCV (X = Dab) | (SEQ ID NO:38) |
|  | WLCYCKXKFCVCVGR (X = Tic) | (SEQ ID NO:39) |
|  | FCYCKXKFCYCV (X = Hyp) | (SEQ ID NO:40) |
|  | WLXYXRRRFXVXV (X = hCys) | (SEQ ID NO:41) |
|  | WOLCYCOXOFCVCVO (X = Tic) | (SEQ ID NO:42) |
|  | OFCVCVOXOFCVCVO (X = Tic) | (SEQ ID NO:43) |
|  | OWOLCYCOXOFCVCV (X = Tic) | (SEQ ID NO:44) |
|  | OFCVCXOLCYCFO (X = Tic) | (SEQ ID NO:45) |
|  | WLCYCKKKFCVCV | (SEQ ID NO:46) |
|  | OWOLCYCOXOFCVCV (X = Hyp) | (SEQ ID NO:47) |
|  | WLCYCOXOFCVCVO (X = Pba) | (SEQ ID NO:48) |
|  | WLCYCOOOFCVCV (all D) | (SEQ ID NO:49) |
|  | XFCYCLRXFCVCVR (X = D-Arg) | (SEQ ID NO:50) |
|  | WLCYCRRXFCVCVZX (X = D-Arg) (Z = MeGly) | (SEQ ID NO:51) |
| PC11 | LCYCRRRFCVCVGR | (SEQ ID NO:52) |
| PC12 | RCYCRRRFCVCV | (SEQ ID NO:53) |
| PC15 | RGGRLCYCRRRFCVCR | (SEQ ID NO:54) |
| PC16 | RCYCRRRFCVCR | (SEQ ID NO:55) |
| PC17 | LCYCRRRFCVCV | (SEQ ID NO:56) |
| PC18 | LCYARRRFAVCV | (SEQ ID NO:57) |
| PC19 | RCYARRRFAVCR | (SEQ ID NO:58) |
| PC20 | LAYCRRRFCVAV | (SEQ ID NO:59) |
| PC21 | RAYCRRRFCVAR | (SEQ ID NO:60) |
| PC22 | RGGRLCY RR VCV | (SEQ ID NO:61) |
| PC31 | GGRLCYCRRRFCVCV | (SEQ ID NO:62) |
| PC32 | RGRLCYCRRRFCVCV | (SEQ ID NO:63) |
| PC33 | GRLCYCRRRFCVCV | (SEQ ID NO:64) |
| PC34 | RRLCYCRRRFCVCV | (SEQ ID NO:65) |
| PC35 | RLCYCRRRFCVCV | (SEQ ID NO:66) |
| PC36 | RRCYCRRRFCVCV | (SEQ ID NO:67) |
| PC37 | CYCRRRFCVCV | (SEQ ID NO:68) |
| PC44 | RGGRLCYCRRRFCVC | (SEQ ID NO:69) |
| PC47 | RGGRLCY RRRF VCV | (SEQ ID NO:70) |
| PC48 | RGWRLCYCRRRFCVCV | (SEQ ID NO:71) |
| PC37a | CYCRRRFCVCVGR | (SEQ ID NO:72) |
| PC45 | RGGRLCYCRRRFCV | (SEQ ID NO:73) |
| PC72 | LCYCRRRFCVC | (SEQ ID NO:74) |
| PC64 | LCYTRRRFTVCV | (SEQ ID NO:75) |
| PC64a | LTYCRRRFCVTV | (SEQ ID NO:76) |
| PC31a | GGRLCYCRRRFCVCVGR | (SEQ ID NO:77) |
| PC32a | RGRLCYCRRRFCVCVGR | (SEQ ID NO:78) |
| PC33a | GRLCYCRRRFCVCVGR | (SEQ ID NO:79) |
| PC34a | RRLCYCRRRFCVCVGR | (SEQ ID NO:80) |
| PC35a | RLCYCRRRFCVCVGR | (SEQ ID NO:81) |
| PC36a | RRCYCRRRFCVCVGR | (SEQ ID NO:82) |
| PC44a | RGGRLCYCRRRFCVCR | (SEQ ID NO:83) |
| PC47a | RGGRLCY RRRF VCVGR | (SEQ ID NO:84) |
| PC48a | RGWRLCYCRRRFCVCVGR | (SEQ ID NO:85) |
| PC54 | RGWRLAYCRRRFCVAVGR | (SEQ ID NO:86) |
| PC61 | RCYCRRRFCVCV | (SEQ ID NO:87) |
| PC62 | LCYCRRRFCVCR | (SEQ ID NO:88) |
| PC63 | VCYCFRRRFCYCV | (SEQ ID NO:89) |
| PC65 | LCYTRPRFTVCV | (SEQ ID NO:90) |
| PC66 | LCYTRGRFTVCV | (SEQ ID NO:91) |
| PC67 | LCYFRRRFIVCV | (SEQ ID NO:92) |
| PC68 | LCYFRPRFIVCV | (SEQ ID NO:93) |
| PC69 | LCYTFRPRFVCV | (SEQ ID NO:94) |
| PC70 | LCYTFRGRFVCV | (SEQ ID NO:95) |
| PC74 | CYCFRRRFCVC | (SEQ ID NO:96) |
| PC77 | LCYCRRRRCVCV | (SEQ ID NO:97) |
| PC78 | LCYCFRRRCVCV | (SEQ ID NO:98) |
| PC79 | LCYCRFRRCVCV | (SEQ ID NO:99) |

-continued

| CODE | SEQUENCE | |
|---|---|---|
| PC80 | LCYCRRFRCVCV | (SEQ ID NO:100) |
| PC81 | LCYCRRFFCVCV | (SEQ ID NO:101) |
| PC82 | LCYCRFFRCVCV | (SEQ ID NO:102) |
| PC83 | LCYCFFRRCVCV | (SEQ ID NO:103) |
| PC84 | LCYCFRRFCVCV | (SEQ ID NO:104) |
| PC85 | LCYCFRFRCVCV | (SEQ ID NO:105) |
| PC86 | LCYCFRFRCVCV | (SEQ ID NO:106) |
| PC87 | LCYCFRFFCVCV | (SEQ ID NO:107) |
| PC88 | LCYCFFRFCVCV | (SEQ ID NO:108) |
| PC89 | LCYCFFFRCVCV | (SEQ ID NO:109) |
| PC90 | LCYCRFFFCVCV | (SEQ ID NO:100) |
| | RGGRLCY RR VCVGR | (SEQ ID NO:111) |
| PC91 | YCYCRRRFCVCVGR | (SEQ ID NO:112) |
| PC95 | ICYCRRRFCVCVGR | (SEQ ID NO:113) |
| PC96 | FCYCRRRFCVCVGR | (SEQ ID NO:114) |
| PC97 | WCYCRRRFCVCVGR | (SEQ ID NO:110) |
| PC99 | RCYCRRRFCVCVGR | (SEQ ID NO:116) |
| PC109 | RLCYTRGRFTVCV | (SEQ ID NO:117) |
| PC110 | LCYTRGRFTVCVR | (SEQ ID NO:118) |
| PC111 | RLCYTRGRFTVCVR | (SEQ ID NO:119) |
| PC112 | LCYCHHHFCVCV | (SEQ ID NO:120) |
| PC113 | LCYTHHHFTVCV | (SEQ ID NO:121) |
| | RGGLCYCRRRFCVCVGR | (SEQ ID NO:122) |
| | RGGRLCYCRRRFCVCVGR | (SEQ ID NO:123) |
| | RGGGLCYCRRRFCVCVGR | (SEQ ID NO:124) |
| | RGGGLCYCRRGFCVCFGR | (SEQ ID NO:125) |
| | RGGGLCYCRRPFCVCVGR | (SEQ ID NO:126) |
| | RGGGLCYCRPRFCVCVGR | (SEQ ID NO:127) |
| | RGGRLCYCRXRFCVCVGR (X = MeGly) | (SEQ ID NO:128) |
| | RGGLCYCRGRFCVCVGR | (SEQ ID NO:129) |
| | RGGRLCYCXGRFCVCVGR (X = Cit) | (SEQ ID NO:130) |
| | XGGRLCYCRGRFCVCVGR (X = Cit) | (SEQ ID NO:131) |
| | RGGRVCYCRGRFCVCVGR | (SEQ ID NO:132) |
| | RGGGLCYCFPKFCVCVGR | (SEQ ID NO:133) |
| | RGWGLCYCRPRFCVCVGR | (SEQ ID NO:134) |
| | RGWRLCYCRXRFCVCVGR (X = MeGly) | (SEQ ID NO:135) |
| | RGWRLCYCRGRFCVCVGR | (SEQ ID NO:136) |
| | RGWRLCYCXPRFCVCVGR (X = Cit) | (SEQ ID NO:137) |
| | RWRLCYCRPRFCVCVGR | (SEQ ID NO:138) |
| | RGWRLCYCRPRFCVCVGR | (SEQ ID NO:139) |
| | RGWRACYCRPRFCACVGR | (SEQ ID NO:140) |
| | GWRLCYCRPRFCVCVGR | (SEQ ID NO:141) |
| | RWRLCYCKGKFCVCVGR | (SEQ ID NO:142) |
| | RGWRLCYCRXRFCVCVGR (X = MeGly) | (SEQ ID NO:143) |
| | GGWRLCYCRGRFCVCVGR | (SEQ ID NO:144) |
| | RGGWLCYCRGRFCVCVGR | (SEQ ID NO:145) |
| | RLLRLCYCRXRFCVCVGR (X = MeGly) | (SEQ ID NO:146) |
| | RLLRACYCRXRFCVCVGR (X = MeGly) | (SEQ ID NO:147) |
| | RLLRLCYCRRRFCVCVGR | (SEQ ID NO:148) |
| | RGLRXCYCRGRFCVCVGR (X = Cha) | (SEQ ID NO:149) |
| | RGGRLCYCRXRZCVCWGR (X = MeGly) (Z = Cha) | (SEQ ID NO:150) |
| | RGGRWCVCRXRZCYCVGR (X = MeGly) (Z = Cha) | (SEQ ID NO:151) |
| | RGLRXCYCRGRFCVCVGR (X = Cha) | (SEQ ID NO:152) |
| | RGGRWCVCRGRXCYCVGR (X = Cha) | (SEQ ID NO:153) |
| | RGGRLCYCRRRFCXCVGR (X = MeVal) | (SEQ ID NO:154) |
| | LCYCRRRFCVCV | (SEQ ID NO:155) |
| | LCYCRRCFCVCV | (SEQ ID NO:156) |
| | LCYCRRRFCVCF | (SEQ ID NO:157) |
| | LCACRRRACVCV | (SEQ ID NO:158) |
| | LCYCRXRFCVCV (X = D-Arg) | (SEQ ID NO:159) |
| | LCWCRRRFCVCV | (SEQ ID NO:160) |
| | WCYCRRRFCVCV | (SEQ ID NO:161) |
| | LCYCRRRXCVCV (X = hPhe) | (SEQ ID NO:162) |
| | LCYCRRRXCVCV (X = Phe(4-Cl)) | (SEQ ID NO:163) |
| | XCYCRRRFCVCV(X = Cha) | (SEQ ID NO:164) |
| | LCYCRRRFCXCV (X = D-His) | (SEQ ID NO:165) |
| | LCYCRRRXCVCV (X = MeGly) | (SEQ ID NO:166) |
| | LCYCRRRXCVCV (X = MePhe) | (SEQ ID NO:167) |
| | LCYCRRRFCXCV (X = MeVal) | (SEQ ID NO:168) |
| | LCXCRRRXCVCV (X = Cha) | (SEQ ID NO:169) |
| | LCGCRRRGCVCV | (SEQ ID NO:170) |
| | LCACRGRACVCV | (SEQ ID NO:171) |
| | RACYCRPRFCACV | (SEQ ID NO:172) |
| | RLCYCRPRFCVCF | (SEQ ID NO:173) |
| | RLCYCRPRFCVCV | (SEQ ID NO:174) |
| | KLCYCKPKFCVCV | (SEQ ID NO:175) |
| | RLCACRGRACVCV | (SEQ ID NO:176) |
| | RLCYCRXRFCVCV (X = MeGly) | (SEQ ID NO:177) |
| | RXCFCRPRFCVCV (X = Cha) | (SEQ ID NO:178) |
| | RWCFCRPRFCVCV | (SEQ ID NO:179) |
| | WLCYCRRRFCVCV | (SEQ ID NO:180) |
| | WLCFCRRRFCVCV | (SEQ ID NO:181) |
| | FLCFCRRRFCVCV | (SEQ ID NO:182) |
| | WLCFCRRRXCVCV (X = MePhe) | (SEQ ID NO:183) |
| | WYCYCRRRFCVCV | (SEQ ID NO:184) |
| | WXCYCRRRFCVCV (X = Cha) | (SEQ ID NO:185) |
| | RXCFCRGRZCVCV (X = Cha) (Z = MePhe) | (SEQ ID NO:186) |
| | XLCFCRRRZCVCV (X = Cha) (Z = MePhe) | (SEQ ID NO:187) |
| | RLCYCRPRFCVCVGR | (SEQ ID NO:188) |
| | WLCYCRRRFCVCVGR | (SEQ ID NO:189) |
| | WXCYCRRRFCVCVGR (X = Cha) | (SEQ ID NO:190) |
| | RLCYCRGPFCVCR | (SEQ ID NO:191) |
| | RRWCFVCYAGFCYRCR | (SEQ ID NO:192) |
| | RRCYCRGRFCGCVGR | (SEQ ID NO:193) |
| | RWRCYCGRRFCGCVGR | (SEQ ID NO:194) |
| | RARCYCGRRFCGCVGR | (SEQ ID NO:195) |
| | GWRCYCGRRFCGC | (SEQ ID NO:196) |
| | RGWACYCGRRFCVC | (SEQ ID NO:197) |
| | RRCYGRRRFGVCVGR | (SEQ ID NO:198) |
| | RGWRLCYGRGRFKVC | (SEQ ID NO:199) |
| | RGWRLCYCRGRFCVC | (SEQ ID NO:200) |
| | CYCRRRFCVCF | (SEQ ID NO:201) |
| | RGWRLCYCRXRFCVC (X = MeGly) | (SEQ ID NO:202) |
| | RGWRGCYCRXRFCGC (X = MeGly) | (SEQ ID NO:203) |
| | LCYCRPRFCVCVGR | (SEQ ID NO:204) |
| | LCYCKPKFCVCVGK | (SEQ ID NO:205) |
| | LCYCRGRFCVCVGR | (SEQ ID NO:206) |
| | LCYCRPRFCVCVGRGR | (SEQ ID NO:207) |
| | RRWCYCRPRFCVCVR | (SEQ ID NO:208) |
| | WRLCYCRPRFCVCVGR | (SEQ ID NO:209) |
| | GWLCYCRGRFCVCVGR | (SEQ ID NO:210) |
| | RWLCYCRGRFCVCVGR | (SEQ ID NO:211) |
| | RLLCYCRGRFCVCVGR | (SEQ ID NO:212) |
| | RWRLCYCRPRFCVCV | (SEQ ID NO:213) |
| | RXRLCYCRZRFCVCV (X = Cha) (Z = MeGly) | (SEQ ID NO:214) |
| | RGWRLCYCRGRXCVCV (X = Cha) | (SEQ ID NO:215) |
| | RGGRVCYCRGRFCVCV | (SEQ ID NO:216) |
| | LCYCRXRFCVCV (X = D-Ala) | (SEQ ID NO:217) |
| | LCYCKPKFCVCV | (SEQ ID NO:218) |
| | VCYCRPRFCVCV | (SEQ ID NO:219) |
| | LCYCRPRFCVCW | (SEQ ID NO:220) |
| | LCYRRPRFRVCV | (SEQ ID NO:221) |
| | RGWRLCYCRGRXCVCV (X = Cha) | (SEQ ID NO:222) |
| | RXRLCYCRZRFCVCV (X = Cha) (Z = MeGly) | (SEQ ID NO:223) |
| | RXRLCYCRGRFCVCV (X = Cha) | (SEQ ID NO:224) |
| | RGGGLCYARGWIAFCVGR | (SEQ ID NO:225) |
| | RGGGLCYARGFIAVCFGR | (SEQ ID NO:226) |
| | RGGGLCYARPRFAVCVGR | (SEQ ID NO:227) |
| | RGGGLCYTRPRFTVCVGR | (SEQ ID NO:228) |
| | RGGGLCYARKGFAVCVGR | (SEQ ID NO:229) |
| | RGGRLCYARRRFAVCVGR | (SEQ ID NO:230) |
| | RGGGLCYKRGFIKVCFGR | (SEQ ID NO:231) |
| | RGGGLCYKRGWIKFCVGR | (SEQ ID NO:232) |
| | RGGGLCYRLPKFRVCVGR | (SEQ ID NO:233) |
| | RGGGLCYRLPGFRVCVGR | (SEQ ID NO:234) |
| | RGWRGCYKRGRFKGCVGR | (SEQ ID NO:235) |
| | LCYKRGRFKVCV | (SEQ ID NO:236) |
| | ICYRPRFVCVGR | (SEQ ID NO:237) |
| | WLCYCRRRFCVCV | (SEQ ID NO:238) |
| | RLCYCRRRFCVCV | (SEQ ID NO:240) |
| | RGRVCLRYCRGRFCVRLCFR | (SEQ ID NO:241) |
| | RRRLCYCRRRFCVCVGR | (SEQ ID NO:242) | and the N-acylated and/or C-amidated or esterified forms thereof.

6.2.2 Preparation of the Compounds

The invention compounds, often designated herein "protegrins" are essentially peptide backbones which may be modified at the N- or C-terminus and also may contain one or two disulfide linkages. The peptides may first be synthesized in noncyclized form. These peptides may then be converted to the cyclic peptides if desired by standard methods of disulfide bond formation. As applied to the protegrins herein, "cyclic forms" refers to those forms which contain cyclic portions by virtue of the formation of disulfide linkages between cysteine-like amino acid residues in the peptide. If the non-cyclized forms are preferred, it is preferable to stabilize the sulfhydryl groups for any peptides of the invention which contain two or more cysteine-like residues.

Standard methods of synthesis of peptides of the sizes described herein are known. Most commonly used currently are solid phase synthesis techniques; indeed, automated equipment for systematically constructing peptide chains can be purchased. Solution phase synthesis can also be used and has considerable benefits for large scale production. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group at the amino terminus. Methods for acetylating or, more generally, acylating, the free amino group at the N-terminus are generally known in the art; in addition, the N-terminal amino acid may be supplied in the synthesis in acylated form.

At the carboxyl terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. However, when the compound of formula (I) contains a multiplicity of basic residues, salt formation may be difficult or impossible. The carboxyl terminus may also be esterified using alcohols of the formula ROH wherein R is hydrocarbyl as defined above. Similarly, the carboxyl terminus may be amidated so as to have the formula $—CONH_2$, $—CONHR$, or $—CONR_2$, wherein each R is independently hydrocarbyl as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

For synthesis of linear peptide with a C-terminal amide, the peptide sequence is conveniently synthesized on a Fmoc Rink amide solid support resin (Bachem) using Fmoc chemistry on an automated ABI 433 peptide synthesizer (ABD, Perkin Elmer, Foster City, Calif.) according to the manufacturer's standard protocols. Cleavage is typically carried out in 10 ml of thioanisole/EDT/TFA (1/1/9) for 2 hours at room temperature. Crude cleavage product is precipitated with t-butyl methyl ether, filtered and dried.

Formation of disulfide linkages, if desired, is conducted in the presence of mild oxidizing agents. Chemical oxidizing agents may be used, or the compounds may simply be exposed to the oxygen of the air to effect these linkages. Various methods are known in the art. Processes useful for disulfide bond formation have been described by Tam, J. P. et al., *Synthesis* (1979) 955–957; Stewart, J. M. et al., *Solid Phase Peptide Synthesis,* 2d Ed. Pierce Chemical Company Rockford, Ill. (1984); Ahmed A. K. et al., *J Biol Chem* (1975) 250:8477–8482 and Pennington M. W. et al., *Peptides* 1990, E. Giralt et al., ESCOM Leiden, The Netherlands (1991) 164–166. An additional alternative is described by Kamber, B. et al., *Helv Chim Acta* (1980) 63:899–915. A method conducted on solid supports is described by Albericio, *Int J Pept Protein Res* (1985) 26:92–97.

A particularly preferred method is solution oxidation using molecular oxygen. This method has been used by the inventors herein to refold synthetic PG-1, PG-3 in its amide or acid forms, enantio PG-1 and the two unidisulfide PG-1 compounds ($C_6$–$C_{15}$ and $C_8$–$C_{13}$). Recoveries are as high as 65–90%.

In this preferred method to form disulfide linkages, the crude peptide is dissolved in DMSO and added to 20 mM ammonium acetate buffer, pH 7. The final concentration of the peptide in the solution is between 1–8 mg/ml, the pH ranges from 7.0–7.2, and the DMSO concentration ranges from 5–20%. The peptide solution is stirred overnight at room temperature.

The pH of the solution is adjusted to pH5 with concentrated acetic acid and the sample purified on Prep LC. After loading, the column is washed with 10% acetonitrile/$H_2O$ (0.1% TFA) until the UV absorbance decreases to the baseline. The gradient is then started.

Column: Vydac Cat#218TP101522, 2.2×25 cm, $C_{18}$ peptides & proteins; UVX: 235 nm; Flow Rate: 10 ml/min.

Solvent A is 100% 0.1% TFA/$H_2O$; Solvent B is 100% 0.08% TFA/ACN. The gradient is as follows.

| T (min) | % B (linear gradient) |
| --- | --- |
| 0 | 10 |
| 10 | 18 |
| 80 | 32 |
| 95 | 95 |

Fractions are analyzed by analytical HPLC and those that contain the desired peptide are combined. The acetonitrile is stripped and the resulting aqueous solution lyophilized. The resulting amide, containing sulfide bonds, is confirmed by mass spectrum.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Recombinantly produced forms of the protegrins may require subsequent derivatization to modify the N- and/or C-terminus and, depending on the isolation procedure, to effect the formation of disulfide bonds as described hereinabove. Depending on the host organism used for recombinant production and the animal source from which the protein is isolated, some or all of these conversions may already have been effected.

For recombinant production, the DNA encoding the protegrins of the invention is included in an expression system which places these coding sequences under control of a suitable promoter and other control sequences compatible with an intended host cell. Types of host cells available span almost the entire range of the plant and animal kingdoms. Thus, the protegrins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-á-vis these infective agents.

The protegrins of the invention can be produced in a form that will result in their secretion from the host cell by fusing to the DNA encoding the protegrin, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the protegrins of the invention can be produced in a variety of modalities including chemical synthesis and recombinant production or some combination of these techniques.

Any members of the protegrin class which occur naturally are supplied in purified and/or isolated form. By "purified and/or isolated" is meant free from the environment in which the peptide normally occurs (in the case of such naturally occurring peptides) and in a form where it can be used practically. Thus, "purified and/or isolated" form means that the peptide is substantially pure, i.e., more than 90% pure, preferably more than 95% pure and more preferably more than 99% pure or is in a completely different context such as that of a pharmaceutical preparation.

6.2.3 Antibodies

Antibodies to the protegrins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The protegrins of the invention in immunogenic form are then injected into a suitable mammalian host and antibody titers in the serum are monitored. It should be noted, however, that some forms of the protegrins require modification before they are able to raise antibodies, due to their resistance to antigen processing. For example, the native form of PG-1, containing two disulfide bridges is nonimmunogenic when administered without coupling to a larger carrier and was a poor immunogen even in the presence of potent adjuvants and when coupled through glutaraldehyde or to KLH. Applicants believe this to be due to its resistance to attack by leukocyte serine proteases (human PMN elastase and cathepsin G) as well as to attack by an aspartic protease (pepsin) that resembles several macrophage cathepsins. The lack of immunogenicity may therefore result from resistance to processing to a linear form that can fit in the antigen-presenting pocket of the presenting cell. Immunogenicity of these forms of the protegrins can be enhanced by cleaving the disulfide bonds. However, the immunogenicity can be enhanced using the MAPS technique recently reported by Huang, W et al., *Mol Immunol* (1994) 15:1191–1199.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies.

Recombinant techniques are also available for the production of antibodies, and thus, the antibodies of the invention include those that can be made by genetic engineering techniques. For example, single-chain forms, such as $F_v$ forms, chimeric antibodies, and antibodies modified to mimic those of a particular species, such as humans, can be produced using standard methods. Thus, the antibodies of the invention can be prepared by isolating or modifying the genes encoding the desired antibodies and producing these through expression in recombinant host cells, such as CHO cells.

The antibodies of the invention are, of course, useful in immunoassays for determining the amount or presence of the protegrins. Such assays are essential in quality controlled production of compositions containing the protegrins of the invention. In addition, the antibodies can be used to assess the efficacy of recombinant production of the protegrins, as well as screening expression libraries for the presence of protegrin encoding genes.

6.2.4 Compositions Containing the Protegrins and Methods of Use

The protegrins of the invention are effective in inactivating a wide range of microbial and viral targets, including Gram-positive and Gram-negative bacteria, yeast, protozoa and certain strains of virus. Because of their broad spectrum of activities, the protegrins of the invention can be used as preservatives as well as in treatment and prophylactic contexts.

They are bactericidal against Gram-positive bacteria which include major pathogens, such as *Staphylococcus aureus*, including MRSA (the methicillin resistant version) and MSSA (the methicillin-sensitive strain), and *Enterococcus faecium* and *E. faecalis* (including VREF or vancomycin resistant *E. faecium*) and VSEF or vancomycin-sensitive *E. faecalis*). These are very common pathogens in hospital settings. Other Gram-positive bacteria which are suitable targets include *Listeria monocytogenes, Streptococcus pneumoniae* (including PRSP, the penicillin resistant form), *S. mitis, S. sanguis, Staphylococcus epidermis* (including methicillin sensitive strain MSSE), *S. salivarius, Corynebacterium minutissium, C. pseudodiphtheriae, C. striatum,* Corynebacterium groups G1 and G2, and *Bacillus subtilis*. PRSP is also a wide-spread health hazard.

Among Gram-negative organisms against which the protegrins are effective are *Escherichia coli, Pseudomonas aeruginosa, Klebsiella pneumoniae, Serratia marcescens, Haemophilus influenzae, Salmonella typhimurium, Acinetobacter calocoaceticus, C. pneumoniae,* and *Neisseria meningitidus,* as well as other species including those within the genera represented above. For example, *Neisseria gonorrhoeae* is associated with sexually transmitted diseases (STDS) as is *Chlamydia trachomatis*. Also among the Gram-negative organisms are the gastric pathogens *Helicobacter pylori, H. felis,* and *Campylobacter jejuni*.

Besides Gram-positive and Gram-negative bacteria, the protegrins of the invention are also effective against growth and infection by mycobacteria such as *M. tuberculosis* and

*M. avium* (including MAC); fungi, such as *Candida albicans* and the related pathogens, *C. parapsilosis, C. krusei, C. tropicalis* and *C. glabrata,* as well as *Aspergillus niger.* Among the viruses against which the protegrins are effective are Herpes simplex I and II and Human immunodeficiency virus (HIV).

The foregoing is not an exhaustive, but representative list.

As stated above, the protegrins can also be used in disinfectant compositions and as preservatives for materials such as foodstuffs, cosmetics, medicaments, or other materials containing nutrients for organisms. For use in such contexts, the protegrins are supplied either as a single protegrin, in admixture with several other protegrins, or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the protegrins of the invention can be formulated as pharmaceutical or veterinary compositions. Depending on the subject to be treated, the mode of administration, and the type of treatment desired—e.g., prevention, prophylaxis, therapy; the protegrins are formulated in ways consonant with these parameters. A summary of such techniques is found in Remington's *Pharmaceutical Sciences,* latest edition, Mack Publishing Co., Easton, Pa.

The protegrins can be used in animal subjects both as therapeutic and prophylactic treatments; by "treating" an infection is meant either preventing it from occurring, ameliorating the symptoms, inhibiting the growth of the microbe in the subject, and any other negative effect on the microbe which is beneficial to the subject. Thus, "treating" or "treatment" have both prophylactic and therapeutic aspects.

The protegrins are particularly attractive as an active ingredient in pharmaceutical compositions useful in treatment of sexually transmitted diseases, including those caused by *Chlamydia trachomatis, Treponema pallidum, Neisseria gonorrhoeae, Trichomonas vaginalis,* Herpes simplex type 2 and HIV. Topical formulations are preferred and include creams, salves, oils, powders, gels and the like. Suitable topical excipients are well known in the art and can be adapted for particular uses by those of ordinary skill.

In general, for use in therapy or prophylaxis of STDs, the protegrins of the invention may be used alone or in combination with other antibiotics such as erythromycin, tetracycline, macrolides, for example azithromycin and the cephalosporins. Depending on the mode of administration, the protegrins will be formulated into suitable compositions to permit facile delivery to the affected areas. The protegrins may be used in forms containing one or two disulfide bridges or may be in linear form. In addition, use of the enantiomeric forms containing all D-amino acids may confer advantages such as resistance to those proteases, such as trypsin and chymotrypsin, to which the protegrins containing L-amino acids are less resistant.

The protegrins of the invention can be administered singly or as mixtures of several protegrins or in combination with other pharmaceutically active components. The formulations may be prepared in a manner suitable for systemic administration or topical or local administration. Systemic formulations include those designed for injection (e.g., intramuscular, intravenous, intraperitoneal or subcutaneous injection) or may be prepared for transdermal, transmucosal, or oral administration. The formulation will generally include a diluent as well as, in some cases, adjuvants, buffers, preservatives and the like. The protegrins can be administered also in liposomal compositions or as microemulsions.

If administration is to be oral, the protegrins of the invention should be protected from degradation in the digestive tract using a suitable enteric coating. This may be avoided to some extent by utilizing amino acids in the D-configuration, thus providing resistance to protease. The protegrins are relatively acid stable, however, some degree of enteric coating may still be required.

The protegrins of the invention retain their activity against microbes in the context of borate solutions that are commonly used in eye care products. It has also been shown that when tested for antimicrobial activity against *E. coli* in the presence and absence of lysozyme in borate buffered saline, that the presence of lysozyme enhanced the effectiveness of PG-3. This effect was more pronounced when the PG-3 was autoclaved and similar patterns were obtained for both the free-acid form and the amide. Accordingly, the protegrins may be used as preservatives in such compositions or as antimicrobials for treatment of eye infections, such as conjunctivitis and corneal ulcers.

It is particularly important that the protegrins retain their activity under physiological conditions including relatively high salt and in the presence of serum. In addition, the protegrins are dramatically less cytotoxic with respect to the cells of higher organisms as compared with their toxicity to microbes. These properties, described hereinbelow in the Examples, make them particularly suitable for in vivo and therapeutic use.

As the examples will show, by appropriately choosing the member of the protegrin class of the invention, it is possible to adapt the antimicrobial activity to maximize its effectiveness with respect to a particular target microbe. As used herein, "microbe" will be used to include not only yeast, bacteria, and other unicellular organisms, but also viruses. For example, PC-19 is particularly effective, as compared to PG-1, under certain conditions. The particular protegrin can also be chosen to be advantageous in a particular context, such as low salt or physiological salt, the presence or human serum, or conditions that mimic the conditions found in blood and tissue fluids.

The protegrins of the invention may also be applied to plants or to their environment to prevent virus- and microbe-induced diseases in these plants. Suitable compositions for this use will typically contain a diluent as well as a spreading agent or other ancillary agreements beneficial to the plant or to the environment.

Thus, the protegrins of the invention may be used in any context wherein an antimicrobial and/or antiviral action is required. This use may be an entirely in vitro use, or the peptides may be administered to organisms.

In addition, the antimicrobial or antiviral activity may be generated in situ by administering an expression system suitable for the production of the protegrins of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

The protegrins are also capable of inactivating endotoxins derived from Gram-negative bacteria—i.e., lipopolysaccharides (LPS)—in standard assays. Accordingly, the protegrins may be used under any circumstances where inactivation of LPS is desired. One such situation is in the treatment or amelioration of Gram-negative sepsis.

6.2.5 Conditions Relevant to Antimicrobial/Antiviral Activity

It has been stated above that as used herein "antimicrobial" activity refers to inhibition with respect both to traditional microorganisms and to viruses, although occasionally, "antimicrobial" and "antiviral" are both specifically indicated.

A particularly useful property of the protegrins is their activity in the presence of serum. Unlike defensins, protegrins are capable of exerting their antimicrobial effects in the presence of serum.

Media for testing antimicrobial activity can be designed to mimic certain specific conditions. The standard buffer medium, medium A, uses an underlay agar with the following composition: 0.3 mg/ml of trypticase soy broth powder, 1% w/v agarose and 10 mM sodium phosphate buffer (final pH 7.4). This will be designated either "medium A" or "standard in vitro conditions" herein.

All of the remaining media contain these same components. However, in addition:

A second medium contains 100 mM NaCl in order to mimic the salt levels in blood and tissue fluids. This will be designated "medium B" or "salt medium" herein.

A third medium is supplemented with 2.5% normal human serum; however, it is of low ionic strength and thus does not mimic body fluids. This medium will be designated "medium C" or "serum-containing medium" herein.

A fourth medium contains 80% RPMI-1640, a standard tissue culture medium which contains the principal ions and amino acids found in blood and tissue fluids. In addition, it contains 2.5% normal human serum. This will be designated "medium D" or "physiological medium" herein.

Other media useful for testing antimicrobial properties are provided in the Examples.

6.2.6 Specific Indications

Certain of the protegrins of the invention have been found to be particularly effective in treating certain indications. For example, in treating microbial infections where the infectious agent is *Staphylococcus aureus*, particularly methicillin resistant strains, applicants have found the amides of the formulae:

```
RGWRLCYCRPRFCVCVGR        (SEQ ID NO:139)
GWRLCYCRPRFCVCVGR         (SEQ ID NO:141)
XCYCRRRFCVCVGR (X = Cha)  (SEQ ID NO:164)
WLCYCRRRFCVCV             (SQE ID NO:180)
``` to be particularly effective. Also preferred is the free-acid form of WLCYCRRRFCVCV (SEQ ID NO:180).

In treating Pseudomonas infection, applicants have found the following amides to be effective:

```
RGGRLCYCRRRFCVCVGR        (SEQ ID NO:1)
RGGRLCYCRPRFCVCVGR        (SEQ ID NO:239)
RGGGLCYTRPRFTVCVGR        (SEQ ID NO:228)
```

Also effective is the free-acid form of the peptide RLCYCRRRFCVCV (SEQ ID NO:66).

Finally, in treating infections caused by *H. pylori*, applicants have found the following compounds in the amide form to be particularly effective:

```
WLCYCRRRFCVCV              (SEQ ID NO:180)
RXCFCRPRFCVCV (X = Cha)    (SEQ ID NO:178)
RGGRLCYCRRRFCVCVGR         (SEQ ID NO:1)
RGWGLCYCRPRFCVCVGR         (SEQ ID NO:134)
RLCYCRPRFCVCVGR            (SEQ ID NO:138)
RGWRLCYCRGRFCVCVGR         (SEQ ID NO:136)
RGRVCLRYCRGRFCVRLCFR       (SEQ ID NO:241)
RGLRXCYCRGRFCVCVGR (X = Cha) (SEQ ID NO:149)
GWRLCYCRPRFCVCVGR          (SEQ ID NO:139)
RLCYCRRRFCVCV              (SEQ ID NO:66)
WLCYCXXXFCVCV (X = Dab)    (SEQ ID NO:29)
OWRLCYCRPKFCVCV            (SEQ ID NO:33)
RWOLCYCRPKFCVCV            (SEQ ID NO:37)
RRCYCRRRFCVCVGR            (SEQ ID NO:82)
XCYCRRRFCVCV (X = Cha)     (SEQ ID NO:164)
```

Also effective are the free-acid and enantio (all-D) forms of the peptide RRRLCYCRRRFCVCVGR (SEQ ID NO:240).

6.3 Effective Dosages

The peptides of the invention, or compositions thereof, will generally be used in an amount effective to achieve the intended purpose. Of course, it is to be understood that the amount used will depend on the particular application.

For example, for use as a disinfectant or preservative, an antimicrobially effective amount of a peptide, or composition thereof, is applied or added to the material to be disinfected or preserved. By antimicrobially effective amount is meant an amount of peptide or composition that inhibits the growth of, or is lethal to, a target microbe population. While the actual antimicrobially effective amount will depend on a particular application, for use as a disinfectant or preservative the peptides, or compositions thereof, are usually added or applied to the material to be disinfected or preserved in relatively low amounts. Typically, the peptide comprises less than about 5% by weight of the disinfectant solution or material to be preserved, preferably less than about 1% by weight and more preferably less than about 0.1% by weight. An ordinarily skilled artisan will be able to determine antimicrobially effective amounts of particular peptides for particular applications without undue experimentation using, for example, the in vitro assays provided in the examples.

For use to treat or prevent microbial infections or diseases related thereto, the peptides of the invention, or compositions thereof, are administered or applied in a therapeutically effective amount. By therapeutically effective amount is meant an amount effective top ameliorate the symptoms of, or ameliorate, treat or prevent microbial infections or diseases related thereto. Determination of a therapeutically effective amount is well within the capabilities of those skilled in the art, especially in light of the detailed disclosure provided herein.

As in the case of disinfectants and preservatives, for topical administration to treat or prevent bacterial, yeast, fungal or other infections a therapeutically effective dose can be determined using, for example, the in vitro assays provided in the examples. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating peptide concentration range that includes the $IC_{50}$ as determined in cell culture (i.e., the concentration of test compound that is lethal to 50% of a cell culture), the MIC, as determined in cell culture (i.e., the minimal inhibitory concentration for growth) or the $IC_{100}$ as determined in cell culture (i.e., the concentration of peptide that is lethal to 100% of a cell culture). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the active peptide which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of peptide may not be related to plasma concentration. One having skill in the art will be able to optimize therapeutically effective local dosages without undue experimentation.

The amount of peptide administered will, of course, be dependent on the subject being treated, on the subject's weight, the severity of the affliction, the manner of administration and the judgment of the prescribing physician.

The antimicrobial therapy may be repeated intermittently while infections are detectable or even when they are not detectable. The therapy may be provided alone or in combination with other drugs, such as for example antibiotics or other antimicrobial peptides.

6.4 Toxicity

Preferably, a therapeutically effective dose of the peptides described herein will provide therapeutic benefit without causing substantial toxicity.

Toxicity of the peptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the peptides described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1).

Summary

The protegrins therefore represent a peculiarly useful class of compounds because of the following properties:

1) They have an antimicrobial effect with respect to a broad spectrum of target microbial systems, including viruses, including retroviruses, bacteria, fungi, yeast and protozoa.
2) Their antimicrobial activity is effective under physiological conditions—i.e., physiological saline and in the presence of serum.
3) They are markedly less toxic to the cells of higher organisms than to microbes.
4) They can be prepared in nonimmunogenic form thus extending the number of species to which they can be administered.
5) They can be prepared in forms which are resistant to certain proteases suggesting they are antimicrobial even in lysosomes.
6) They can be modified in amino acid sequence so as to optimize the specificity with respect to target.
7) They can be modified structurally so as to accommodate the conditions under which antimicrobial activity is to be exhibited.

The following examples are intended to illustrate but not to limit the invention.

EXAMPLE 1

Isolation and Activity of PG-1, PG-2 and PG-3

As described in PCT/US94/08305, referenced above, three antimicrobial peptides were isolated from porcine leukocytes having the amino acid sequences:

PG-1: RGGRLCYCRRRFCVCVGR

PG-2: RGGRLCYCRRRFCICV

PG-3: RGGGLCYCRRRFCVCVGR, which are amidated at the C-terminus.

These particular protegrins were tested for antimicrobial activity.

It was shown that PG-1 and PG-3 are more effective against *E. coli* ML-35P than human neutrophil peptide HNP-1 and only slightly less effective than rabbit defensin NP-1. PG-1 and PG-3 were also effective against *Listeria monocytogenes*, strain EGD and against *Candida albicans*. In general, these peptides are approximately as effective as rabbit defensin NP-1 on a weight basis and are more effective than HNP-1. In all cases, PG-2 was also effective against the three organisms tested, but was not as active as the other two peptides.

PG-1 has also been shown directly to inhibit the growth of *Staphylococcus aureus* and *K. pneumoneae* 270. HNP-1 used as a control was less effective against *S. aureus* and almost entirely ineffective against *K. pneumoneae*.

The protegrins have also been tested against various other organisms and show broad spectrum activity. In addition to their effectiveness in inhibiting the growth of or infection by microorganisms associated with STDs, the protegrins show strong activity against the following microorganisms in addition to those tested hereinabove: *Pseudomonas aeruginosa, Klebsiella pneumoniae, Salmonella typhimurium, Staphylococcus aureus, Histoplasma capsulatum, Myobacterium avium-intracellulare,* and *Mycobacterium tuberculosis*. The protegrins showed only fair activity against *Vibrio vulnificus* and were inactive against *Vibrio cholerae* and *Borrelia burgdorferi*.

The three protegrins described above retain their activity in the contexts of a variety of reaction conditions, including the presence of 100 mM NaCl and the presence of 90% fetal calf serum.

The protegrins have a spectrum of retention of antimicrobial properties under useful physiological conditions, including isotonic and borate solutions appropriate for use in eye care products.

PG-1 and PG-3 retain their activity with respect to C. albicans and E. coli respectively, in the presence of 100 mM NaCl. Neither NP-1 nor HNP-1 have this property. Although NP-1 and NHP-2 lose their ability to inhibit C. albicans in 90% fetal calf serum, inhibition by PG-3 is retained.

The protegrins show varying patterns of activity when reaction conditions are altered. Synthetic PG-1 was tested against E. coli ML-35 (serum sensitive) in underlayered gels containing only 10 mM sodium phosphate buffer, pH 7.4 and a 1:100 dilution of trypticase soy broth, both in the presence and absence of 2.5% normal human serum, which is below the lytic concentration for this strain of E. coli. In the presence of serum, the minimal bactericidal concentration was reduced from approximately 1.0 $\mu$g/ml to about 0.1 $\mu$g/ml. This type of effect was not observed either for a linear fragment of cathepsin G or for the defensin HNP-1.

Similarly, using C. albicans as a target organism, underlayers were prepared with 10 mM sodium phosphate with and without 10% normal human serum. The minimal fungicidal concentration fell from about 1.3 $\mu$g/ml in the absence of serum to 0.14 $\mu$g/ml in its presence. The serum itself at this concentration did not effect C. albicans. Similar results were obtained using L. monocytogenes as the target organism.

The protegrins PG-1 and PG-3 were incubated for 4 hours at pH 2.0 with 0.5 $\mu$g/ml pepsin and then neutralized. The residual antimicrobial activity against C. albicans, E. coli and L. monocytogenes was assessed and found to be fully retained. Similar experiments show that these compounds are not degraded by human leukocyte elastase or by human leukocyte cathepsin G even when exposed to high concentrations of these enzymes and at a pH of 7.0–8.0 favorable for proteolytic activity. In addition, synthetic PG-3 amide and synthetic PG-3 acid were autoclaved and tested for antimicrobial activity against E. coli, L. monocytogenes and C. albicans, retaining full antimicrobial activity in all cases. It is possible that the stability of these compounds to protease degradation and to autoclaving is enhanced by the presence of disulfide bonds.

The protegrins were also tested for their ability to bind the lipid polysaccharide (LPS) of the Gram-negative bacterium E. coil strain 0.55B5.

Both synthetic and native PG-1, PG-2 and PG-3 in the amidated and nonamidated forms are able to bind LPS at concentrations as low as 2.5 $\mu$g/0.2 ml. nPG-1 and nPG-2 are effective at somewhat lower concentrations. The protegrins were substantially more effective than the NP or HNP test compounds; the most effective among these controls was NP-3a, a peptide whose primary sequence most closely resembles that of the protegrins.

Inhibition of gelation can be overcome by increasing the concentration of LPS, therefore interaction with LPS is responsible for the lack of gelation, rather than interfering with the gelation enzyme cascade.

nPG-1 and nPG-3 were converted to linear form using a reducing agent to convert the disulfide linkages to sulfhydryl groups, which were then stabilized by alkylating with iodoacetamide.

The linearalized forms of the protegrins are equal to cyclic forms in inhibiting gelation in the endotoxin assay and in binding to endotoxin.

Both linearalized and cyclic forms of the protegrins tested continue to show antimicrobial activity, although the effectiveness of these peptides as antimicrobials depends on the nature of the target organism and on the test conditions.

The antimicrobial activity of cyclic and linearalized PG-1 and PG-3 in the concentration range 20 $\mu$g/ml–125 $\mu$g/ml with respect to E. coli ML-35P was measured with and without 100 mM NaCl. The linear form was slightly more potent in the presence of buffer alone than was the cyclic form; on the other hand, the cyclic form was more potent than the linear form under isotonic conditions.

For L. monocytogenes, both cyclic and linearalized forms of the protegrins showed strong antimicrobial activity in the absence of salt and both were approximately equally effective over the concentration range tested (20 $\mu$g/ml–125 $\mu$g/ml). The cyclic form retained strong antimicrobial activity in 100 mM NaCl with a slightly greater concentration dependence. Linearization appeared to lower the activity appreciably although high concentrations were still able to show an antimicrobial effect.

All forms of these protegrins were effective against C. albicans in a dose-dependent manner over the above concentration range when tested in the presence of 10 mM phosphate buffer alone, although the linearalized peptides were very slightly less effective. While the cyclized forms retained approximately the same level of antimicrobial effect in 100 mM NaCl, the activity of the linearalized forms was greatly diminished so that at concentrations below 100 $\mu$g/ml of the protegrin, virtually no antimicrobial effect was seen. At higher concentrations of 130 $\mu$g/ml, a moderate antimicrobial effect was observed.

Thus, depending on the target microorganism and the conditions used, both the cyclized and linearalized forms of the PG-1 and PG-3 have antimicrobial activity.

Contact lens solutions are typically formulated with borate buffered physiological saline and may or may not contain EDTA in addition. Protegrins in the form of the synthetic PG-3 amide and synthetic PG acid were tested wherein underlay gels contain 25 mM borate buffer, pH 7.4, 1% (v/v) tryptocase soy broth (0.3 $\mu$g/ml TSB powder) and 1% agarose. Additions included either 100 mM NaCl, 1 mM EDTA or a combination thereof. Other test compounds used as controls were the defensin NP-1 and lysozyme. Dose response curves were determined.

Although these protegrins are somewhat less active in 25 mM borate buffered saline than in 25 mM phosphate buffer, the antimicrobial activity is enhanced by adding physiological saline and modestly enhanced by 1 mM EDTA.

Tests with C. albicans and with L. monocytogenes indicate that the protegrins are capable of exerting their antimicrobial effects under conditions typically associated with conditions suitable for eye care products.

EXAMPLE 2

Recovery of cDNA Clones

As described in WO 95/03325 referenced above, cDNAs encoding PG-1, PG-2, PG-3 and PG-4 were prepared from porcine leukocytes and the DNA sequences encoding these protegrins are set forth in FIG. 7 of the published application.

EXAMPLE 3

Recovery of Genomic DNA Encoding PG-1, PG-3, and PG-5

High molecular weight genomic DNA was purified from pig white blood cells with the QIAGEN blood DNA kit (QIAGEN, Chatsworth, Calif.). To amplify protegrin (PG) genes, PCR as performed using genomic DNA as a template.

The sense primer (5'-GTCGGAATTCATGGAGACCCAGAG(A or G)GCCAG-3') corresponded to the 5' regions of PG cDNAs, of Example 2 and provided an EcoRI restriction site. The anti-sense primer (5'-GTCGTCTAGA(C or G)GTTTCACAAGAATTTATTT-3') was complementary to 3' ends of PG cDNAs immediately preceding their poly(A) tails and provided an XbaI restriction site. The reaction was carried out in a total volume of 50 μl, which contained 200 ng of purified pig genomic DNA, 25 pmoles of each primer, 1 μg of 10 mM DNTP, 5 μg of 10× PCR buffer (200 mM Tris-HCl, 100 mM($NH_4$)$_2$, 20 mM $MgSO_4$, 1% Triton X-100, 0.1% BSA), and 2.5 units of cloned Pfu DNA polymerase (Stratagene, La Jolla, Calif.). Thirty cycles were performed, each with 1 min of denaturation at 94° C., 1 min of primer annealing at 55° C., 2 min of primer extension at 72° C., and a final extension step at 72° C. for 10 min.

The amplified PCR product was digested with EcoRI and XbaI, excised from the agarose gel, purified, and ligated into pBluescript KS+ vector (Stratagene, La Jolla, Calif.) that had been digested with EcoRI and XbaI and purified. Both strands of DNA were sequenced by the dideoxy method using the Sequenase version 2.0 kit (United States Biochemical, Cleveland, Ohio), pBluescript universal primers and specific oligomer primers based on PG genomic and cDNA sequences. Computer analysis of the DNA sequences was performed using the PC-Gene Program (Intelligenetics, Palo Alto, Calif.).

A PCR product of about 1.85 kb was confirmed as protegrin-related by hybridization with a protegrin-specific oligonucleotide probe complementary to nt 403–429 of the protegrin cDNA sequences. The PCR product was then subcloned into pBluescript vector, and recombinant plasmids were subjected to DNA purification and sequencing. Gene sequences for three different protegrins were identified PG-1, PG-3 and PG-5. The nucleotide sequences and deduced amino acid sequences are shown in FIG. 1.

Comparison of protegrin cDNAs and genes revealed that the coding regions of protegrin genes consisted of four exons, interrupted by three introns (FIG. 2). The first exon contained the 5' noncoding region and codons for the first 66 amino acids of the protegrin prepropeptide, including a 29 residue signal peptide and the first 37 cathelin residues. Exons II and III were relatively small, only 108 and 72 bp respectively, and together contained the next 60 cathelin residues. The final two cathelin residues were on Exon IV, and were followed by the protegrin sequences. The exon-intron splice site sequences are shown in Table 1, and conform to the consensus rule: all introns end on an AG doublet, preceded by a T/C rich stretch of 8–12 bases, while all introns start with GT, followed predominantly by A/G A/G G sequence.

TABLE 1

Exon-Intron Structure of the PG-1 Gene

| Exon | Size | 5' splice donor | Intron | Size | 3' splice acceptor |
|---|---|---|---|---|---|
| 1 | ? + 198 | AAGGCCgtgagtcg | 1 | 405 | ttgaccagGACGAG |
| 2 | 108 | AACGGGgtgaggct | 2 | 152 | ccttccagCGGGTG |
| 3 | 72 | AATGAGgtgagtgg | 3 | 596 | ggtcacagGTTCAA |
| 4 | 313 | | | | |

The highly conserved cathelin region spans exons I–IV and Exon IV contains the full sequence of the mature protegrin peptide followed by an amidation consensus sequence, a 3' untranslated region, and the putative poly-adenylation site. The three introns range in size from 152 to 596 bp. If the protegrin genes are representative of other cathelin-like genes, the third intron of cathelin-associated peptides will be found to separate all but the last two residues of the highly conserved cathelin region from the variable antimicrobial peptides encoded in Exon IV. Such a layout would favor recombination mechanisms involving association of diverse Exon IVs with the first three exons specifying cathelin containing prepro-regions.

The family of naturally occurring protegrins thus contains at least 5 members. FIG. 5 shows a comparison of the amino acid sequences of the five protegrins found so far in porcine leukocytes. There is complete homology in positions 1–3, 5–9, 13 and 15–16.

Homology search of protegrin genes against the EMBL/GenBank identified no significantly homologous genes. More specifically, the gene structures and nucleotide sequences of protegrins were very different from those of defensins, which contain three exons in myeloid defensin genes, and two exons in enteric defensin genes. As expected, the search yielded the large family of cDNAs corresponding to cathelin-associated bovine, porcine and rabbit leukocyte peptides.

To assess protegrin-related genes further, we screened a porcine genomic library of approximately $2.3 \times 10^5$ clones in EMBL-3 SP6/T7 with the $^{32}$P-labeled protegrin cDNA, and identified 45 hybridizing clones.

A porcine liver genomic library in EMBL3 SP6/T7 phages was purchased from Clontech (Palo Alto, Calif.). E. coli strain K803 was used as a host, and DNA from phage plaques was transferred onto nylon membranes (DuPont, Boston, Mass.). The filters were hybridized with $^{32}$P-labeled porcine 691 PG-3 cDNA. The filters were washed several times, finally at 60° C. in 0.1× SSC and 0.1% SDS, and exposed to x-ray film with an intensifying screen at −70° C. Positive clones were subjected to two additional rounds of plaque purification at low density.

DNA purified from hybridizing clones was digested with various restriction endonucleases (New England Biolabs, Beverly, Mass.), fractionated on 0.8% agarose gels, and transferred onto GeneScreen Plus membrane (DuPont, Boston, Mass.). The hybridization probes were labeled with $^{32}$P and included porcine PG-3 cDNA, and 5'-labeled protegrin-specific oligonucleotide complementary to nt 403–429 of PG-1, 2 and 3 cDNAs. For the cDNA probe, the hybridization and washing conditions were carried out as for the library screening. For the oligonucleotide probe, the membranes were washed at 42° C. in 0.1× SSC, 0.1% SDS.

Southern blot analysis was carried out with purified DNA from positive clones by hybridization with protegrin CDNA and a protegrin specific oligonucleotide complementary to nt 403–429 of protegrin CDNA sequences. Although all of the clones hybridized with the complete cDNA probe, only about half of them hybridized with the protegrin-specific probe. A specific oligonucleotide probe for porcine prophenin, another cathelin-associated porcine leukocyte-derived antimicrobial peptide, hybridized to several of the nonprotegrin clones. These results confirm a) that the conserved proregion homologous to cathelin is present within the same gene as the mature antimicrobial peptides and is not added on by posttranscriptional events, and b) that the protegrins account for about half of the cathelin-related genes in the pig.

A synthetic peptide corresponding to the amino acid sequence of PG-5 was prepared and tested with respect to antimicrobial activity against E. coli, L. monocytogenes and C. albicans. The results were compared to those obtained with a synthetically prepared PG-1. The results are shown in FIGS. 3a–3c. As shown in these graphical representations of the results, PG-5 has comparable antimicrobial activity to PG-1 against all three organisms tested.

EXAMPLE 4

Preparation of EnantioPG-1

Using standard solid phase techniques, a protegrin having the amino acid sequence of PG-1, but wherein every amino acid is in the D form was prepared. This form of protegrin was tested against *E. coli, L. monocytogenes, C. albicans* and other microbes in the absence and presence of protease and otherwise as described for the radiodiffusion assay in agarose gels, generally as described by Lehrer, R. I. et al. *J Immunol Meth* (1991) 137:167–173. The results show that both native PG-1 and enantio PG-1 in the absence of protease are equally effective in inhibiting the growth of *E. coli*. Neither trypsin nor chymotrypsin inhibits the antibacterial effect of enantio PG-1. In the presence of these proteolytic enzymes, the ability of native PG-1 to inhibit the growth of *L. monocytogenes* is adversely affected, although in the absence of these proteases PG-1 is comparably active to an enantio PG-1.

Using similar techniques, the enantio forms of PG-2, PG-3, PG-4 and PG-5 are synthesized. Similarly, the enantio forms of the specific compounds set forth herein are prepared.

EXAMPLE 5

Activity of the Protegrins Against STD Pathogens

As reported in WO 95/03325, PG-1 was tested against a variety of organisms which are responsible for the infections associated with sexually transmitted diseases (STDs). PG-1 was highly active against HIV-1, *Chlamydia trachomatis, Treponema pallidum, Neisseria gonorrhoeae,* and was moderately active against *Trichomonas vaginalis* and Herpes simplex type 2. PG-1 appeared inactive against Herpes simplex type 1, however, another protegrin, the amide form of RGGLVYVRGRFCVCVGR, was active against Herpes Simplex virus type 1.

EXAMPLE 6

Antiretroviral Activity

Both synthetic and native PG-1 and native PG-2 showed antiviral activity against various strains of HIV using the method described in Miles, S. A. et al., *Blood* (1991) 78:3200–3208, as set forth in WO 95/03325.

The protegrins show similar activity with respect to other retroviruses.

EXAMPLE 7

Preparation of Modified Protegrins: Kite and Bullet Forms

The kite and bullet forms of PG-1 wherein all Z are alanine were synthesized using conventional Fmoc chemistry. The crude synthetic peptide was reduced by adding dithiothreitol (DTT) equal in weight to the synthetic peptide which had been dissolved at 10 mg peptide/ml in a solution containing 6 molar guanidine HCl, 0.5 molar tris buffer, and 2 mM EDTA, pH 8.05 and incubated for two hours at 52° C. under nitrogen. The mixture was passed through a 0.45 μm filter, acidified with 1/20 (v/v) glacial acetic acid and subjected to conventional RP-HPLC purification with a C-18 column. HPLC-purified, reduced synthetic bullet and kite PG-1 were partially concentrated by vacuum centrifugation in a speed vac and allowed to fold for 24 hours at room temperature in ambient air in 0.1 M Tris pH 7.7 at low concentration (0.1 mg peptide/ml) to minimize formation of interchain disulfide disulfides. The mixture was then concentrated and acidified with HOAC to a final concentration of 5% and subjected to RP-HPLC purification.

The purity of the final products bullet and kite PG-1 was verified by AU-PAGE, analytical HPLC, and FAB-mass spec. AU-PAGE showed a single band for the final product in each case. The observed MH+ mass values were 2093 in both cases.

EXAMPLE 8

Antimicrobial Activity of the Kite and Bullet Forms

The kite and bullet PG-1 compounds prepared in Example 7 were tested for antimicrobial activity using the radial diffusion assay as published by Lehrer, R. I. et al., *J Immunol Meth* (1991) 137:167–173, except that the underlay agars contained 10 mM sodium phosphate buffer with a final pH of 7.4. As described in Example 1, 0.3 mg/ml trypticase soy broth powder and 1% agarose were used as well in the underlay agar. In some cases 100 mM NaCl or RPMI plus 2.5% normal human serum (NHS) was added to the agar.

In a first set of determinations, the bullet and kite forms of PG-1 were tested for antimicrobial activity against *L. monocytogenes, E. faecium* (VR) or *S. aureus* under these three sets of conditions.

The bullet and kite forms were roughly equally effective against these three bacteria using standard assay conditions. When 100 mM NaCl was added to the agar, however, the kite forms appeared slightly less active than the bullet forms which appear to have slightly enhanced antimicrobial activity against all three strains except *S. aureus* under these conditions. Similarly, when RPMI plus 2.5% NHS were added, the bullet forms were again more effective than the kite forms. The activity of the kite form versus *E. faecium* was significantly less under these conditions.

These forms of PG-1 were also tested against *E. coli, K. pneumoniae* and *P. aeruginosa.* All three microorganisms were inhibited by both kite and bullet forms under standard conditions. This antimicrobial activity was maintained also at 100 mM NaCl and RPMI plus NHS.

EXAMPLE 9

Synthesis of the Snake Form of PG-1

The snake form of PG-1 wherein all Z are alanine was performed using standard methods by Synpep Inc., Dublin, Calif. and the MH+ value in FAB-mass spec was 2031.3 as expected. The snake form was purified to homogeneity by RP-HPLC.

EXAMPLE 10

Antimicrobial Activity of Snake PG-1

Snake PG-1 was tested with respect to the same six organisms and using the same conditions as set forth in Example 8 with respect to the bullet and kite forms of PG-1. In this case, the native two-disulfide form of PG-1 (native) was used as a control. While the snake form shows somewhat superior activity with respect to *L. monocytogenes, E. faecium,* and *S. aureus* under standard conditions, it is notably less effective than the native form in the presence of either 100 mM NaCl or RPMI plus NHS. The same pattern is followed when the test organisms are *E. coli, K. pneumoniae,* and *P. aeruginosa.*

EXAMPLE 11

Preparation of Miniprotegrins and Protegrins with Enhanced Basicity

A series of protegrins was prepared, including bullet and kite forms, wherein one or both of $X_5$ and $X_{16}$ is a basic as opposed to a hydrophobic amino acid and/or wherein $X_1$–$X_4$ are absent. The peptides prepared are summarized and compared to the amino acid sequence of PG-1 as shown in Table 2.

TABLE 2

Sequences of Selected Miniprotegrins

| Code | Sequence | Mass |
|---|---|---|
| PG-1 | RGGRLCYCRRRFCVCVGR | 2154.04 |
| PC-11 | LCYCRRRFCVCVGR | 1730.11 |
| PC-12 | RCYCRRRFCVCVGR | 1773.14 |
| PC-13 | RGGRLCYCRRRFCVCV | 1943.35 |
| PC-14 | RGGRLCYCRRRFCICV | 1957.38 |
| PC-15 | RGGRLCYCRRRFCVCR | 2000.41 |
| PC-16 | RCYCRRRFCVCR | 1616.96 |
| PC-17 | LCYCRRRFCVCV | 1516.87 |
| PC-18 | LCYARRRFAVCV | 1454.77 |
| PC-19 | RCYARRRFAVCR | 1554.85 |
| PC-20 | LAYCRRRFCVAV | 1454.77 |
| PC-21 | RAYCRRRFCVAR | 1554.85 |
| PC-22 | RGGRLCY RR VCVGR* | 1648.97 |
| PC-31a | GGRLCYCRRRFCVCVGR | 1999.40 |
| PC-32a | RGRLCYCRRRFCVCVGR | 2098.54 |
| PC-33a | GRLCYCRRRFCVCVGR | 1942.35 |
| PC-34a | RRLCYCRRRFCVCVGR | 2041.49 |
| PC-35a | RLCYCRRRFCVCVGR | 1885.30 |
| PC-36a | RRCYCRRRFCVCVGR | 1928.33 |
| PC-37a | CYCRRRFCVCVGR | 1615.95 |
| PC-44a | RGGRLCYCRRRFCVCR* | 2000.41 |
| PC-45 | RGGRLCYCRRRFCVC | 1843.22 |
| PC-46 | RGGRLCYCRRRFCVC* | 1844.22 |

TABLE 2-continued

Sequences of Selected Miniprotegrins

| Code | Sequence | Mass |
|---|---|---|
| PC-47a | RGGRLCY RRRF VCVGR | 1951.33 |
| PC-48 | RGWRLCYCRRRFCVCVGR | 2284.75 |

The asterisk (*) in TABLE 2 indicates C-terminal free acid; all others are C-terminal amides.

The protegrin congeners were tested using the radial diffusion assay described above using mid-log phase organisms, except that assays with C. albicans used overnight cultures. As described above, all underlay agars contained 0.3 mg/ml trypticase soy broth powder/ml, 1% w/v agarose and 10 mM sodium phosphate buffer, pH 7.4 and were seeded with $4 \times 10^6$ bacterial or fungal CFU/10 ml. The standard underlay agar, medium A, is as described; medium B is identical except that it also contains 100 mM NaCl; medium C contains the standard medium plus 2.5% normal human serum; and medium D contains 80% RPMI-1640 plus 2.5% normal human serum.

The test peptides were dissolved at 500 μg/ml in 0.01% acetic acid and serial dilutions were prepared in the same solvent either as two-fold dilutions or half-log dilutions (half-log dilutions are, from 500 μg/ml, 250, 78, 25, 7.8, 2.5, 0.78, 0.25 and 0.078 μg/ml).

The dilutions were made daily in sufficient amount for that day's experiments; to perform the tests, 5 μg volumes of the solutions were added to prepunched wells (3 mm diameter) in the bacterial underlay gels. Overlay gels (2× conventional trypticase soy agar) were poured after 3 hours. Zone sizes were measured to the nearest 0.1 mm after overnight incubation. Zone sizes in units of clearing (10 units=1 mm diameter) were graphed against $\log_{10}$ of the peptide concentration using the sigma plot program. The X-intercept corresponds to the minimal microbicidal concentration and was determined by least mean squares regression analysis. Only the highest peptide concentration which showed no clearing was included in the calculation.

The results are provided both in terms of minimal microbicidal concentrations in μg/ml and relative molar potency, which corrects for molecular weight.

In the initial experiments, PC-11 and PC-12 were tested in comparison to PG-1. The results are shown in Tables 3 and 4.

TABLE 3

Minimal Microbicidal Concentrations (μg/ml)

| Series 1 | 10 mM Phosphate Buffer | | | 10 mM Buffer + 100 mM NaCl | | |
|---|---|---|---|---|---|---|
| Dilutions Organism | Protegrin PG-1 | PC-11 | PC-12 | Protegrin PG-1 | PC-11 | PC-12 |
| E. coli ML-35p | 5.3 | 2.3 | 3.8 | 2.8 | 1.3 | 1.9 |
| L. mono., EGD | 5.8 | 4.8 | 5.1 | 3.6 | 3.7 | 5.5 |
| C. albicans 820 | 6.1 | 7.1 | 4.3 | 7.9 | 11.6 | 20.5 |
| S. aureus 930918-3 | 7.0 ± 0.54 | 3.7 | 3.3 | 4.5 ± 0.26 | 3.3 | 3.9 |
| MRSA 30371 | n.t. | n.t. | n.t. | 4.0 ± 0.18 | 3.2 | 3.1 |
| MRSA 28841 | n.t. | n.t. | n.t. | 3.1 ± 0.03 | 2.1 | 2.6 |

TABLE 4

Relative Molar Potency (PG-1 = 1.00)

| | 10 mM Phosphate Buffer | | Buffer + 100 mM NaCl | |
|---|---|---|---|---|
| Organism | PC-11 | PC-12 | PC-11 | PC-12 |
| E. coli ML-35p | 1.85 | 1.15 | 1.73 | 1.65 |
| L. mono., EGD | 0.97 | 0.99 | 0.78 | 0.80 |
| C. albicans 820 | 0.69 | 0.71 | 0.55 | 0.47 |
| S. aureus 930918-3 | 1.52 | 1.75 | 1.09 | 0.95 |
| MRSA 30371 | n.t. | n.t. | 1.00 | 1.06 |
| MRSA 28841 | n.t. | n.t. | 1.19 | 0.98 |

As shown in Table 4, the shortened forms of the protegrins are slightly more effective against E. coli and against S. aureus as compared to PG-1 and comparably effective against the remaining organisms tested except for C. albicans where the effectiveness was of the same order of magnitude.

Tables 5 and 6 show the minimal microbicidal concentrations and relative molar potency of an embodiment, PC-15, where $X_{16}$ is a basic amino acid. PC-13, shown in these tables, is identical to PG-1 except that it lacks $X_{17}$ and $X_{18}$. As shown in these tables, replacing $X_{16}$ with a basic amino acid generally enhances the potency against most organisms, but alters the response to the addition of salt.

TABLE 5

Minimal Microbicidal Concentrations (μg/ml)

| Series 1 Dilutions | 10 mM Phosphate Buffer | | | | 10 mM Buffer + 100 mM NaCl | | | |
|---|---|---|---|---|---|---|---|---|
| Organism | PG-1 | PC-13 | PG-2 | PC-15 | PG-1 | PC-13 | PG-2 | PC-15 |
| E. coli ML-35p | 6.1 | 3.4 | 4.7 | 3.7 | 3.4 | 2.3 | 2.9 | 1.5 |
| L. mono., EGD | 6.5 | 4.6 | 5.2 | 2.8 | 4.0 | 2.7 | 3.2 | 2.4 |
| C. albicans 820 | 5.5 | 4.0 | 4.8 | 2.6 | 7.5 | 10.2 | 10.1 | 8.8 |
| E. faecium (clin. isol.) | 10.7 | 6.6 | 10.8 | 4.3 | 2.6 | 3.4 | 4.0 | 6.2 |
| VREF CDC21 (E. faecalis) | n.t. | n.t. | n.t. | n.t. | 3.1 | 4.6 | 3.6 | 5.6 |
| VREF 94.132 (E. faecium) | n.t. | n.t. | n.t. | n.t. | 3.0 | 2.0 | 2.3 | 0.8 |
| S. aureus 930918-3 | 6.0 | 6.1 | 7.5 | 5.3 | 4.7 | 3.4 | 3.6 | 5.7 |
| MRSA 30371 | n.t. | n.t. | n.t. | n.t. | 4.1 | 3.4 | 3.6 | 4.4 |
| MRSA 28841 | n.t. | n.t. | n.t. | n.t. | 3.2 | 2.6 | 2.1 | 2.3 |

TABLE 6

Relative Molar Potency (PG-1 = 1.00)

| | 10 mM Phosphate Buffer | | | 10 mM Buffer + 100 mM NaCl | | |
|---|---|---|---|---|---|---|
| Organism | PC-13 | PG-2 | PC-15 | PC-13 | PG-2 | PC-15 |
| E. coli ML-35p | 1.62 | 1.18 | 1.53 | 1.33 | 1.06 | 2.1 |
| L. mono., EGD | 1.27 | 1.14 | 2.15 | 1.33 | 1.14 | 1.55 |
| C. albicans 820 | 1.24 | 1.04 | 1.96 | 0.66 | 0.67 | 0.79 |
| E. faecium (clin. isol.) | 0.89 | 0.90 | 2.31 | 0.69 | 0.59 | 0.39 |
| VREF CDC21 (E. faecalis) | n.t. | n.t. | n.t. | 0.61 | 0.78 | 0.51 |
| VREF 94.132 (E. faecium) | n.t. | n.t. | n.t. | 1.35 | 1.18 | 3.48 |
| S. aureus 930918-3 | 0.89 | 0.75 | 1.05 | 1.25 | 1.19 | 0.77 |
| MRSA 30371 | n.t. | n.t. | n.t. | 1.09 | 1.03 | 0.86 |
| MRSA 28841 | n.t. | n.t. | n.t. | 1.11 | 1.38 | 0.85 |

TABLE 7

Minimal Microbicidal Concentrations (μg/ml)

| Series 1 Dilutions | 10 mM Phosphate Buffer | | | Buffer + 100 mM NaCl | | |
|---|---|---|---|---|---|---|
| Organism | PG-1 | PC-16 | PC-17 | PG-1 | PC-16 | PC-17 |
| E. coli ML-35p | 4.4 | 1.1 | 2.0 | 3.0 | 0.9 | 2.7 |
| L. mono., EGD | 4.0 | 1.1 | 2.2 | 2.6 | 4.1 | 5.0 |
| C. albicans 820 | 5.2 | 1.9 | 5.5 | 8.0 | 29.3 | 32.6 |
| E. faecium | 6.6 | 3.4 | 4.8 | 3.3 | 3.8 | 5.7 |
| VREF, CDC21 (E. faecalis) | n.t. | n.t. | n.t. | 4.1 | 16.7 | 6.4 |
| VREF, 94.132 (E. faecium) | n.t. | n.t. | n.t. | 3.3 | 1.2 | 3.7 |
| S. aureus 930918-3 | 7.6 | 3.8 | 5.2 | 4.7 | 27.5* | 6.4 |
| MRSA 30371 | n.t. | n.t. | n.t. | 4.3 | 12.3* | 5.7 |
| MRSA 28841 | n.t. | n.t. | n.t. | 3.1 | 3.5* | 4.0 |

Tables 7–10 show results for PC-16 and PC-17, both of which lack $X_1$–$X_4$; PC-16 also contains basic amino acids at positions $X_5$ and $X_{16}$. Tables 8 and 10 relate to minimal microbicidal concentrations and differ only in that the dilution method has been altered. In Tables 8 and 9 two-fold dilutions were used and in Tables 10–11 half-log dilutions were used. The data in these tables show that the effectiveness compared to PG-1 varies with the target organism and with the conditions of testing. As shown in Table 9, for example, PC-17 (and PC-16) are mostly comparatively less active than PG-1 in the presence of salt; as shown in Table 11 the presence of serum is also problematic, especially for PC-16.

TABLE 8

Relative Molar Potency (PG-1 = 1.00)

| Series 1 Dilutions | 10 mM Phosphate Buffer | | Buffer + 100 mM NaCl | |
|---|---|---|---|---|
| Organism | PC-16 | PC-17 | PC-16 | PC-17 |
| E. coli ML-35p | 3.00 | 1.55 | 2.50 | 0.78 |
| L. mono., EGD | 2.73 | 1.28 | 0.48 | 0.37 |
| C. albicans 820 | 2.05 | 0.67 | 0.20 | 0.17 |
| E. faecium | 1.46 | 0.97 | 0.65 | 0.41 |
| VREF, CDC21 (E. faecalis) | n.t. | n.t. | 0.18 | 0.45 |
| VREF, 94.132 (E. faecium) | n.t. | n.t. | 2.06 | 0.63 |
| S. aureus 930918-3 | | | 0.13* | 0.13 |

TABLE 8-continued

Relative Molar Potency (PG-1 = 1.00)

| Series 1 Dilutions | 10 mM Phosphate Buffer | | Buffer + 100 mM NaCl | |
|---|---|---|---|---|
| Organism | PC-16 | PC-17 | PC-16 | PC-17 |
| MRSA 30371 | n.t. | n.t. | 0.26* | 0.26 |
| MRSA 28841 | n.t. | n.t. | 0.66* | 0.55 |

TABLE 9

Minimal Microbicidal Concentrations (μg/ml)

| Series 2 Dilutions | Buffer + 100 mM NaCl | | | RPMI + 2.5% NHS | | |
|---|---|---|---|---|---|---|
| Organism | PG-1 | PC-16 | PC-17 | PG-1 | PC-16 | PC-17 |
| E. coli ML-35p | 1.4 | 0.59* | 1.0 | 0.36 | 0.49 | 0.42 |
| L. mono., EGD | 0.7 | 1.5 | 0.7 | 0.35 | 0.61 | 0.42 |
| C. albicans 820 | 8.6 | 25.5 | 10.5 | 7.1 | 24.1* | 29.8* |
| E. faecium | 1.2 | 10.0 | 0.63 | 0.42 | 31.1 | 0.40 |
| VREF, CDC21 (E. faecalis) | 1.5 | 11.3 | 1.6 | 0.5 | 28.4 | 0.90 |
| VREF, 94.132 (E. faecium) | 0.67 | 0.44 | 0.56 | 0.37 | 8.8 | 0.39 |
| P. aeruginosa MR 2330 | 1.3 | 0.41 | 1.2 | 0.96 | 8.8 | 0.80 |
| P. aeruginosa SBI-N | 1.4 | 1.2 | 1.1 | 0.81 | 2.8 | 0.83 |
| P. aeruginosa MR 3007 | 1.3 | 0.80 | 0.60 | 1.1 | 8.9 | 0.88 |
| P. aeruginosa MR 2133 | 1.4 | 0.85 | 0.59 | 0.91 | 3.9 | 0.81 |
| S. aureus 930918-3 | 3.3 | >250 | 3.9 | 0.44 | 0.82* | 0.35 |
| MRSA 30371 | 1.5 | >250 | 1.6 | 0.32 | 1.0* | 0.30 |
| MRSA 28841 | 1.3 | 7.9* | 1.6 | 0.6 | 9.5 | 0.20 |

TABLE 10

Relative Molar Potency (PG-1 = 1.00)

| Series 2 Dilutions | Buffer + 100 mM NaCl | | RPMI + 2.5% NHS | |
|---|---|---|---|---|
| Organism | PC-16 | PC-17 | PC-16 | PC-17 |
| E. coli ML-35p | 1.78 | 0.99 | 0.35 | 0.60 |
| L. mono., EGD | 0.35 | 0.70 | 0.43 | 0.59 |
| C. albicans 820 | 0.25 | 0.58 | 0.22 | 0.17 |
| E. faecium | 0.09 | 1.34 | 0.01 | 0.74 |
| VREF, CDC21 (E. faecalis) | 0.10 | 0.66 | 0.01 | 0.39 |
| VREF, 94.132 (E. faecium) | 1.14 | 0.84 | 0.03 | 0.67 |
| P. aeruginosa MR 2330 | 2.38 | 0.76 | 0.08 | 0.85 |
| P. aeruginosa SBI-N | 0.88 | 0.90 | 0.22 | 0.69 |
| P. aeruginosa MR 3007 | 1.22 | 1.53 | 0.09 | 0.88 |
| P. aeruginosa MR 2133 | 1.24 | 1.67 | 0.18 | 0.79 |
| S. aureus 930918-3 | <0.03 | 0.60 | 0.40 | 0.89 |
| MRSA 30371 | <0.03 | 0.66 | 0.24 | 0.75 |
| MRSA 28841 | 0.12 | 0.57 | 0.05 | 2.11 |

Tables 11–14 show the results for the kite forms of the invention protegrins. Again, it is apparent that the spectrum of target organisms which are responsive and the spectrum of conditions under which response is obtained are variable. In general, the more cationic form, PC-19 is less effective than the unmodified form which merely lacks the residues $X_1$–$X_4$. Under physiological conditions, PC-19 is substantially inactive.

TABLE 11

Minimal Microbicidal Concentrations (μg/ml)

| Series 1 Dilutions | 10 mM Phosphate Buffer | | | Buffer + 100 mM NaCl | | |
|---|---|---|---|---|---|---|
| Organism | PG-1 | PC-18 | PC-19 | PG-1 | PC-18 | PC-19 |
| E. faecium | 7.7 | 1.7 | 17.7 | 4.2 | 2.9 | >250 |
| VREF, CDC21 (E. faecalis) | n.t. | n.t. | n.t. | 4.6 | 5.3 | >250 |
| VREF 94.132 (E. faecium) | n.t. | n.t. | n.t. | 3.6 | 1.4 | 5.6 |
| S. aureus 930918-3 | 7.3 | 3.9 | 7.3 | 5.0 | 2.1 | 10.4 |
| MRSA 30371 | n.t. | n.t. | n.t. | 4.1 | 6.5 | 68.6 |
| MRSA 28841 | n.t. | n.t. | n.t. | 3.6 | 3.9 | 17.4 |

TABLE 12

Relative Molar Potency (PG-1 = 1.00)

| Series 1 Dilutions | 10 Mm Phosphate Buffer | | Buffer + 100 mM NaCl | |
|---|---|---|---|---|
| Organism | PC-18 | PC-19 | PC-18 | PC-19 |
| E. faecium | 3.06 | 0.31 | 0.98 | 0.01 |
| VREF, CDC21 (E. faecalis) | n.t. | n.t. | 0.59 | 0.01 |
| VREF 94.132 (E. faecium) | n.t. | n.t. | 1.74 | 0.46 |
| S. aureus 930918-3 | 1.26 | 0.72 | 1.61 | 0.35 |
| MRSA 30371 | n.t. | n.t. | 0.43 | 0.04 |
| MRSA 28841 | n.t. | n.t. | 0.62 | 0.15 |

TABLE 13

Minimal Microbicidal Concentrations (μg/ml)

| Series 2 Dilutions | 10 mM Buffer + 100 mM NaCl | | | RPMI + 2.5% NHS | | |
|---|---|---|---|---|---|---|
| Organism | PG-1 | PC-18 | PC-19 | PG-1 | PC-18 | PC-19 |
| E. faecium | 1.5 | 3.2 | >250 | | 2.9 | >250 |
| VREF, CDC21 (E. faecalis) | 1.4 | 3.4 | >250 | | 10.0 | >250 |
| VREF 94.132 (E. faecium) | 0.61 | 0.50 | 2.9 | 0.30 | 1.2 | 30.2 |
| P. aeruginosa MR 2330 | 1.3 | 1.1 | 3.0 | 0.7 | 3.0 | 29.2 |
| P. aeruginosa SBI-N | 1.3 | 1.2 | 2.1 | 0.85 | 4.6 | >250 |
| P. aeruginosa MR 3007 | 1.3 | 1.1 | 1.1 | 0.72 | 3.89 | >250 |
| P. aeruginosa MR 2133 | 1.2 | 2.4 | 2.5 | 0.9 | 3.9 | >250 |

TABLE 14

Relative Molar Potency (PG-1 = 1.00)

| Series 2 Dilutions | 10 mM Buffer + 100 mM NaCl | | RPMI + 2.5% NHS | |
|---|---|---|---|---|
| Organism | PC-18 | PC-19 | PC-18 | PC-19 |
| E. faecium | 0.32 | <0.01 | 0.98 | 0.01 |
| VREF, CDC21 (E. faecalis) | 0.28 | <0.01 | 0.03 | <0.01 |
| VREF 94.132 (E. faecium) | 0.81 | 0.15 | 0.17 | <0.01 |
| P. aeruginosa MR 2330 | 0.8 | 0.31 | 0.16 | 0.02 |

TABLE 14-continued

Relative Molar Potency (PG-1 = 1.00)

| Series 2 Dilutions | 10 mM Buffer + 100 mM NaCl | | RPMI + 2.5% NHS | |
|---|---|---|---|---|
| Organism | PC-18 | PC-19 | PC-18 | PC-19 |
| P. aeruginosa SBI-N | 0.73 | 0.45 | 0.12 | <0.01 |
| P. aeruginosa MR 3007 | 0.80 | 0.85 | 0.13 | <0.01 |
| P. aeruginosa MR 2133 | 0.34 | 0.35 | 0.16 | <0.01 |

Tables 15 and 16 provide results obtained with the kite forms of the invention protegrins. The more cationic forms are generally less effective than PG-1 under conditions of high salt or serum. However, they are comparably effective against *E. coli*.

TABLE 15

Minimal Microbicidal Concentrations (μg/ml)

| Series 1 Dilutions | 10 mM Phosphate Buffer | | | Buffer + 100 mM NaCl | | | Buffer + 2.5% NHS | | |
|---|---|---|---|---|---|---|---|---|---|
| Organism | PG-1 | PC-20 | PC-21 | PG-1 | PC-20 | PC-21 | PG-1 | PC-20 | PC-21 |
| E. coli ML-35 | 4.6 | 0.75 | 0.36 | 2.0 | 1.9 | 1.8 | 0.34 | 0.27 | 0.28 |
| L. mono. EGD | 4.8 | 3.3 | 1.4 | 3.4 | 21.7 | 36.3 | 1.3 | 5.5 | 5.6 |
| C. albicans 820 | 6.1 | 5.3 | 8.5 | 6.8 | 67.5 | >250 | 8.1 | 30.1 | 59.7 |
| E. faecium | 6.7 | 6.7 | 18.0 | 3.9 | 69.0 | >250 | | | |
| VREF, CDC21 (faecalis) | n.t. | n.t. | n.t. | 4.9 | >250 | >250 | | | |
| VREF 94.132 (faecium) | n.t. | n.t. | n.t. | 2.5 | 3.3 | 28.3 | | | |
| S. aureus 930918-3 | 10.3 | 5.8 | 7.2 | 5.1 | 30.3 | 64.6* | | | |
| MRSA 30371 | n.t | n.t. | n.t. | 4.2 | 29.9 | 64.6* | | | |
| MRSA 28841 | n.t. | n.t. | n.t. | 3.3 | 8.4 | 8.4 | | | |

TABLE 16

Relative Molar Potency (PG-1 = 1.00)

| Series 1 Dilutions | 10 mM Phosphate Buffer | | Buffer + 100 mM NaCl | | Buffer + 2.5% NHS | |
|---|---|---|---|---|---|---|
| Organism | PC-20 | PC-21 | PC-20 | PC-21 | PC-20 | PC-21 |
| E. coli ML-35 | 4.14 | 9.21 | 0.71 | 0.8 | 4.50 | 0.88 |
| L. mona. EGD | 0.98 | 2.47 | 0.09 | 0.07 | 0.16 | 0.17 |
| C. albicans 820 | 0.78 | 0.52 | 0.07 | <0.02 | 0.18 | 0.10 |
| E. faecium | 0.68 | 0.27 | 0.03 | 0.01 | | |
| VREF, CDC21 (faecalis) | n.t. | n.t | 0.01 | 0.01 | | |
| VREF 94.132 (faecium) | n.t. | n.t. | 0.20 | 0.06 | | |
| S. aureus 930918-3 | 1.20 | 1.03 | 0.11 | <0.06 | | |
| MRSA 30371 | n.t. | n.t. | 0.09 | <0.05 | | |
| MRSA 28841 | n.t. | n.t. | 0.26 | 0.28 | | |

EXAMPLE 12

Minimal Bioactive Conformation of PG-1 Necessary for Activity Against *Neisseria gonorrhoeae*

The susceptibility of *N. gonorrhoeae* to variants of protegrin PG-1 was determined using the radial diffusion assay of Lehrer et al.,1991, *J Immunol Methods* 137:167. Native protegrin PG-1 was purified for porcine leukocytes by the method of Kokryakov, V. N. et al. (*FEBS Lett* (1993) 327:231–236). All other protegrins were prepared synthetically with F-moc chemistry and purified by reverse phase HPLC.

The following *N. gonorrhoeae* strains were tested: FA19 (sac-1, sac-3; serum-resistant [$SaC^R$]), JS-1 (serum-resistant; sac-1, sac-3; [$SaC^R$]), and F62 (sac-1$^+$, sac-3; serum-sensitive [$Sac^S$]) have been described by Cannon et al. (*Infect Immun* (1981) 32:547–552)and Judd, R. C. (*Infect Immun* (1982) 37:632–641). Strains FA628 (sac-1$^+$, sac-3) and FA899 (sac-1, sac-3$^+$) are $Sac^S$ transformants of FA19 (Shafer, W. M. et al., *Infect Immun* (1982) 35:764–769). Strains FA5101 and WS1 are pycin-resistant mutants of strain FA19 that produce a truncated LOS (Lucas, C. E. et al., *Molec Microbiol* (1995) 16:1001–1009). Bacteria were streaked on NGTM medium, incubated overnight at 37° C. in 5% $CO_2$/room air and passaged daily. Bacteria from plates were placed in 25 ml GC broth and incubated at 37° C. with shaking for 3 hours to obtain mid-log gonococci.

Underlay and overlay gels were prepared as previously described for the radial diffusion assay of Qu, X. D. et al. Peptides were dissolved and serially diluted in 0.01% acetic acid and 5 ml aliquots were tested. Plates were incubated in a $CO_2$ incubator at 37° C. for 3 hours before pouring the overlay gel, to allow peptides to diffuse into the underlays. After overnight incubation, the minimal inhibitory concentrations (mg/ml) were determined from the X-intercepts of the curves as described by Qu et al. Each strain showed protegrin-sensitivity (Tables 17–19).

TABLE 17

Activity Against Neisseria gonorrhoeae

| Protegrin | Sequence | amino acids n | Minimal Inhibitory Concentration (µg/ml) | | |
|---|---|---|---|---|---|
| | | | F62 | JS-1 | FA19 |
| PG-1 | RGGRLCYCRRRFCVCVGR | 18 | 1.3 ± 0.1 | 1.2 ± 0.1 | 1.9 ± 0.1 |
| PC-13 | RGGRLCYCRRRFCVCV-- | 16 | 0.6 ± 0.2 | 1.4 ± 0.04 | 2.3 ± 0.8 |
| PC-11 | ----LCYCRRRFCVCVGR | 14 | 1.0 ± 0.1 | 1.6 ± 0.3 | 2.8 ± 0.1 |
| PC-17 | ----LCYCRRRFCVCV-- | 12 | 0.6 ± 0.1 | 1.3 ± 0.2 | 1.7 ± 0.1 |
| PC-37 | -----CYCRRRFCVCVGR | 13 | 4.2 ± 1.1 | 1.8 ± 0.2 | 10.7 ± 0.5 |
| PC-45 | RGGRLCYCRRRFCVC--- | 15 | 1.1 ± 0.3 | 2.9 ± 0.03 | 7.6 ± 2.1 |
| PC-71 | -----CYCRRRFCVCV-- | 11 | 4.5 ± 0.8 | 4.7 ± 1.0 | 16.1 ± 0.9 |
| PC-72 | ----LCYCRRRFCVC--- | 11 | 2.7 ± 0.2 | 2.3 ± 0.8 | 12.8 ± 0.0 |
| PC-73 | -----CYCRRRFCVC--- | 10 | 29.8 ± 1.5 | 48.3 ± 22.5 | 104.4 ± 7.4 |
| PC-8 | RGGRLAYARRRFAVAVGR | 18 | 21.4 ± 5.8 | 46.0 ± 7.0 | 431 ± 13 |
| PC-9 | RGGRLAYCRRRFCVAVGR | 18 | 1.0 ± 0.3 | 1.1 ± 0.2 | 7.3 ± 2.3 |
| PC-10 | RGGRLCYARRRFAVCVGR | 18 | 0.7 ± 0.1 | 0.8 ± 0.1 | 1.6 ± 0.0 |
| PC-18 | ----LCYARRRFAVCV-- | 12 | 0.7 ± 0.1 | 2.1 ± 0.4 | 8.3 ± 2.0 |
| PC-64 | ----LCYTRRRFTVCV-- | 12 | 0.7 ± 0.1 | 1.4 ± 0.2 | 4.5 ± 0.3 |
| PC-20 | ----LAYCRRRFCVAV-- | 12 | 1.1 ± 0.2 | 8.5 ± 2.5 | 32.4 ± 5.7 |
| PC-64a | ----LTYCRRRFCVTV-- | 12 | 0.7 ± 0.1 | 0.7 ± 0.1 | 2.1 ± 0.1 |

All of the peptides in the table are the C-terminal amides.

Protegrins PC-13, PC-11 and PC-17 demonstrate that amino acid residues $X_1$ through $X_4$ and $X_{17}$ through $X_{18}$ may be deleted from PG-1 without a loss of inhibitory activity (Table 17).

The effect of the two intramolecular disulfide bonds of PG-1 on inhibition of *N. gonorrhoeae* was determined. Elimination of both disulfide bonds (protegrin PC-8) reduces the inhibitory effect on all strains tested (Table 17). In contrast, protegrin PC-10, which lacks the $Cys_8$:$Cys_{13}$ disulfide bond has increased activity against strains F62, JS-1 and FA19. A variant of PG-1 lacking the $cys_6$:$cys_{15}$ disulfide bond (PC-9) retains full activity against strains F62 and JS-1 and shows a 3.8-fold reduction of activity against strain FA19. Truncated 12-mer variants of PG-1 having a single disulfide bond also show potent inhibitory activity (see protegrins PC-18, PC-64, PC-20 and PC-64a in Table 18).

The inhibitory activity of protegrin variants was also determined for two serum-sensitive strains, FA628 (sac-1+) and FA899 (sac-3+), which were derived for the serum resistant FA19 strain. PG-1 showed similar activity against the wild-type, serum resistant FA19 strain and the serum-sensitive derivative strains FA628 and FA899 (Table 18). Serum-sensitive strains were two to four fold more susceptible to PC-8 than was the serum-resistant strain. Variants PC-9 and PC-10, which have one disulfide bond, retain strong inhibitory activity.

TABLE 18

Effect of Protegrins Against Serum-Sensitive *N. gonorrhoeae* Strain

| Protegrin | amino acids n | Minimal Inhibitory Concentration (µg/ml) | | |
|---|---|---|---|---|
| | | FA19 | FA628 | FA899 |
| PG-1 | 18 | 2.1 ± 0.1 | 1.6 ± 0.1 | 1.6 ± 0.1 |
| PC-8 | 18 | 420.8 ± 24.2 | 150.9 ± 14.0 | 263.5 ± 10.3 |
| PC-9 | 18 | 11.2 ± 1.8 | 4.0 ± 0.1 | 3.9 ± 0.2 |
| PC-10 | 18 | 1.7 ± 0.1 | 1.2 ± 0.1 | 1.3 ± 0.1 |

Because LOS truncation increases susceptibility of gonococci to antimicrobial proteins of human PMN (Shafer, W. M. et al., 1986, *J Infect Dis* 86:910–917), protegrins PG-1, PC-8, PC-9 and PC-10 were tested against LOS mutants FA5101, WS1 and wild-type strain FA19 (Table 19). LOS truncation resulted in increased susceptibility of *N. gonorrhoeae* to the linearized protegrin PC-8, but had little effect on susceptibility to PG-1 or PC-10.

TABLE 19

Effect of Protegrins Against *N. gonorrhoeae* LOS Mutants

| Protegrin | amino acids n | Minimal Inhibitory Concentration (µg/ml) | | |
|---|---|---|---|---|
| | | FA19 | FA5101 | WS1 |
| PG-1 | 18 | 2.1 ± 0.1 | 1.5 ± 0.2 | 1.4 ± 0.2 |
| PC-8 | 18 | 420.8 ± 24.2 | 23.1 ± 9.3 | 29.7 ± 12.8 |

TABLE 19-continued

Effect of Protegrins Against N. gonorrhoeae LOS Mutants

| Protegrin | amino acids n | Minimal Inhibitory Concentration (μg/ml) | | |
|---|---|---|---|---|
| | | FA19 | FA5101 | WS1 |
| PC-9 | 18 | 11.2 ± 1.8 | 2.7 ± 0.4 | 2.6 ± 0.7 |
| PC-10 | 18 | 1.7 ± 0.1 | 1.2 ± 0.1 | 1.1 ± 0.1 |

EXAMPLE 13

Electron Microscopy of *N. gonorrhoeae* treated with Protegrins

The effect of treatment of *N. gonorrhoeae* with 50 μg/ml PG-1 or the truncated derivative PC-17 was determined. Transmission electron microscopy of bacteria after 60 minutes treatment with PG-1 reveals central vacuolation and membrane-associated, electron-dense structures. Scanning electron microscopy of bacteria treated with PG-1 or PC-17 revealed surface lesions approximately 100 nm in diameter.

EXAMPLE 14

Effect of Saliva on Antimicrobial Activity

The radial diffusion assay of Lehrer et al., 1991, *J. Immunol. Meth.* 137:167 was used, except that the media in the underlay agar contained phosphate buffer at 10 mM, pH6.5, 100 mM NaCl, 1% TSB, 1% agarose. The media in the overlay contain 10 mM phosphate buffer, pH 6.5, 100 mM NaCl, 2×TSB, 1% agarose. The peptides were diluted from 10× stock made up in 0.01% acetic acid (AA) either with 10 mM acetate buffer pH5 or with saliva.

The results are given as the minimal concentration required to produce a detectable zone of clearance, or MCZ—i.e., an extrapolated value to the x-axis when the concentration of peptide is plotted against the diameter of the zone. The results are shown in Table 20.

TABLE 20

Effect of Diluent on MCZ (μg/mL) against *E. coli* 004

| Sequence | Acetate buffer | Saliva |
|---|---|---|
| RGGRLCYCRRRFCVCVGR | 0.48 | 1.14 |
| RGGGLCYARGWIAFCVGR | 4.16 | 38.30 |
| RGGGLCYKRGWIKFCVGR | 2.71 | 0.56 |
| RGWGLCYCRPRFCVCVGR | 0.39 | 12.60 |
| RGGRLCYCRRRFCVCVGR* | 0.59 | 1.45 |
| LCYCRRRFCVCF | 4.14 | 6.11 |
| RLCYCRPRFCVCV | 3.36 | 6.83 |
| LCYCRGRFCVCVGR | 2.37 | 5.68 |
| RLCYCRPRFCVCVGR | 1.60 | 6.86 |
| RWRLCYCRPRFCVCV | 1.04 | 39.00 |
| RGWRACYCRPRFCACVGR | 0.71 | 1.84 |
| GWRLCYCRPRFCVCVGR | 0.86 | 47.50 |

TABLE 20-continued

Effect of Diluent on MCZ (μg/mL) against *E. coli* 004

| Sequence | Acetate buffer | Saliva |
|---|---|---|
| RLCACRGRACVCV | 13.70 | 9.76 |
| WLCYCRRRFCVCV* | 5.05 | 36.00 |
| RLCYCRXRFCVCV (X = MeGly) | 2.43 | 2.54 |
| RLCYCRPRFCVCVGR* | 3.65 | 12.80 |
| RGGGLCYCRPRFCVCVGR* | 3.51 | 11.90 |
| RRCYCRRRFCVCVGR | 3.02 | 8.07 |

Peptides noted with * are acid forms; all others are amide forms.

A large number of the peptides tested showed comparable or even improved activity in the presence of saliva.

EXAMPLE 15

Antimicrobial Activity of Additional Protegrins

The following example provides assays for measuring the antimicrobial activity that were used to test additional peptides of the invention described hereinbelow. The following reagents, stock solutions and cultures are used in the assays that follow.

Microorganisms: *Escherichia coli* ML-35p and vancomycin-resistant *Enterococcus faecium* (VRE) were obtained from Dr. Robert Lehrer (UCLA, see also, Lehrer et al., 1988, *J. Immunol. Methods* 108:153) and Dr. Gary Schoolnik (Stanford), respectively. *Pseudomonas aeruginosa* (ATCC 9027), *Candida albicans* (ATCC 1023), and methicillin resistant *Staphylococcus aureus* (ATCC 33591) were obtained from the American Type Culture Collection, Rockville, Md.

Microorganisms from other sources, such as, for example, clinical isolates, can be used interchangeably with the above-described microorganisms in the assays described herein.

Media and Reagents:

Trypticase Soy Agar (TSA; Becton-Dickinson, Cockeysville, Md., BBL #4311768): dissolve 40 g in 1 Liter deionized water, autoclave 121° C., 20 minutes.

Trypticase Soy Broth (TSB; Becton-Dickinson, Cockeysville, Md., BBL #4311768): dissolve 30 g in 1 Liter deionized water, autoclave 121° C., 20 minutes, and store at room temperature.

2× Trypticase Soy Broth (2× TSB): dissolve 60 g in 1 Liter deionized water, autoclave 121° C., 20 minutes, and store at room temperature.

Glycerol (20% v/v): mix 20 mL glycerol with 80 mL deionized water, Filter sterilize with 0.20μ filter and store at room temperature.

Monobasic phosphate buffer (100 mM): dissolve 13.7 g sodium phosphate monobasic (Fisher #S368–500) in 1 Liter deionized water. Filter sterilize with 0.20μ filter and store at room temperature.

Dibasic phosphate buffer (100 mM): dissolve 14.2 g sodium phosphate dibasic (Fisher #S374–500) in 1 Liter deionized water. Filter sterilize with 0.45μ filter and store at room temperature.

Phosphate-buffered saline (PBS; 10 mM phosphate, 100 mM NaCl, pH 7.4): mix 15 mL dibasic phosphate buffer (100 mM), 5 mL monobasic phosphate buffer (100 mM), 4 mL NaCl (5 M) and 176 mL deionized water. Adjust pH if necessary, filter sterilize with 0.45μ filter and store at room temperature.

Phosphate buffer (100 mM, pH 6.5): mix 40 mL dibasic phosphate buffer (100 mM) with 160 mL monobasic phosphate buffer (100 mM). Adjust pH if necessary, filter sterilize with 0.45μ filter and store at room temperature.

Liquid Testing Medium (LTM): aseptically combine the following sterile ingredients: 10 mL Phosphate buffer (100 mM, pH 6.5), 1.0 mL TSB, 2 mL NaCl (5 M) and 87 mL deionized water. Store at room temperature.

Acetic acid (0.01% v/v): mix 10 μL acetic acid with 100 mL sterile deionized water.

Agarose: mix 1 g agarose (Sigma #S6013) in 80 mL deionized water, autoclave 121° C., 20 minutes.

Agarose Underlay Medium: combine 10 mL Phosphate buffer (100 mM, pH 6.5), 1.0 mL TSB, 2 mL NaCl (5 M) and 7 mL deionized water with 80 mL tempered (50° C.) agarose.

2× TSB Agarose Overlay Medium: dissolve 60 g TSB and 10 g agarose in 1 Liter deionized water, aliquot 100 mL per bottle, autoclave 121° C., 20 minutes, and store at room temperature.

Preparation of Microorganism Slants: Each strain was cultured on TSA. Isolated colonies were transferred into TSB (10 mL in a sterile 50 mL Erlenmeyer flask) using a sterile, disposable loop and the flask incubated at 37° C. (bacteria) or 30° C. (yeast) with shaking (200 RPM) for 16–18 hours.

Broth cultures were diluted 1:1 with 20% sterile glycerol and stored as 1.0 mL aliquots at −80° C. For daily inocula, liquid was transferred from a thawed vial using a sterile loop and then spread onto the surface of TSA slants. The screw capped tubes were incubated overnight and stored at 4° C. for up to one month.

Preparation of Inoculum:

1. Remove the cap from tube and lightly touch a sterile loop to the area of heavy growth on the TSA slant.
2. Inoculate 10 mL of TSB (50 mL flask) and incubate the flask in a shaking water bath for 18 hours (overnight) at 37° C. (bacteria) or 30° C. (yeast) at 200 RPM.
3. In a cuvette, dilute 50 μL of the overnight culture 1:20 with TSB and measure the absorbance at 600 nm ($A_{600}$) using TSB as a reference. The $A_{600}$ of the diluted culture should be between 0.1–0.4.
4. In a 250 mL Erlenmeyer flask, dilute 50 μL of the overnight culture 1:1000 with TSB (bacteria) or 1:100 with TSB (yeast).
5. Incubate the flask in a shaking water bath at 37° C. (bacteria) or 30° C. (yeast) at 200 RPM for approximately 2–3 hours until log-phase is reached, i.e. until the $A_{600}$ of the culture is between 0.200 and 0.400 without further dilution.
6. Transfer 25 mL of the log-phase culture to a sterile centrifuge tube and centrifuge at 2000 rpm and 4° C. for 10 minutes. Decant the supernatant, add 25 mL of sterile PBS and resuspend the pellet by vortexing.
7. Centrifuge the suspension at 2000 rpm and 4° C. for 10 minutes. Decant the supernatant and resuspend the pellet with 5 ml sterile PBS.
8. Measure the $A_{600}$ of the undiluted suspension. If the absorbance is above 0.5, dilute with sterile PBS until the absorbance is between 0.100 and 0.500.
9. Determine the number colony-forming units per milliliter suspension (CFUs/mL) by preparing 10-fold serial dilutions in saline (0.87%) and spreading 100 μL of the $10^4$-, $10^5$-, and $10^6$-fold dilutions onto TSA plates, one dilution per plate. Incubate overnight, count the number of colonies and determine the CFUs/mL (an accurate determination requires approximately 30–300 colonies per plate).

For the strains reported, the CFUs/mL for a suspension having an $A_{600}$=0.2 have been determined as reported in the table below:

| CFUs/mL of Suspension ($A_{600}$ = 0.2) | |
| --- | --- |
| Strain | CFUs/mL |
| E. coli | $8.0 \pm 10^7$ |
| P. aeruginosa | $7.8 \pm 10^7$ |
| MRSA | $2.0 \pm 10^7$ |
| VRE | $3.8 \pm 10^7$ |
| C. albicans | $9.7 \pm 10^7$ |

Preparation of Peptide Stock Solutions:

1. Weigh approximately 1.0 mg of each peptide to be tested into a sterile polypropylene cryovial (1.8 mL).
2. Add sufficient acetic acid (0.01%) to make a stock solution having a concentration of 1280 μg/mL. Dispense the stock solution into several vials, 100 μL per vial, and store the aliquots, tightly sealed, at −80° C.

6.5 Radial Diffusion (MCZ) Assay

The MCZ assay uses minimal amounts of test materials to determine the sensitivity of microorganisms to various antimicrobial compounds. Cells are grown to approximately mid-log phase and resuspended in minimal nutrient buffered agarose. Agarose (not agar) is used in this gel to avoid electrostatic interactions between antimicrobial peptides and the polyanionic components of standard agar. Peptides diffuse radially into the gels from small wells and the diameter of the zone of growth inhibition is proportional to the concentration of peptide in the solution (Lehrer et al., 1988, J. Immunol. Methods 108:153; Lehrer et al., 1991, J. Immunol. Methods 137:167).

Preparation of MCZ Assay Plates:

1. For each petri plate to be poured, dispense 10 mL of tempered (50° C.) Agarose Underlay Medium into a sterile polypropylene tube (15 mL). Add 4×10⁶ CFUs of the desired strain to each tube. Mix well by inverting tube 3 times. Immediately pour the molten agarose into the petri dishes.
2. After the agarose has solidified, use a sterile canula (3 mm i.d.) to punch 16 wells (4×4 evenly spaced grid) into the agarose. Remove the agarose plugs with a pasteur pipette and trap the agarose in a flask with a side arm port attached to a vacuum.
3. From the peptide stock solution, prepare serial 2-fold dilutions (from 128 μg/mL to 0.06 μg/mL) using acetic acid (0.01%) as a diluent, or, for peptide concentrations lower than 50 μg/mL, sodium acetate (10 mM, pH 5) containing Human Serum Albumin (HSA; 0.1% w/v) as a diluent.
4. Dispense 5 μL of each serial dilution into the agarose wells, one serial dilution per well.
5. Dispense diluents into wells as negative controls and protegrin-1 (U.S. Pat. No. 5,464,823; 32 μg/mL, 8 μg/mL and 2 μg/mL) into wells as positive controls.

6. Incubate the plates at 37° C. (bacteria) or 30° C. (yeast) for 3 hours.
7. Dispense 2× TSB Agarose Overlay Medium (10 mL) onto the surface of each plate, allow the agar to solidify and incubate plates, inverted, at 37° C. (bacteria) or 30° C. (yeast) for 16–18 hours.
8. Examine the plates and measure (in mm) the diameter of the zone of growth inhibition (area of clearing around each well).
9. Plot the diameter of the zone of growth inhibition (Y-axis) versus the concentration of peptide in the well (X-axis) and obtain the line of best fit using linear regression analysis. The X-intercept of the line of best fit is the minimum concentration for zone of growth inhibition (MCZ) for each peptide concentration.

6.6 Microbroth Dilution (MCB) Assay

The microbroth dilution method accomodates large numbers of samples and is more amenable to automation than the MCZ assay and the data analysis is direct and simple. A key step in this assay is combining microorganisms and peptide in a defined minimal nutrient buffer system that minimizes interference with the peptide's biological activity. In addition, the presence of 0.1% (w/v) human serum albumin (HSA) or bovine serum albumin (BSA) to the peptide diluent minimizes adsorption of peptide to the container.

Preparation of MCB assay plates:
1. Dispense 100 μL of log-phase cells in LTM (MCB-5 is 4×10$^5$ CFUs/mL; MCB-3 is 4×10$^3$ CFUs/mL) into each well of a sterile 96-well microtiter plate.
2. From the peptide stock solution, prepare serial two-fold dilutions (from 1280 μg/mL to 0.625 μg/mL) using acetic acid (0.01%) as a diluent, or, for peptide concentrations lower than 50 μg/mL, sodium acetate (10 mM, pH 5) containing HSA or BSA (0.1%w/v) as a diluent.
3. Dispense triplicate aliquots (11 μL) of each serial two-fold dilution into the wells of the microtiter plate.
4. Incubate the plate at 37° C. (bacteria) or 30° C. (yeast) for 3 hours.
5. Add 100 μL of 2× TSB to each well, mix, and incubate at 37° C. (bacteria) or 30° C. (yeast) for an additional 16–18 hours.
6. Examine the plates and evaluate each well for turbidity (cell growth). Often, MRSA will settle out and form a pellet at the bottom of the well. NRSA can be evaluated by placing the microtiter plate on a stand and examining the bottom of the well using a tilted mirror.
7. The minimum concentration for inhibition of growth in broth medium (MCB) is defined as the lowest concentration of peptide that inhibits all visible growth. If the MCB values for each of the triplicate samples differ, the MCB is obtained by averaging the results of the three samples.
8. The minimum concentration of peptide showing at least 99.9% biocidal activity (at least a 3 log decrease from starting inoculum) is determined by incubating a 50 μL aliquot from each well on a TSA plate for 24 hours at 37° C. (bacteria) or 30° C. (yeast) (for plating, 1.5 mL TSA in each well of a 24-well plate minimizes cross contamination).

6.7 Modified NCCLS Minimum Inhibitory Concentration (MIC) Assay

The National Committee for Clinical Standards (NCCLS) requires that test compounds be prepared as stock solutions in Mueller-Hinton Broth ("MHB") at 512 μg/mL. The stock solutions are serially diluted (two-fold) in medium and each serial dilution added 1:1 to medium containing 1×10$^6$ CFU/mL bacteria (National Committee on Clinical Laboratory Standards, December 1994, "Performance Standards for Antimicrobial Susceptibility Testing," NCCLS Document M100-S5 Vol. 14, No. 16; Methods for Dilution Antimicrobial Susceptibility Test for Bacteria that Grow Aerobically, 3d Ed., Approved Standard M7-A3, National Committee for Clinical Standards, Villanova, Pa.).

It has been found that the peptides of the invention precipitate in MHB at concentrations greater than 128 μg/mL. Thus, following the NCCLS protocol would result in serial two-fold dilutions containing less peptide than calculated, yielding erroneously high MIC values.

To overcome this problem, the following modified NCCLS assay is the preferred method for determining MICs of the peptides of the invention. In the method, precipitation is avoided by preparing concentrated (10×) stock solutions of test peptide in a buffer that is suitable for the peptide and which does not exhibit deleterious effects on the microorganisms (0.01% v/v acetic acid, 0.1% w/v HSA)and diluting the stock 1:10 into MHB containing the microorganisms.

Preparation of MIC assay plates:
1. Prepare a fresh overnight culture of test organism in Meuller-Hinton broth (MHB; Becton-Dickinson, Cockysville, Md., BB2 #11443).
2. Dilute the culture to approximately 4×10$^5$ CFUs/mL with fresh MHB and dispense 100 μL aliquots into each well of a sterile 96-well microtiter plate.
3. From the peptide stock solution, prepare serial two-fold dilutions (from 1280 μg/mL to 0.625 μg/mL) using acetic acid (0.01%) as a diluent, or, for peptide concentrations lower than 50 μg/mL, sodium acetate (10 mM, pH 5) containing Human Serum Albumin (HSA; 0.1%w/v) as a diluent.
4. Dispense triplicate aliquots (11 μL) of each serial dilution into the wells of the microtiter plate.
5. Incubate the plate for 16–18 hours, without aeration, at 37° C. (bacteria) or 30° C. (yeast).
6. Examine the plates and evaluate each well for turbidity (cell growth). Often, MRSA will settle out and form a pellet at the bottom of the well. MRSA can be evaluated by placing the microtiter plate on a stand and examining the bottom of the well using a tilted mirror.
7. The minimum inhibitory concentration (MIC) is defined as the lowest peptide concentration that inhibits all visible growth. If the MIC values for each of the triplicate samples differ, the MIC is obtained by averaging the results of the three samples.
8. The minimum concentration of peptide showing 100% biocidal activity is determined by incubating a 10 μL aliquot from each well on a TSA plate for 24 hours at 37° C. (bacteria) or 30° C. (yeast) (for plating, 1.5 mL TSA in each well of a 24-well plate minimizes cross contamination).

6.8 Kinetic Bactericidal Assay

The following assay is used to determine the rate at which a peptide kills a target microorganism, as well as to determine if a peptide is bactericidal or bacteriostatic.

Assay
1. Dispense 200 μL of log-phase cells in LTM (4×10$^5$ CFUs/mL) into each well of a 96-well microtiter plate solution.

2. At time T=0 minutes, add 22 μL of 1280 μg/mL peptide to well A1 and mix by triturating 3 times.
3. Wait 30 seconds and add 22 μL of a second concentration of peptide the to the next well (A2) and mix by triturating 3 times.
4. Repeat the process, staggering each peptide addition by 30 seconds, until all concentrations of peptide have been added. Typically, 4-fold serial dilutions of stock peptide (i.e., 1280, 320, 80, 20 and 5 μg/mL peptide diluted 1:10 into each well) produces good comparative kill curves. Add 22 μL of 0.01% acetic acid to one well as a control.
5. At time T=15 minutes, mix well A1 by triturating 3 times and transfer 20 μL to an empty sterile petri dish (100 mm×15 mm).
6. Quickly add 20 mL of tempered (50° C.) TSA and gently swirl plate to mix.
7. Repeat steps 5–6 until all peptide concentrations have been plated.
8. For the control well, dilute the sample 1:100 with LTM and plate 50 μL of the dilution to obtain an accurate determinations of CFUs.
9. After the agar has solidified, invert the plates and incubate at 37° C. (bacteria) 30° C. (yeast) for 18–24 hours.
10. Repeat steps 5–9 for all peptide concentrations and control samples at times T=30, 60, 120, and 240 minutes.
11. Count the number of CFUs per plate and estimate the reduction in CFUs for each peptide concentration. In order to assess an effect using this assay, the peptide must reduce the CFUs by at least one log (i.e., at least 800 CFUs per plate). Although such numbers are higher than recommended for accuracy (30–300 CFUs/plate), log-order changes in recoverable CFUs indicate significant bactericidal efficacy.
12. To obtain comparative kill curves, plot the log of fractional survival versus peptide concentration.

Table 21 shows the antimicrobial activity of a number of the compounds of the invention against various target organisms using the MCB-3 assay described above (i.e., at $10^3$ CFU. The results are given as a "minimal concentration for inhibition of growth in broth" (MCB) which is the lowest concentration that results in no visible turbidity. The "minimal bactericidal concentration" (MBC) on TSA was equivalent to the MCB. The units of concentration are μg/ml. As shown in Table 21, various substitutions can be made in the peptide chain in order to fine-tune the spectrum of antimicrobial activity. An asterisk at the C-terminus indicates that the peptide was supplied in the form of the free acid; otherwise the amide was used in the assay.

TABLE 21

Evaluation of Antimicrobial Peptides in MCB-3 (μg/mL)

| Sequence | | MRSA | Psa | VREF | Candida | E. coli |
|---|---|---|---|---|---|---|
| RGGRLCYCRRRFCVCVGR* | | 1.5 | 0.11 | | 1.2 | 0.6 |
| RGGGLCYCRRRFCVCVGR* | | | | | 3.29 | 0.4 |
| RGGGLCYCRRGFCVCFGR | | 1.93 | 0.14 | | 1.62 | |
| RGGGLCYCRRPFCVCVGR | | 3.1 | 0.06 | | 7.69 | 0.15 |
| RGGGLCYCRPRFCVCVGR* | | | | | 17.7 | 3.51 |
| RGGRLCYCRXRFCVCVGR* | (X = MeGly) | 5.33 | 2 | 1 | | |
| RGGRLCYCRXRFCVCVGR | (X = MeGly) | 4 | 1.67 | 0.83 | | |
| RGGLCYCRGRFCVCVGR | | 10.6 | 0.83 | | | |
| RGGRLCYCXGRFCVCVGR | (X = Cit) | | | | | |
| XGGRLCYCRGRFCVCVGR | (X = Cit) | | | | | |
| RGGRVCYCRGRFCVCVGR | | 8 | 1 | | | |
| RGGRVCYCRGRFCVCVGR* | | | | | | |
| RGGGLCYCFPKFCVCVGR | | 3.48 | 1.2 | | 15.96 | |
| RGWGLCYCRPRFCVCVGR | | 1.55 | 0.27 | 0.09 | 5.68 | 0.1 |
| RGWRLCYCRXRFCVCVGR* | (X = MeGly) | 26.7 | 10.6 | | | |
| RGWRLCYCRGRFCVCVGR | | 5.3 | 0.5 | | | |
| RGWRLCYCXPRFCVCVGR | (X = Cit) | | | | | |
| RWRLCYCRPRFCVCVGR | | 4.7 | 3.3 | | 1.7 | |
| RGWRLCYCRPRFCVCVGR | | 4.7 | 5.3 | | 6.1 | |
| RGWRACYCRPRFCACVGR | | 4.7 | 1.3 | 2 | 4.7 | 0.34 |
| GWRLCYCRPRFCVCVGR | | 4.7 | 4 | | 2.7 | 0.86 |

TABLE 21-continued

Evaluation of Antimicrobial Peptides in MCB-3 (μg/mL)

| Sequence | | MRSA | Psa | VREF | Candida | E. coli |
|---|---|---|---|---|---|---|
| RWRLCYCKGKFCVCVGR | | | | | | |
| RGWRLCYCRXRFCVCVGR | (X = MeGly) | | | | | |
| GGWRLCYCRGRFCVCVGR | | 16 | 9.3 | | | |
| RGGWLCYCRGRFCVCVGR | | 32 | 5.3 | | | |
| RLLRLCYCRXRFCVCVGR | (X = MeGly) | 4 | 3.3 | | | |
| RLLRACYCRXRFCVCVGR | (X = MeGly) | 10.6 | 3 | | | |
| RLLRLCYCRRRFCVCVGR | | | | | | |
| RGLRXCYCRGRFCVCVGR | (X = Cha) | 6.7 | 2.3 | | | |
| RGGRLCYCRXRZCVCWGR | (X = MeGly) (Z = Cha) | | | | | |
| RGGRWCVCRXRZCYCVGR | (X = MeGly) (Z = Cha) | | | | | |
| RGLRXCYCRGRFCVCVGR* | (X = Cha) | 16 | 8 | | | |
| RGGRWCVCRGRXCYCVGR | (X = Cha) | | | | | |
| RGGRLCYCRRRFCXCVGR | (X = MeVal) | | | | | |
| LCYCRRRFCVCV | | 16 | 4 | 4 | 5.9 | 1.9 |
| LCYCRRRFCVCV* | | 32 | 8 | | | |
| LCYCRPCFCVCV | | 64 | 5.3 | 3.33 | >64 | |
| LCYCRRRFCVCF | | 4 | 2 | 2 | | 3 |
| LCACRRRACVCV | | >64 | 13.3 | | | |
| LCYCRXRFCVCV | (X = D-Arg) | 4 | 2 | 1.32 | 5.72 | 1.18 |
| LCWCRRRFCVCV | | 5.3 | 2 | 4 | 8.91 | 0.76 |
| WCYCRRRFCVCV | | 5.3 | 2.7 | 2 | 4.7 | 2.3 |
| LCYCRRRXCVCV | (X = hPhe) | 8(64) | 6.7 | 2.7 | | |
| LCYCRRRXCVCV | (X = Phe(4-Cl)) | 4 | 2 | 1.3 | | |
| XCYCRRRFCVCV | (X = Cha) | 2.67 | 2.67 | 1.33 | | |
| LCYCRRRFCXCV | (X = D-His) | >64 | 10.7 | | >64 | |
| LCYCRRRXCVCV | (X = MeGly) | >64 | 13.3 | 42.7 | | |
| LCYCRRRXCVCV | (X = MePhe) | | | | | |
| LCYCRRRFCXCV | (X = MeVal) | | | | | |
| LCXCRRRXCVCV | (X = Cha) | 18.7 | 16 | 8 | 3.98 | 0.37 |
| LCGCRRRGCVCV | | >32 | | >16 | | >128 |
| LCACRGRACVCV | | >32 | 6.7 | 21.3 | | |
| RLCYCRRRFCVCV | | 8 | 4 | | | |
| RACYCRPRFCACV | | >64 | 2.7 | | | |
| RLCYCRPRFCVCF | | | | | | |
| RLCYCRPRFCVCV | | 5.3 | 2.7 | 2 | | |
| KLCYCKPKFCVCV | | 16 | 2 | 2.67 | | 2.07 |

TABLE 21-continued

Evaluation of Antimicrobial Peptides in MCB-3 (µg/mL)

| Sequence | | MRSA | Psa | VREF | Candida | E. coli |
|---|---|---|---|---|---|---|
| RLCACRGRACVCV | | >32 | 2.7 | 10.7 | 9.51 | 3.93 |
| RLCYCRXRFCVCV | (X = MeGly) | 5.3 | 2 | 2 | 6 | 2.54 |
| RXCFCRPRFCVCV | (X = Cha) | 2.67 | 2.67 | 0.83 | | |
| RWCFCRPRFCVCV | | 3.3 | 2 | 2 | 5.2 | 2.2 |
| WLCYCRRRFCVCV | | 5.3 | 1.3 | | | |
| WLCFCRRRFCVCV | | | | | | |
| FLCFCRRRFCVCV | | | | | | |
| WLCFCRRRXCVCV | (X = MePhe) | | | | | |
| WLCYCRRRFCVCV* | | 8 | 4 | 2 | 7.14 | 0.99 |
| RLCYCRRRFCVCV* | | 8 | 1.67 | 2 | | |
| WYCYCRRRFCVCV* | | | | | | |
| WXCYCRRRFCVCV* | (X = Cha) | | | | | |
| RXCFCRGRZCVCV | (X = Cha) (Z = MePhe) | | | | | |
| XLCFCRRRZCVCV | (X = Cha) (Z = MePhe) | | | | | |
| RLCYCRPRFCVCVGR | | 0.65 | 0.1 | | 0.89 | 0.05 |
| RLCYCRPRFCVCVGR | | 3.3 | 0.7 | 1.3 | 3.3 | 0.98 |
| RLCYCRPRFCVCVGR* | | 8 | 2.7 | 2 | 12.1 | 1.6 |
| WLCYCRRRFCVCVGR* | | | | | | |
| WXCYCRRRFCVCVGR* | (X = Cha) | | | | | |
| RLCYCRGPFCVCR | | 16.6 | 1.1 | | 7.73 | |
| RRWCFVCYAGFCYRCR | | 64 | 8 | 4 | | |
| RGGRLCYCRRRFCVC | | >32 | 1.6* | 2.7 | | |
| RRCYCRRRFCVCVGR | | >64 (32) | 1.3 | 2 | | 8.07 |
| RRCYCRGRFCGCVGR | | | | | | |
| RWRCYCGRRFCGCVGR | | | | | | |
| RARCYCGRRFCGCVGR | | | | | | |
| GWRCYCRGRFCGC | | | | | | |
| RGWACYCRGRFCVC | | | | | | |
| RRCYGRRRFGVCVGR | | | | | | |
| RGWRLCYGRGRFKVC | | | | | | |
| RGWRLCYCRGRFCVC | | | | | | |
| CYCRRRFCVCF | | 53.3 | 4 | 3.33 | >64 | |
| CYCRRRFCVCVGR | | >64 | 2 | 21.3 | | |
| RGWRLCYCRXRFCVC | (X = MeGly) | | | | | |
| RGWRGCYCRXRFCGC | (X = MeGly) | >64 | 10.7 | | | |
| LCYCRRRFCVCVGR | | 8 | 2 | 5.8 | | |

TABLE 21-continued

Evaluation of Antimicrobial Peptides in MCB-3 (μg/mL)

| Sequence | | MRSA | Psa | VREF | Candida | E. coli |
|---|---|---|---|---|---|---|
| LCYCRPRFCVCVGR | | 13.3 | 4 | | | |
| LCYCKPKFCVCVGK | | 64 | 2 | | | |
| LCYCRGRFCVCVGR | | 8 | 2 | 2 | | 2.14 |
| LCYCRPRFCVCVGRGR | | 8 | 2 | | | |
| RRWCYCRPRFCVCVR | | 2.87 | 0.18 | | 2.98 | |
| WRLCYCRPRFCVCVGR | | 5.3 | 4 | | 5 | |
| GWLCYCRGRFCVCVGR | | 21 | 16 | | | |
| RWLCYCRGRFCVCVGR | | 16 | 5.3 | | | |
| RLLCYCRGRFCVCVGR | | 6.6 | 1.3 | | | |
| RWRLCYCRPRFCVCV | | 8 | 4 | | 5 | |
| RXRLCYCRZRFCVCV | (X = Cha) (Z = MeGly) | 16 | 5.3 | | | |
| RGWRLCYCRGRXCVCV | (X = Cha) | 32 | 13.3 | | | |
| RGGRVCYCRGRFCVCV | | 8 | 2 | | | |
| RGGRVCYCRGRFCVCV* | | 64 | 1 | | | |
| LCYCRXRFCVCV | (X = D-Ala) | 32 | 9.3 | 3.33 | >64 | |
| LCYCKPKFCVCV | | 64 | 3 | 6.7 | >64 | |
| VCYCRPRFCVCV | | 26.7 | 5.2 | | | 5.26 |
| LCYCRPRFCVCW | | 53.3 | 42.3 | | | |
| LCYRRPRFRVCV | | >64 | 4 | 16 | >64 | |
| RGWRLCYCRGRXCVCV* | (X = Cha) | >32 | >16 | | | |
| RXRLCYCRZRFCVCV* | (X = Cha) (Z = MeGly) | >32 | 21 | | | |
| RXRLCYCRGRFCVCV | (X = Cha) | | | | | |
| RGGGLCYARGWIAFCVGR | | 2.1 | 0.59 | | 32.6 | 0.81 |
| RGGGLCYARGFIAVCFGR | | 19 | 14 | | 65.8 | 3.27 |
| RGGGLCYARPRFAVCVGR | | | | | | |
| RGGGLCYTRPRFTVCVGR | | 8.7 | 0.07 | | >128 | 1.53 |
| RGGGLCYARKGFAVCVGR | | >128 | 0.01 | | >128 | 2.65 |
| RGGRLCYARRRFAVCVGR* | | | 0.05 | | 1.6 | 0.4 |
| RGGRLCYARRRFAVCVGR | | | 0.01 | | 3 | 0.08 |
| RGGGLCYKRGFIKVCFGR | | 17 | 0.19 | | 7.73 | 3.27 |
| RGGGLCYKRGWIKFCVGR | | 2.07 | 0.15 | | 2.72 | 3.56 |
| RGGGLCYRLPKFRVCVGR | | 34.77 | 0.22 | | 15.09 | 0.56 |
| RGGGLCYRLPGFRVCVGR | | 30.76 | 0.53 | | 31.4 | 8.95 |
| RGWRGCYKRGRFKGCVGR | | >64 | 9.3 | | | |
| RGWRGCYKRGRFKGCVGR* | | >32 | 8* | | | |
| LCYARRRFAVCV | | >64 | 2 | 10.7 | | |
| LCYTRRRFTVCV | | >64 | 4 | 16 | | |

TABLE 21-continued

Evaluation of Antimicrobial Peptides in MCB-3 (µg/mL)

| Sequence | MRSA | Psa | VREF | Candida | E. coli |
|---|---|---|---|---|---|
| LCYKRGRFKVCV | | | | | |
| ICYRPRFVCVGR | >128 | 6.9 | | >128 | 10.78 |

* denotes free acid form; all others are amide form.
MRSA is methicillin-resistant S. aureus
Psa is P. aeruginosa
VREF is Vancomycin-resistant E. faecium
Candida is C. albicans Tables 22–25 show activity in the kinetic bactericidal assay described above provided in terms of log reduction in CFUs for various peptides of the invention against MRSA, *Pseudomonas aeruginosa,* and the endogenous flora in saliva.

TABLE 22

Reduction of MRSA (ATCC 33591) CFUs after exposure to peptide (2 µg/ml) for 15 minutes in LTM medium at 37°

| Sequence | | Log reduction CFUs |
|---|---|---|
| RGGRLCYCRRRFCVCVGR | | 2.44 |
| RGGRLCYCRRRFCVCVGR | | 1.83 |
| RGGRLCYARRRFAVCVGR* | | 0.29 |
| RWRLCYCRPRFCVCV | | 1.41 |
| RGWRLCYCRPRFCVCVGR | | 2.06 |
| GWRLCYCRPRFCVCVGR | | >3.19 |
| XCYCRRRFCVCV | (X = Cha) | 1.32 |
| LCXCRRRXCVCV | (X = Cha) | >3.19 |
| RLCYCRRRFCVCV* | | <0.90 |
| RXRLCYCRZRFCVCV | (X = Cha) (Z = MeGly) | 1.13 |
| RGLRXCYCRGRFCVCVGR | (X = Cha) | 2.48 |
| RWLCYCRGRFCVCVGR | | 1.58 |
| GGWRLCYCRGRFCVCVGR | | 2.47 |
| RLLRLCYCRXRFCVCVGR | (X = MeGly) | 1.66 |
| RGGRLCYCRGRFCVCVGR* | | <0.90 |
| RXRLCYCRZRXCVCWGR* | (X = Cha) (Z = MeGly) | 1.38 |
| RGWRLCYCRGRFCVCVGR | | 2.12 |
| WLCYCRRRFCVCV | | 3.16 |
| RLLRLCYCRRRFCVCVGR | | 2.16 |
| RGGRLCYCRRRFCXCVGR | (X = MeVal) | <0.90 |

* Peptides noted with * are acid forms; all others are amide forms.
Initial inoculum approximately 4 × 10⁵ CFUs/ml.

TABLE 23

Log Reduction of *Pseudomanas aeruginosa* (ATCC 9027) CFUs after 15 minutes exposure to peptide (4 µg/ml) in LTM medium at 37°

| Sequence | | Log reduction CFUs |
|---|---|---|
| RGGRLCYCRRRFCVCVGR | | 3.19 |
| RGGRLCYCRPRFCVCVGR | | 3.65 |
| RGWGLCYCRPRFCVCVGR | | <1.2 |
| RGGGLCYTRPRFTVCVGR | | 2.15 |
| RGGRLCYCRRRFCVCVGR* | | 3.98 |
| XCYCRRRFCVCV | (X = Cha) | 2.81 |
| RLCYCRXRFCVCV | (X = MeGly) | <0.5 |
| RLCYCRPRFCVCVGR* | | 3.29 |
| RXCFCRPRFCVCV | (X = Cha) | 1.78 |
| RLCYCRRRFCVCV* | | 3.52 |
| RGLRXCYCRGRFCVCVGR | (X = Cha) | 2.87 |
| RGGLCYCRGRFCVCVGR | | 3.61 |
| RLLRLCYCRXRFCVCVGR | (X = MeGly) | 2.70 |
| RLLRACYCRXRFCVCVGR | (X = MeGly) | 2.71 |
| RGGRLCYCRGRFCVCVGR* | | 2.66 |
| RGWRLCYCRGRFCVCVGR | | 2.54 |
| RGGRVCYCRGRFCVCVGR | | 2.37 |
| RGGRVCYCRGRFCVCV | | 2.18 |
| RGGRVCYCRGRFCVCV* | | 1.55 |
| WLCYCRRRFCVCV | | 1.27 |

* Peptides noted with * are acid forms; all others are amide forms.
Initial inoculum approximately 4 × 10⁷ CFUs/ml.

TABLE 24

Log Reduction of Pseudomonas aeruginosa (ATCC 9027) CFUs after exposure to peptide (0.12 µg/ml) in LTM medium at 37°

| Sequence | 15 min | 120 min |
|---|---|---|
| RGGRLCYCRRRFCVCVGR | 3.48 | 3.68 |
| RGWGLCYCRPRFCVCVGR | 3.48 | 3.68 |
| RGGGLCYTRPRFTVCVGR | 0.75 | 3.68 |
| RGGGLCYARKGFAVCVGR | 1.20 | 3.68 |
| GWRLCYCRPRFCVCVGR | 2.70 | 2.21 |
| RGGRLCYCRRRFCVC | 2.25 | >3.73 |
| LCYCRRRFCVCV | 1.35 | 2.13 |

Initial inoculum approximately 4 × 10⁵ CFUs/ml.

TABLE 25

Log Reduction of CFUs endogenous flora in saliva after 15 minutes exposure to peptide (320 µg/ml) at 37°

| Sequence | | Log reduction CFUs |
|---|---|---|
| RGGRLCYCRRRFCVCVGR | | 1.80 |
| RGGRLCYCRPRFCVCVGR | | 2.04 |
| RGGGLCYKRGWIKFCVGR | | 1.09 |
| RGWGLCYCRPRFCVCVGR | | 0.53 |
| RLCYCRPRFCVCVGR | | 0.53 |
| RGGGLCYTRPRFTVCVGR | | 1.05 |
| RGGRLCYCRRRFCVCVGR* | | 1.25 |
| LCYCRGRFCVCVGR | | 1.02 |
| RWRLCYCRPRFCVCV | | 0.22 |
| RGWRLCYCRPRFCVCVGR | | 0.38 |
| RGWRACYCRPRFCACVGR | | 0.28 |
| GWRLCYCRPRFCVCVGR | | 0.26 |
| XCYCRRRFCVCV | (X = Cha) | 0.25 |
| WLCYCRRRFCVCV* | | 0.16 |
| RLCYCRXRFCVCV | (X = MeGly) | 3.43 |
| RLCYCRPRFCVCVGR* | | 0.66 |
| RGGGLCYCRPRFCVCVGR* | | 1.51 |
| RXCFCRPRFCVCV | (X = Cha) | 0.71 |
| RWCFCRPRFCVCV | | 0.52 |
| LCXCRRRXCVCV | (X = Cha) | 0.23 |
| RGGRLCYCRRRFCVC | | 0.86 |
| LCYTRRRFTVCV | | 0.64 |
| RRCYCRRRFCVCVGR | | 0.98 |

TABLE 25-continued

Log Reduction of CFUs endogenous flora in saliva after 15 minutes exposure to peptide (320 µg/ml) at 37°

| Sequence | | Log reduction CFUs |
|---|---|---|
| RLCYCRRRFCVCV* | | 0.21 |
| RXRLCYCRZRFCVCV | (X = Cha) (X = MeGly) | <0.6 |
| RGWRLCYCRGRXCVCV | (X = Cha) | <0.6 |
| RGLRXCYCRGRFCVCVGR | (X = Cha) | 1.65 |
| RGWRGCYKRGRFKGCVGR | | <0.97 |
| RGWRGCYCRXRFCGC | (X = MeGly) | <0.6 |
| RGGLCYCRGRFCVCVGR | | 2.52 |
| RLLRLCYCRXRFCVCVGR | (X = MeGly) | 0.65 |
| RLLRACYCRXRFCVCVGR | (X = MeGly) | 2.11 |
| RGGRLCYCRGRFCVCVGR* | | 2.16 |
| RGWRLCYCRGRFCVCVGR | | 1.89 |
| RGGRLCYCRGRFCVCVGR | | 2.53 |
| RGGRVCYCRGRFCVCVGR | | 2.37 |
| RGGRVCYCRGRFCVCV | | 2.07 |
| RGGRVCYCRGRFCVCV* | | <0.97 |
| WLCYCRRRFCVCV | | 1.87 |

* Peptides not ed with * are acid forms; all others are amide forms.
Initial inoculum approximately 4 × 10⁷ CFUs/ml saliva. Peptides (3200 µg/ml) are dissolved in 0.01% acetic acid and added as 1/10 volume to saliva.

Kinetic experiments were also run using *Haemophilus influenzae* (ATCC 49247) which does not ordinarily grow on TSA, but survives several hours in LTM.

Log-phase cells (4.5×10⁵ CFUs/ml in LTM) were treated with peptide and then plated onto Chocolate agar to determine the number of viable CFUs. All peptides tested (acid and amide forms of RGGRLCYCRRRFCVCVGR, and amide form of RGGLCYCRGRFCVCVGR) were rapidly bactericidal against *H. influenzae*. No regrowth was observed at 240 minutes, as seen previously with *P. aeruginosa*.

Finally, the assay described above was conducted using *H. pylori* as the target provided the results shown in Table 26.

TABLE 26

Effect of peptide (32 μg/ml) on CFUs of Helicobacter pylori (ATCC 33591) in LTM after 15 minutes exposure

| Sequence | | Log reduction CFUs |
|---|---|---|
| RGGRLCYCRRRFCVCVGR | | 2.90 |
| RGWGLCYCRPRFCVCVGR | | 3.43 |
| RLCYCRPRFCVCVGR | | 1.34 |
| RGGGLCYTRPRFTVCVGR | | <1.12 |
| RGGGLCYARKGFAVCVGR | | <1.2 |
| RGGRLCYCRRRFCVCVGR* | | 3.00 |
| LCYCRGRFCVCVGR | | <1.12 |
| RGWRACYCRPRFCACVGR | | <1.6 |
| XCYCRRRFCVCV | (X = Cha) | <1.70 |
| WLCYCRRRFCVCV* | | <1.6 |
| RLCYCRXRFCVCV | (X = MeGly) | 1.57 |
| RLCYCRPRFCVCVGR* | | <1.6 |
| RXCFCRPRFCVCV | (X = Cha) | >4.66 |
| RGGRLCYCRRRFCVC | | <1.2 |
| LCYTRRRFTVCV | | <1.28 |
| RLCYCRRRFCVCV* | | <1.2 |
| RXRLCYCRZRFCVCV | (X = Cha)<br>(Z = MeGly) | 1.97 |
| RGWRLCYCRGRXCVCV | (X = Cha) | <1.47 |
| RGLRXCYCRGRFCVCVGR | (X = Cha) | 3.22 |
| RGGLCYCRGRFCVCVGR | | 1.57 |
| RLLRLCYCRXRFCVCVGR | (X = MeGly) | 2.10 |
| RLLRACYCRXRFCVCVGR | (X = MeGly) | 1.42 |
| RGGRLCYCRGRFCVCVGR* | | 2.40 |
| RGLRXCYCRGRFCVCVGR* | (X = Cha) | <1.47 |
| RGWRLCYCRGRFCVCVGR | | >3.57 |
| RGGRVCYCRGRFCVCV* | | <1.47 |
| WLCYCRRRFCVCV | | 3.36 |
| WLCFCRRRFCVCV | | 1.97 |
| FLCFCRRRFCVCV | | 1.99 |
| WYCYCRRRFCVCV | | <1.6 |
| WXCYCRRRFCVCV | (X = Cha) | <1.6 |
| WLCYCRRRFCVCVGR | | <1.67 |
| WXCYCRRRFCVCVGR | (X = Cha) | <1.67 |

TABLE 26-continued

Effect of peptide (32 μg/ml) on CFUs of Helicobacter pylori (ATCC 33591) in LTM after 15 minutes exposure

| Sequence | | Log reduction CFUs |
|---|---|---|
| RLLRLCYCRRRFCVCVGR | | <1.67 |
| RGGRLCYCRRRFCXCVGR | (X = MeVal) | <1.67 |

Initial inoculum approximately $4 \times 10^5$ CFUs/ml.
Peptides denoted with * are acid forms; all others are amide forms.

The modified NCCLS assay was also used as described above, where the minimum inhibitory concentration (μg/ml) is reported in Tables 28 and 29. Peptides were prepared in 0.01% AA with (+HSA) or without (−HSA) human serum albumin at 0.1%. Table 28 shows the results of various peptides tested against various organisms; Table 29 shows the results in the presence of human serum albumin. Generally, the HSA decreased the MICs, putatively by preventing absorption to the plastic surfaces.

TABLE 28

Minimum Inhibitory Concentration (μg/ml) for peptides tested in the modified NCCLS assay

| Sequence | P. aeruginosa | MRSA | VREF |
|---|---|---|---|
| RGGRLCYCRRRFCVCVGR | 8.00 | 8.00 | 2.00 |
| RGWGLCYCRPRFCVCVGR | 16.00 | 16.00 | |
| RGGRLCYCRRRFCVCVGR* | 8.00 | 16.00 | 2.00 |
| WLCYCRRRFCVCV* | 32.0 | 32.00 | |
| RGGLCYCRGRFCVCVGR | 4.00 | 8.00 | 2.00 |
| RLLRLCYCRXRFCVCVGR<br>(X = MeGly) | 16.00 | 16.00 | |
| WLCYCRRRFCVCV | 128.00 | 16.00 | 3.00 |
| WYCYCRRRFCVCV | 32.0 | 64.00 | |
| WLCYCRRRFCVCVGR | >64 | 64.00 | |
| RLLRLCYCRRRFCVCVGR | 32.0 | 32.00 | |
| RGGRLCYCRRRFCXCVGR<br>(X = MeVal) | 64.0 | >128 | |

* Peptides noted with * are acid forms; all others are amide forms.
Peptides were prepared in 0.01% acetic acid without HSA.

TABLE 29

MICS (μg/ml) in Mueller Hinton Media

| Organism | Medium Suppl. | RGGLCYCRGRFCVCVGR (amide) − HSA | RGGLCYCRGRFCVCVGR (amide) + HSA | PG-1 (amide) − HSA | PG-1 (amide) + HSA | PG-1 (acid) − HSA |
|---|---|---|---|---|---|---|
| Staphylococcus aureus MSSA | None | 4 | | 4 | | 4 |
| Staphylococcus aureus MRSA | None | 13.3 | 2 | 16 | 5.3 | 16 |
| Enterococcus faecium VREF | None | 2 | 0.33 | 1.3 | 0.25 | 2 |
| | − hematin | | 1 | | | |
| | + hematin | | 8 | | | |
| Bacillus subtilis | None | 0.7 | | 0.8 | | 0.2 |
| Streptococcus pneumoniae* | − hematin | | 2 | | | |
| | + hematin | | 8 | | | |
| Streptococcus salivarius* viridans group | − hematin | | 0.12 | | | |
| | + hematin | | 0.5 | | | |
| Pseudomonas aeruginosa | None | 4 | 1.33 | 5.3 | 0.33 | 9.3 |
| Klebsiella pneumoniae | None | 5.3 | | 4 | | 4 |
| Serratia marcescens | None | 16 | | 16 | | 21 |
| Escherichia coli | None | 4 | 0.33 | 5.3 | 0.12 | 4 |
| | − hematin | | 0.5 | | | |
| | + hematin | | 8 | | | |
| Haemophilus influenzae* | − hematin | | No growth | | | |
| | + hematin | | 8 | | | |
| Acinetobacter calocoaceticus | None | 2 | | 3 | | 4 |
| Neisseria meningitidis* | − hematin | | 8 | | | |
| | + hematin | | 32 | | | |
| Candida albicans | None | 8 | 4 | 16 | 8 | 16 |

Table 30 shows the MICs of various peptides against a variety of microorganisms.

TABLE 30

MICs of Various Peptides

| SEQUENCE | MRSA | Psa | VREF | Can. |
|---|---|---|---|---|
| RGGRLCYCRRRFCVCVGR | 2–4 | 0.3–1.7 | 0.13 | 8, 16 |
| WLCFCRRRFCVCV | | | | |
| FLCFCRRRFCVCV | 5.3 | >32 | 0.5 | 128 |
| WYCYCRRRFCVCV* | 42.7 | 32 | 1 | >128 |
| WXCYCRRRFCVCV* (X = Cha) | | | | |
| WLCYCRRRFCVCVGR* | 27–32 | 32–53 | 0.25–0.5 | >128 |
| WXCYCRRRFCVCVGR* (X = Cha) | | | | |
| RLLRCYCRRRFCVCVGR | 32† | 32† | | |
| RGGRLCYCRRRFCXCVGR (X = MeVal) | >128† | 64† | | |
| RGVCVCFRRRCYCLW | | | | |
| RGVCVCFRRRCYCLW | 10.7 | >32 | 0.5 | 32 |
| VCVCFRRRCYCLW | 16 | >32 | 1 | >128 |
| FCVCFRRRCFCLF | 16 | >32 | 2 | >128 |
| RGVCVCFRRRCYCRGGR | 8 | 8 | 0.25 | 16 |
| RGVCVCFRRRCYCLRGGR (all D) | 21 | 8 | 4 | 32 |
| RGVCVCFRRRCYCLW* | 53 | >32 | 2 | 128 |
| RGVCVCFRXRCYCLW (X = MeGly) | 13 | 32 | 1 | 64 |
| WLCYCRXZYCVCVGR (X = MeGly) (Z = D-Arg) | | | | |
| RGFCVCFRRVCYCLW | >32 | 128 | 2 | >128 |
| WLCYCRRRFCVCVGR | 11 | 48 | 0.21 | 128 |
| WLCYCRRXFCVCVR (X = D-Arg) | 5.3 | 32 | 0.25 | 64 |
| WLCYCKKKFCVCVGK | 6.7 | 4.3 | 0.21 | 32 |
| Octyl-WLCYCRRRFCVCVGR | | | | |
| XLCYCRRRFCVCV (X = 1-Nal) | 4 | 128 | 0.5 | >128 |
| WLCRGRFCVR* | >128 | >128 | >32 | >128 |
| WLCRGRFCFR | >128 | >128 | 16 | >128 |
| WLCYRRVCVR | 64 | 32 | 16 | 16 |

TABLE 30-continued

MICs of Various Peptides

| SEQUENCE | MICs (μg/mL) | | | |
|---|---|---|---|---|
| | MRSA | Psa | VREF | Can. |
| WLCYCOOOFCVCV | 2 | 4 | 0.5 | 64 |
| WLCYCXXXFCVCV (X = Dab) | 2 | 2 | 0.5 | 32 |
| WLCYCRRRFCVCV (all D) | 1 | 8 | 0.5 | 128 |
| HWRLCYCRPKFCVCV | 13.3 | 32 | 1 | >128 |
| KWRLCYCRPKFCVCV | 1 | 4 | 0.5 | 128 |
| OWRLCYCRPKFCVCV | 1 | 4 | 0.25 | 128 |
| XWRLCYCRPKFCVCV (X = Dbu) | 2.67 | 5.3 | 0.25 | 107 |
| RWHLCYCRPKFCVCV | 4.3 | 13.3 | 0.25 | >128 |
| RWKLCYCRPKFCVCV | 2 | 13.3 | 0.5 | 107 |
| RWOLCYCRPKFCVCV | 1 | 2.7 | 0.25 | 43 |
| RWXLCYCRPKFCVCV (X = Dbu) | 2 | 2 | 0.5 | 64 |
| WLCYCKXKFCVCVGR (X = Tic) | | | | |
| FCYCKXKFCYCV (X – Hyp) | | | | |
| WLXYXRRRFXVXV (X = hCys) | 16 | 64 | | |
| WOLCYCOXOFCVCVO | 1 | 2 | | |

TABLE 30-continued

MICs of Various Peptides

| SEQUENCE | MICs (μg/mL) | | | |
|---|---|---|---|---|
| | MRSA | Psa | VREF | Can. |
| (X = Tic) | | | | |
| OFCVCVOXOFCVCVO (X = Tic) | 16 | 85 | | |
| OWOLCYCOXOFCVCV (X = Tic) | 4 | 11 | | |
| OFCVCXOLCYCFO (X = Tic) | 32 | >128 | | |
| WLCYCKKKFCVCV | 2 | 5.3 | | |
| OWOLCYCOXOFCVCV (X = Hyp) | 1 | 2.3 | | |
| WLCYCOXOFCVCVO (X = Pba) | | | | |
| WLCYCOOOFCVCV (all D) | | | | |
| XFCYCLRXFCVCVR* (X = D-Arg) | 8 | 48 | | |
| WLCYCRRXFCVCVZX* (X = D-Arg) (Z = MeGly) | 64 | 48 | | |

* Peptides denoted with * are acid forms; all others are amide forms
MRSA is methicillin-resistant *S. aureus*
Psa is *P. aeruginosa*
VREF is Vancomycin-resistant *E. faecium*
Can is *C. albicans*
† denotes no HSA or BSA in assay

---

What is claimed is:

1. An antimicrobial peptide comprising about 10–30 amino acid residues and containing an amino acid sequence having the formula:

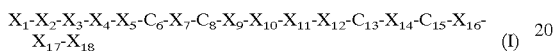

$$X_1\text{-}X_2\text{-}X_3\text{-}X_4\text{-}X_5\text{-}C_6\text{-}X_7\text{-}C_8\text{-}X_9\text{-}X_{10}\text{-}X_{11}\text{-}X_{12}\text{-}C_{13}\text{-}X_{14}\text{-}C_{15}\text{-}X_{16}\text{-}X_{17}\text{-}X_{18} \quad (I)$$

or a pharmaceutically acceptable salt or N-terminal acylated or C-terminal amidated or esterified form thereof, wherein:

each of $C_8$ and $C_{13}$ is independently present or not present, and if present each is independently a cysteine-like, basic, small, polar/large or hydrophobic amino acid;

each of $C_6$ and $C_{15}$ is independently a cysteine-like, basic, small, polar/large or hydrophobic amino acid;

each of $X_1$–$X_5$ is independently present or not present, and if present each is independently a basic, hydrophobic, polar/large, or small amino acid;

each of $X_7$ and $X_{14}$ is independently a hydrophobic or a small amino acid;

each of $X_9$ and $X_{12}$ is independently present or not present;

$X_9$–$X_{12}$ taken together are capable of effecting a reverse turn when contained in the amino acid sequence of formula (I) and at least one of $X_9$–$X_{12}$ must be a basic amino acid;

each of $X_{16}$–$X_{18}$ is independently present or not present, and if present each is independently a basic, hydrophobic, polar/large or small amino acid;

and wherein compounds containing the sequence of formula (I) comprise at least about 15%, and no more than about 50%, basic amino acids such that said antimicrobial peptide has a net charge of at least +1 at physiological pH;

with the proviso that if all of $X_1$–$X_4$ are present and none of $X_1$–$X_4$ is a hydrophobic amino acid, then at least one of $X_5$, $C_8$, $X_9$, $X_{12}$, or $C_{13}$ must be absent or $X_5$ must be basic.

2. The antimicrobial peptide of claim 1, wherein said peptide contains two disulfide bridges and is in the native form.

3. The antimicrobial peptide of claim 1, wherein said peptide contains one disulfide bridge and is in the bullet or kite form.

4. The antimicrobial peptide of claim 1, wherein said peptide contains no disulfide bridges and is in the snake form.

5. The antimicrobial peptide of claim 1, wherein said peptide has a net charge of at least about +3 at physiological pH.

6. The antimicrobial peptide of claim 1, wherein said peptide comprises about 10–24 amino acid residues and wherein:

each of $C_8$ and $C_{13}$ is independently present or not present, and if present each is independently a small, hydrophobic or polar/large amino acid or cysteine;

each of $C_6$ and $C_{15}$ is independently a small, hydrophobic or polar/large amino acid or cysteine;

each of $X_1$–$X_5$ is independently present or not present, and if present each is independently a basic or small amino acid and any two of $X_1$–$X_5$ may be a hydrophobic amino acid;

each of $X_7$ and $X_{14}$ is independently a hydrophobic amino acid;

each of $X_9$ and $X_{12}$ is independently present or not present, and if present each is independently a basic or hydrophobic amino acid;

$X_{10}$ is a basic, hydrophobic or small amino acid or proline;

$X_{16}$ is present or not present, and if present is a basic, small or hydrophobic amino acid; and each of $X_{17}$ and $X_{18}$ is independently present or not present, and if present each is independently a basic or small amino acid.

7. The antimicrobial peptide of claim 1, wherein said peptide comprises about 10–18 amino acid residues and wherein:

each of $C_8$ and $C_{13}$ is independently present or not present, and if present each is independently a small, hydrophobic or polar/large amino acid or cysteine;

each of $C_6$ and $C_{15}$ is independently a small, hydrophobic or polar/large amino acid or cysteine;

each of $X_1$–$X_4$ is independently present or not present, and if present each is independently a basic or small amino acid and any one of $X_1$–$X_4$ may be a hydrophobic amino acid;

each of $X_5$ and $X_{16}$ is independently present or not present, and if present each is independently a hydrophobic or basic amino acid;

each of $X_7$ and $X_{14}$ is independently a hydrophobic amino acid;

$X_9$ is present or not present, and if present is a basic or hydrophobic amino acid;

$X_{10}$ is a basic or small amino acid or proline;

$X_{11}$ is a basic or hydrophobic amino acid;

$X_{12}$ is present or not present, and if present is a hydrophobic amino acid;

$X_{17}$ present or not present, and if present is a small amino acid; and $X_{18}$ is present or not present, and if present is a basic amino acid.

8. The antimicrobial peptide of claim 1, wherein $C_6$, $C_8$, $C_{13}$ and $C_{15}$ are each cysteine and $X_7$ and $X_{14}$ are each independently hydrophobic amino acids.

9. The antimicrobial peptide of claim 8, wherein $X_7$ and $X_{14}$ are each independently I, V, L, W, Y or F.

10. The antimicrobial peptide of claim 9, wherein $X_7$ is I, F, Y or W and $X_{14}$ is I, V, L, W, Y or F.

11. The antimicrobial peptide of claim 1, wherein $X_1$–$X_4$ are not present.

12. The antimicrobial peptide of claim 11 which is selected from the group consisting of:

| | |
|---|---|
| VCVCFRRRCYCLW | (SEQ ID NO:12); |
| FCVCFRRRCFCLF | (SEQ ID NO:13); |
| FCYCKXKFCYCV (X = Hyp) | (SEQ ID NO:40); |
| LCYCRRRFCVCVGR | (SEQ ID NO:52); |
| RCYCRRRFCVCV | (SEQ ID NO:53); |
| RCYCRRRFCVCR | (SEQ ID NO:55); |
| LCYCRRRFCVCV | (SEQ ID NO:56); |
| LCYARRRFAVCV | (SEQ ID NO:57); |
| RCYARRRFAVCR | (SEQ ID NO:58); |
| LAYCRRRFCVAV | (SEQ ID NO:59); |
| RAYCRRRFCVAR | (SEQ ID NO:60); |
| CYCRRRFCVCV | (SEQ ID NO:68); |
| CYCRRRFCVCVGR | (SEQ ID NO:72); |
| LCYCRRRFCVC | (SEQ ID NO:74); |
| LCYTRRRFTVCV | (SEQ ID NO:75); |
| LTYCRRRFCVTV | (SEQ ID NO:76); |
| RCYCRRRFCVCV | (SEQ ID NO:87); |
| LCYCRRRFCVCR | (SEQ ID NO:88); |
| VCYCFRRRFCYCV | (SEQ ID NO:89); |
| LCYTRPRFTVCV | (SEQ ID NO:90); |
| LCYTRGRFTVCV | (SEQ ID NO:91); |
| LCYFRRRFIVCV | (SEQ ID NO:92); |
| LCYFRPRFIVCV | (SEQ ID NO:93); |
| LCYTFRPRFVCV | (SEQ ID NO:94); |
| LCYTFRGRFVCV | (SEQ ID NO:95); |
| CYCFRRRFCVC | (SEQ ID NO:96); |
| LCYCRRRRCVCV | (SEQ ID NO:97); |
| LCYCFRRRCVCV | (SEQ ID NO:98); |
| LCYCRFRRCVCV | (SEQ ID NO:99); |
| LCYCRRFRCVCV | (SEQ ID NO:100); |
| LCYCRRFFCVCV | (SEQ ID NO:101); |
| LCYCRFFRCVCV | (SEQ ID NO:102); |
| LCYCFFRRCVCV | (SEQ ID NO:103); |
| LCYCFRRFCVCV | (SEQ ID NO:104); |
| LCYCFRFRCVCV | (SEQ ID NO:105); |
| LCYCRFRFCVCV | (SEQ ID NO:106); |
| LCYCFRFFCVCV | (SEQ ID NO:107); |
| LCYCFFRFCVCV | (SEQ ID NO:108); |
| LCYCFFFRCVCV | (SEQ ID NO:109); |
| LCYCFFFFCVCV | (SEQ ID NO:110); |
| YCYCRRRFCVCVGR | (SEQ ID NO:112); |
| ICYCRRRFCVCVGR | (SEQ ID NO:113); |
| FCYCRRRFCVCVGR | (SEQ ID NO:114); |
| WCYCRRRFCVCVGR | (SEQ ID NO:115); |
| RCYCRRRFCVCVGR | (SEQ ID NO:116); |
| LCYTRGRFTVCVR | (SEQ ID NO:118); |
| LCYCHHHFCVCV | (SEQ ID NO:120); |
| LCYTHHHFTVCV | (SEQ ID NO:121); |
| LCYCRRRFCVCV | (SEQ ID NO:155); |
| LCYCRRCFCVCV | (SEQ ID NO:156); |
| LCYCRRRFCVCF | (SEQ ID NO:157); |
| LCACRRRACVCV | (SEQ ID NO:158); |
| LCYCRXRFCVCV (X = D-Arg) | (SEQ ID NO:159); |
| LCWCRRRFCVCV | (SEQ ID NO:160); |
| WCYCRRRFCVCV | (SEQ ID NO:161); |
| LCYCRRRXCVCV (X = hPhe) | (SEQ ID NO:162); |
| LCYCRRRXCVCV (X = Phe(4-Cl)) | (SEQ ID NO:163); |
| XCYCRRRFCVCV (X = Cha) | (SEQ ID NO:164); |
| LCYCRRRFCXCV (X = D-His) | (SEQ ID NO:165); |
| LCYCRRRXCVCV (X = MeGly) | (SEQ ID NO:166); |
| LCYCRRRXCVCV (X = MePhe) | (SEQ ID NO:167); |
| LCYCRRRFCXCV (X = MeVal) | (SEQ ID NO:168); |
| LCXCRRRXCVCV (X = Cha) | (SEQ ID NO:169); |
| LCGCRRRGCVCV | (SEQ ID NO:170); |
| LCACRGRACVCV | (SEQ ID NO:171); |
| CYCRRRFCVCF | (SEQ ID NO:201); |
| LCYCRPRFCVCVGR | (SEQ ID NO:204); |
| LCYCKPKFCVCVGK | (SEQ ID NO:205); |
| LCYCRGRFCVCVGR | (SEQ ID NO:206); |
| LCYCRPRFCVCVGRGR | (SEQ ID NO:207); |
| LCYCRXRFCVCV (X = D-Ala) | (SEQ ID NO:217); |
| LCYCKPKFCVCV | (SEQ ID NO:218); |
| VCYCRPRFCVCV | (SEQ ID NO:219); |
| LCYCRPRFCVCW | (SEQ ID NO:220); |
| LCYRRPRFRVCV | (SEQ ID NO:221); |
| LCYKRGRFKVCV | (SEQ ID NO:236); |
| ICYRPRFVCVGR | (SEQ ID NO:237); and | the N-terminal acylated and C-terminal amidated or esterified forms thereof.

13. The antimicrobial peptide of claim 1, wherein at least one of $X_1$–$X_4$ is a hydrophobic amino acid.

14. The antimicrobial peptide of claim 13 which is selected from the group consisting of:

| | |
|---|---|
| WLCFCRRRFCVCV | (SEQ ID NO:2); |
| FLCFCRRRFCVCV | (SEQ ID NO:3); |
| WYCYCRRRFCVCV | (SEQ ID NO:4); |
| WXCYCRRRFCVCV (X = Cha) | (SEQ ID NO:5); |
| WLCYCRRRFCVCVGR | (SEQ ID NO:6); |
| WXCYCRRRFCVCVGR (X = Cha) | (SEQ ID NO:7); |
| RLLRLCYCRRRFCVCVGR | (SEQ ID NO:8); |
| WLCYCRXZYCVCVGR (X = MeGly) (Z = D-Arg) | (SEQ ID NO:18); |
| WLCYCRRRFCVCVGR | (SEQ ID NO:20); |
| WLCYCRRXFCVCVR (X = D-Arg) | (SEQ ID NO:21); |
| WLCYCKKKFCVCVGK | (SEQ ID NO:22); |
| XLCYCRRRFCVCV (X = 1-Nal) | (SEQ ID NO:24); |
| WLCRGRFCVR | (SEQ ID NO:25); |
| WLCRGRFCFR | (SEQ ID NO:26); |
| WLCYRRVCVR | (SEQ ID NO:27); |
| WLCYCOOOFCVCV | (SEQ ID NO:28); |
| WLCYCXXXFCVCV (X = Dab) | (SEQ ID NO:29); |
| WLCYCRRRFCVCV (all D) | (SEQ ID NO:30); |
| HWRLCYCRPKFCVCV | (SEQ ID NO:31); |
| KWRLCYCRPKFCVCV | (SEQ ID NO:32); |
| OWRLCYCRPKFCVCV | (SEQ ID NO:33); |
| XWRLCYCRPKFCVCV (X = Dab) | (SEQ ID NO:34); |
| RWHLCYCRPKFCVCV | (SEQ ID NO:35); |
| RWKLCYCRPKFCVCV | (SEQ ID NO:36); |
| RWOLCYCRPKFCVCV | (SEQ ID NO:37); |
| RWXLCYCRPKFCVCV (X = Dab) | (SEQ ID NO:38); |
| WLCYCKXKFCVCVGR (X = Tic) | (SEQ ID NO:39); |
| WLXYXRRRFXVXV (X = hCys) | (SEQ ID NO:41); |
| WOLCYCOXOFCVCVO (X = Tic) | (SEQ ID NO:42); |
| OWOLCYCOXOFCVCV (X = Tic) | (SEQ ID NO:44); |
| WLCYCKKKFCVCV | (SEQ ID NO:46); |
| OWOLCYCOXOFCVCV (X = Hyp) | (SEQ ID NO:47); |
| WLCYCOXOFCVCVO (X = Pba) | (SEQ ID NO:48); |
| WLCYCOOOFCVCV (all D) | (SEQ ID NO:49); |
| WLCYCRRXFCVCVZX (X = D-Arg) (Z = MeGly) | (SEQ ID NO:51); |
| RGWRLCYCRRRFCVCV | (SEQ ID NO:71); |
| RGWRLCYCRRRFCVCVGR | (SEQ ID NO:85); |
| RGWRLAYCRRRFCVAVGR | (SEQ ID NO:86); |
| RGWGLCYCRPRFCVCVGR | (SEQ ID NO:134); |
| RGWRLCYCRXRFCVCVGR (X = MeGly) | (SEQ ID NO:135); |
| RGWRLCYCRGRFCVCVGR | (SEQ ID NO:136); |
| RGWRLCYCXPRFCVCVGR (X = Cit) | (SEQ ID NO:137); |
| RWRLCYCRPRFCVCVGR | (SEQ ID NO:138); |
| RGWRLCYCRPRFCVCVGR | (SEQ ID NO:139); |
| RGWRACYCRPRFCACVGR | (SEQ ID NO:140); |
| GWRLCYCRPRFCVCVGR | (SEQ ID NO:141); |
| RWRLCYCKGKFCVCVGR | (SEQ ID NO:142); |
| RGWRLCYCRXRFCVCVGR (X = MeGly) | (SEQ ID NO:143); |
| GGWRLCYCRGRFCVCVGR | (SEQ ID NO:144); |
| RGGWLCYCRGRFCVCVGR | (SEQ ID NO:145); |
| RLLRLCYCRXRFCVCVGR (X = MeGly) | (SEQ ID NO:146); |
| RLLRACYCRXRFCVCVGR (X = MeGly) | (SEQ ID NO:147); |
| RLLRLCYCRRRFCVCVGR | (SEQ ID NO:148); |
| RGLRXCYCRGRFCVCVGR (X = Cha) | (SEQ ID NO:149); |
| RGLRXCYCRGRFCVCVGR (X = Cha) | (SEQ ID NO:152); |

-continued

| Sequence | SEQ ID |
|---|---|
| WLCYCRRRFCVCV | (SEQ ID NO:180); |
| WLCFCRRRFCVCV | (SEQ ID NO:181); |
| FLCFCRRRFCVCV | (SEQ ID NO:182); |
| WLCFCRRRXCVCV (X = MePhe) | (SEQ ID NO:183); |
| WYCYCRRRFCVCV | (SEQ ID NO:184); |
| WXCYCRRRFCVCV (X = Cha) | (SEQ ID NO:185); |
| XLCFCRRRZCVCV (X = Cha) (Z = MePhe) | (SEQ ID NO:187); |
| WLCYCRRRFCVCVGR | (SEQ ID NO:189); |
| WXCYCRRRFCVCVGR (X = Cha) | (SEQ ID NO:190); |
| RWRCYCGRRFCGCVGR | (SEQ ID NO:194); |
| GWRCYCRGRFCGC | (SEQ ID NO:196); |
| RGWACYCRGRFCVC | (SEQ ID NO:197); |
| RGWRLCYGRGRFKVC | (SEQ ID NO:199); |
| RGWRLCYCRGRFCVC | (SEQ ID NO:200); |
| RGWRLCYCRXRFCVC (X = MeGly) | (SEQ ID NO:202); |
| RGWRGCYCRXRFCGC (X = MeGly) | (SEQ ID NO:203); |
| WRLCYCRPRFCVCVGR | (SEQ ID NO:209); |
| GWLCYCRGRFCVCVGR | (SEQ ID NO:210); |
| RWLCYCRGRFCVCVGR | (SEQ ID NO:211); |
| RLLCYCRGRFCVCVGR | (SEQ ID NO:212); |
| RWRLCYCRPRFCVCV | (SEQ ID NO:213); |
| RXRLCYCRZRFCVCV (X = Cha) (Z = MeGly) | (SEQ ID NO:214); |
| RGWRLCYCRGRXCVCV (X = Cha) | (SEQ ID NO:215); |
| RGWRLCYCRGRXCVCV (X = Cha) | (SEQ ID NO:222); |
| RXRLCYCRZRFCVCV (X = Cha) (Z = MeGly) | (SEQ ID NO:223); |
| RXRLCYCRGRFCVCV (X = Cha) | (SEQ ID NO:224); |
| RGWRGCYKRGRFKGCVGR | (SEQ ID NO:235); |
| WLCYCRRRFCVCV | (SEQ ID NO:238); and | the N-terminal acylated and C-terminal amidated or esterified forms thereof.

15. The antimicrobial peptide of claim 1 in which at least one of $X_1$–$X_4$ or $C_8$ or $C_{13}$ is not present.

16. The antimicrobial peptide of claim 15 which is selected from the group consisting of:

| Sequence | SEQ ID |
|---|---|
| RGVCVCFRRRCYCLW | (SEQ ID NO:10); |
| RGVCVCFRRRCYCRGGR | (SEQ ID NO:14); |
| RGVCVCFRRRCYCLRGGR (all D) | (SEQ ID NO:15); |
| RGVCVCFRRRCYCLW | (SEQ ID NO:16); |
| RGVCVCYRXRCYCLW (X = MeGly) | (SEQ ID NO:17); |
| RGFCVCFRRVCYCLW | (SEQ ID NO:19); |
| OFCVCVOXOFCVCVO (X = Tic) | (SEQ ID NO:43); |
| OFCVCXOLCYCFO (X = Tic) | (SEQ ID NO:45); |
| XFCYCLRXFCVCVR (X = D-Arg) | (SEQ ID NO:50); |
| RGGRLCY RR VCV | (SEQ ID NO:61); |
| GGRLCYCRRRFCVCV | (SEQ ID NO:62); |
| RGRLCYCRRRFCVCV | (SEQ ID NO:63); |
| GRLCYCRRRFCVCV | (SEQ ID NO:64); |
| RRLCYCRRRFCVCV | (SEQ ID NO:65); |
| RLCYCRRRFCVCV | (SEQ ID NO:66); |
| RRCYCRRRFCVCV | (SEQ ID NO:67); |
| RGGRLCY RRRF VCV | (SEQ ID NO:70); |
| GGRLCYCRRRFCVCVGR | (SEQ ID NO:77); |
| RGRLCYCRRRFCVCVGR | (SEQ ID NO:78); |
| GRLCYCRRRFCVCVGR | (SEQ ID NO:79); |
| RRLCYCRRRFCVCVGR | (SEQ ID NO:80); |
| RLCYCRRRFCVCVGR | (SEQ ID NO:81); |
| RRCYCRRRFCVCVGR | (SEQ ID NO:82); |
| RGGRLCY RRRF VCVGR | (SEQ ID NO:84); |
| RGGRLCY RR VCVGR | (SEQ ID NO:111); |
| RLCYTRGRFTVCV | (SEQ ID NO:117); |
| RLCYTRGRFTVCVR | (SEQ ID NO:119); |
| RGGLCYCRRRFCVCVGR | (SEQ ID NO:122); |
| RGGLCYCRGRFCVCVGR | (SEQ ID NO:129); |
| RACYCRPRFCACV | (SEQ ID NO:172); |
| RLCYCRPRFCVCF | (SEQ ID NO:173); |
| RLCYCRPRFCVCV | (SEQ ID NO:174); |
| KLCYCKPKFCVCV | (SEQ ID NO:175); |
| RLCACRGRACVCV | (SEQ ID NO:176); |
| RLCYCRXRFCVCV (X = MeGly) | (SEQ ID NO:177); |
| RXCFCRPRFCVCV (X = Cha) | (SEQ ID NO:178); |
| RWCFCRPRFCVCV | (SEQ ID NO:179); |
| RXCYCRGRZCVCV (X = Cha) (Z = MePhe) | (SEQ ID NO:186); |
| RLCYCRPRFCVCVGR | (SEQ ID NO:188); |
| RLCYCRGPFCVCR | (SEQ ID NO:191); |
| RRWCFVCYAGFCYRCR | (SEQ ID NO:192); |
| RRCYCRGRFCGCVGR | (SEQ ID NO:193); |
| RARCYCGRRFCGCVGR | (SEQ ID NO:195); |
| RRCYGRRRFGVCVGR | (SEQ ID NO:198); |
| RRWCYCRPRFCVCVR | (SEQ ID NO:208); |
| RLCYCRRRFCVCV | (SEQ ID NO:240); |
| RRRLCYCRRRFCVCVGR | (SEQ ID NO:242); and | the N-terminal acylated and C-terminal amidated or esterified forms thereof.

17. The antimicrobial peptide of claim 16 which is the C-terminal amidated form of SEQ ID NO:129.

18. The antimicrobial peptide of claim 17 which is in the native form.

19. The antimicrobial peptide of claim 13, wherein said hydrophobic amino acid is I, V, L, W, F or Y.

20. The antimicrobial peptide of claim 1, wherein at least one of $X_9$–$X_{12}$ is a hydrophobic amino acid.

21. The antimicrobial peptide of claim 1, wherein $X_1$ and $X_9$ are each independently R, K, Orn, Dab, Har or a hydrophobic amino acid.

22. The antimicrobial peptide of claim 1, wherein $X_2$ and $X_3$ are each independently G, A, S, T, I, V, L, F, Y or W.

23. The antimicrobial peptide of claim 1, wherein $X_4$ is R, K, H, Orn, Dab, G, A, S, T, F, Y or W.

24. The antimicrobial peptide of claim 1, wherein $X_9$ is R, K, H, Orn, Dab, Har, I, V, 1, Nle, W, Y or F and $X_{12}$ is I, L, V, W, F or Y.

25. The antimicrobial peptide of claim 1, wherein $X_9$–$X_{12}$, taken together are a three amino acid residue γ-turn.

26. The antimicrobial peptide of claim 1, wherein $X_9$–$X_{12}$ taken together are a four amino acid residue β-turn.

27. The antimicrobial peptide of claim 1, wherein said reverse turn is ZZZG, ZZZF, ZZSG, ZZAL, ZGZL, ZFZL, ZPZV, ZPZF, ZGZY, IZGZ, LZZF or YZGZ, wherein each Z is independently an L- or D-entantiomer of R, K, Dbu or Orn.

28. The antimicrobial peptide of claim 1, wherein all of the amino acids are D-enantiomers.

29. An antimicrobial peptide selected from the group consisting of:

| | | |
|---|---|---|
| | WLCFCRRRFCVCV | (SEQ ID NO:2); |
| | FLCFCRRRFCVCV | (SEQ ID NO:3); |
| | WYCYCRRRFCVCV | (SEQ ID NO:4); |
| | WXCYCRRRFCVCV (X = Cha) | (SEQ ID NO:5); |
| | WLCYCRRRFCVCVGR | (SEQ ID NO:6); |
| | WXCYCRRRFCVCVGR (X = Cha) | (SEQ ID NO:7); |
| | RLLRLCYCRRRFCVCVGR | (SEQ ID NO:8); |
| | RGVCVCFRRRCYCLW | (SEQ ID NO:10); |
| | RGVCVCFRRRCYCLW | (SEQ ID NO:11); |
| | VCVCFRRRCYCLW | (SEQ ID NO:12); |
| | FCVCFRRRCFCLF | (SEQ ID NO:13); |
| | RGVCVCFRRRCYCRGGR | (SEQ ID NO:14); |
| | RGVCVCFRRRCYCLRGGR (all D) | (SEQ ID NO:15); |
| | RGVCVCFRRRCYCLW | (SEQ ID NO:16); |
| | RGVCVCYRXRCYCLW (X = MeGly) | (SEQ ID NO:17); |
| | WLCYCRXZYCVCVGR (X = MeGly) (Z = D-Arg) | (SEQ ID NO:18); |
| | RGFCVCFRRVCYCLW | (SEQ ID NO:19); |
| | WLCYCRRRFCVCVGR | (SEQ ID NO:20); |
| | WLCYCRRXFCVCVR (X = D-Arg) | (SEQ ID NO:21); |
| | WLCYCKKKFCVCVGK | (SEQ ID NO:22); |
| | XLCYCRRRFCVCV (X = 1-Nal) | (SEQ ID NO:24); |
| | WLCRGRFCVR | (SEQ ID NO:25); |
| | WLCRGRFCFR | (SEQ ID NO:26); |
| | WLCYRRVCVR | (SEQ ID NO:27); |
| | WLCYCOOOFCVCV | (SEQ ID NO:28); |
| | WLCYCXXXFCVCV (X = Dab) | (SEQ ID NO:29); |
| | WLCYCRRRFCVCV (all D) | (SEQ ID NO:30); |
| | HWRLCYCRPKFCVCV | (SEQ ID NO:31); |
| | KWRLCYCRPKFCVCV | (SEQ ID NO:32); |
| | OWRLCYCRPKFCVCV | (SEQ ID NO:33); |
| | XWRLCYCRPKFCVCV (X = Dab) | (SEQ ID NO:34); |
| | RWHLCYCRPKFCVCV | (SEQ ID NO:35); |
| | RWKLCYCRPKFCVCV | (SEQ ID NO:36); |
| | RWOLCYCRPKFCVCV | (SEQ ID NO:37); |
| | RWXLCYCRPKFCVCV (X = Dab) | (SEQ ID NO:38); |
| | WLCYCKXKFCVCVGR (X = Tic) | (SEQ ID NO:39); |
| | FCYCKXKFCYCV (X = Hyp) | (SEQ ID NO:40); |
| | WLXYXRRRFXVXV (X = hCys) | (SEQ ID NO:41); |
| | WOLCYCOXOFCVCVO (X = Tic) | (SEQ ID NO:42); |
| | OFCVCVOXOFCVCVO (X = Tic) | (SEQ ID NO:43); |
| | OWOLCYCOXOFCVCV (X = Tic) | (SEQ ID NO:44); |
| | OFCVCXOLCYCFO (X = Tic) | (SEQ ID NO:45); |
| | WLCYCKKKFCVCV | (SEQ ID NO:46); |
| | OWOLCYCOXOFCVCV (X = Hyp) | (SEQ ID NO:47); |
| | WLCYCOXOFCVCVO (X = Pba) | (SEQ ID NO:48); |
| | WLCYCOOOFCVCV (all D) | (SEQ ID NO:49); |
| | XFCYCLRXFCVCVR (X = D-Arg) | (SEQ ID NO:50); |
| | WLCYCRRXFCVCVZX (X = D-Arg) (Z = MeGly) | (SEQ ID NO:51); |
| PC11 | LCYCRRRFCVCVGR | (SEQ ID NO:52); |
| PC12 | RCYCRRRFCVCV | (SEQ ID NO:53); |
| PC16 | RCYCRRRFCVCR | (SEQ ID NO:55); |
| PC17 | LCYCRRRFCVCV | (SEQ ID NO:56); |
| PC18 | LCYARRRFAVCV | (SEQ ID NO:57); |
| PC19 | RCYARRRFAVCR | (SEQ ID NO:58); |
| PC20 | LAYCRRRFCVAV | (SEQ ID NO:59); |
| PC21 | RAYCRRRFCVAR | (SEQ ID NO:60); |
| PC22 | RGGRLCY RR VCV | (SEQ ID NO:61); |
| PC31 | GGRLCYCRRRFCVCV | (SEQ ID NO:62); |
| PC32 | RGRLCYCRRRFCVCV | (SEQ ID NO:63); |
| PC33 | GRLCYCRRRFCVCV | (SEQ ID NO:64); |
| PC34 | RRLCYCRRRFCVCV | (SEQ ID NO:65); |
| PC35 | RLCYCRRRFCVCV | (SEQ ID NO:66); |
| PC36 | RRCYCRRRFCVCV | (SEQ ID NO:67); |
| PC37 | CYCRRRFCVCV | (SEQ ID NO:68); |
| PC44 | RGGRLCYCRRRFCVC | (SEQ ID NO:69); |
| PC47 | RGGRLCY RRRF VCV | (SEQ ID NO:70); |
| PC48 | RGWRLCYCRRRFCVCV | (SEQ ID NO:71); |
| PC37a | CYCRRRFCVCVGR | (SEQ ID NO:72); |

-continued

| | | |
|---|---|---|
| PC45 | RGGRLCYCRRRFCV | (SEQ ID NO:73); |
| PC72 | LCYCRRRFCVC | (SEQ ID NO:74); |
| PC64 | LCYTRRRFTVCV | (SEQ ID NO:75); |
| PC64a | LTYCRRRFCVTV | (SEQ ID NO:76); |
| PC31a | GGRLCYCRRRFCVCVGR | (SEQ ID NO:77); |
| PC32a | RGRLCYCRRRFCVCVGR | (SEQ ID NO:78); |
| PC33a | GRLCYCRRRFCVCVGR | (SEQ ID NO:79); |
| PC34a | RRLCYCRRRFCVCVGR | (SEQ ID NO:80); |
| PC35a | RLCYCRRRFCVCVGR | (SEQ ID NO:81); |
| PC36a | RRCYCRRRFCVCVGR | (SEQ ID NO:82); |
| PC47a | RGGRLCY RRRF VCVGR | (SEQ ID NO:84); |
| PC48a | RGWRLCYCRRRFCVCVGR | (SEQ ID NO:85); |
| PC54 | RGWRLAYCRRRFCVAVGR | (SEQ ID NO:86); |
| PC61 | RCYCRRRFCVCV | (SEQ ID NO:87); |
| PC62 | LCYCRRRFCVCR | (SEQ ID NO:88); |
| PC63 | VCYCFRRFCYCV | (SEQ ID NO:89); |
| PC65 | LCYTRPRFTVCV | (SEQ ID NO:90); |
| PC66 | LCYTRGRFTVCV | (SEQ ID NO:91); |
| PC67 | LCYFRRRFIVCV | (SEQ ID NO:92); |
| PC68 | LCYFRPRFIVCV | (SEQ ID NO:93); |
| PC69 | LCYTFRPRFVCV | (SEQ ID NO:94); |
| PC70 | LCYTFRGRFVCV | (SEQ ID NO:95); |
| PC74 | CYCFRRFCVC | (SEQ ID NO:96); |
| PC77 | LCYCRRRRCVCV | (SEQ ID NO:97); |
| PC78 | LCYCFRRRCVCV | (SEQ ID NO:98); |
| PC79 | LCYCRFRRCVCV | (SEQ ID NO:99); |
| PC80 | LCYCRRFRCVCV | (SEQ ID NO:100); |
| PC81 | LCYCRRRFCVCV | (SEQ ID NO:101); |
| PC82 | LCYCRFFRCVCV | (SEQ ID NO:102); |
| PC83 | LCYCFFRRCVCV | (SEQ ID NO:103); |
| PC84 | LCYCFRRFCVCV | (SEQ ID NO:104); |
| PC85 | LCYCFRFRCVCV | (SEQ ID NO:105); |
| PC86 | LCYCRFRFCVCV | (SEQ ID NO:106); |
| PC87 | LCYCFRFFCVCV | (SEQ ID NO:107); |
| PC88 | LCYCFFRFCVCV | (SEQ ID NO:108); |
| PC89 | LCYCFFFRCVCV | (SEQ ID NO:109); |
| PC90 | LCYCRFFFCVCV | (SEQ ID NO:100); |
| | RGGRLCY RR VCVGR | (SEQ ID NO:111); |
| PC91 | YCYCRRRFCVCVGR | (SEQ ID NO:112); |
| PC95 | ICYCRRRFCVCVGR | (SEQ ID NO:113); |
| PC96 | FCYCRRRFCVCVGR | (SEQ ID NO:114); |
| PC97 | WCYCRRRFCVCVGR | (SEQ ID NO:115); |
| PC99 | RCYCRRRFCVCVGR | (SEQ ID NO:116); |
| PC109 | RLCYTRGRFTVCV | (SEQ ID NO:117); |
| PC110 | LCYTRGRFTVCVR | (SEQ ID NO:118); |
| PC111 | RLCYTRGRFTVCVR | (SEQ ID NO:119); |
| PC112 | LCYCHHHFCVCV | (SEQ ID NO:120); |
| PC113 | LCYTHHHFTVCV | (SEQ ID NO:121); |
| | RGGLCYCRRRFCVCVGR | (SEQ ID NO:122); |
| | RGGLCYCRGRFCVCVGR | (SEQ ID NO:129); |
| | XGGRLCYCRGRFCVCVGR (X = Cit) | (SEQ ID NO:131); |
| | RGWGLCYCRPRFCVCVGR | (SEQ ID NO:134); |
| | RGWRLCYCRXRFCVCVGR (X = MeGly) | (SEQ ID NO:135); |
| | RGWRLCYCRGRFCVCVGR | (SEQ ID NO:136); |
| | RGWRLCYCXPRFCVCVGR (X = Cit) | (SEQ ID NO:137); |
| | RWRLCYCRPRFCVCVGR | (SEQ ID NO:138); |
| | RGWRLCYCRPRFCVCVGR | (SEQ ID NO:139); |
| | RGWRACYCRPRFCACVGR | (SEQ ID NO:140); |
| | GWRLCYCRPRFCVCVGR | (SEQ ID NO:141); |
| | RWRLCYCKGKFCVCVGR | (SEQ ID NO:142); |
| | RGWRLCYCRXRFCVCVGR (X = MeGly) | (SEQ ID NO:143); |
| | GGWRLCYCRGRFCVCVGR | (SEQ ID NO:144); |
| | RGGWLCYCRGRFCVCVGR | (SEQ ID NO:145); |
| | RLLRLCYCRXRFCVCVGR (X = MeGly) | (SEQ ID NO:146); |
| | RLLRACYCRXRFCVCVGR (X = MeGly) | (SEQ ID NO:147); |
| | RLLRLCYCRRRFCVCVGR | (SEQ ID NO:148); |
| | RGLRXCYCRGRFCVCVGR (X = Cha) | (SEQ ID NO:149); |
| | (Z = Cha) | |
| | (Z = Cha) | |
| | RGLRXCYCRGRFCVCVGR (X = Cha) | (SEQ ID NO:152); |
| | LCYCRRRFCVCV | (SEQ ID NO:155); |
| | LCYCRRCFCVCV | (SEQ ID NO:156); |
| | LCYCRRRFCVCF | (SEQ ID NO:157); |
| | LCACRRRACVCV | (SEQ ID NO:158); |
| | LCYCRXRFCVCV (X = D-Arg) | (SEQ ID NO:159); |
| | LCWCRRRFCVCV | (SEQ ID NO:160); |
| | WCYCRRRFCVCV | (SEQ ID NO:161); |
| | LCYCRRRXCVCV (X = hPhe) | (SEQ ID NO:162); |
| | LCYCRRRXCVCV (X = Phe(4-Cl)) | (SEQ ID NO:163); |
| | XCYCRRRFCVCV (X = Cha) | (SEQ ID NO:164); |

| | |
|---|---|
| LCYCRRRFCXCV (X = D-His) | (SEQ ID NO:165); |
| LCYCRRRXCVCV (X = MeGly) | (SEQ ID NO:166); |
| LCYCRRRXCVCV (X = MePhe) | (SEQ ID NO:167); |
| LCYCRRRFCXCV (X = MeVal) | (SEQ ID NO:168); |
| LCXCRRRXCVCV (X = Cha) | (SEQ ID NO:169); |
| LCGCRRRGCVCV | (SEQ ID NO:170); |
| LCACRGRACVCV | (SEQ ID NO:171); |
| RACYCRPRFCACV | (SEQ ID NO:172); |
| RLCYCRPRFCVCF | (SEQ ID NO:173); |
| RLCYCRPRFCVCV | (SEQ ID NO:174); |
| KLCYCKPKFCVCV | (SEQ ID NO:175); |
| RLCACRGRACVCV | (SEQ ID NO:176); |
| RLCYCRXRFCVCV (X = MeGly) | (SEQ ID NO:177); |
| RXCFCRPRFCVCV (X = Cha) | (SEQ ID NO:178); |
| RWCFCRPRFCVCV | (SEQ ID NO:179); |
| WLCYCRRRFCVCV | (SEQ ID NO:180); |
| WLCFCRRRFCVCV | (SEQ ID NO:181); |
| FLCFCRRRFCVCV | (SEQ ID NO:182); |
| WLCFCRRRXCVCV (X = MePhe) | (SEQ ID NO:183); |
| WYCYCRRRFCVCV | (SEQ ID NO:184); |
| WXCYCRRRFCVCV (X = Cha) | (SEQ ID NO:185); |
| RXCFCRGRZCVCV (X = Cha) (Z = MePhe) | (SEQ ID NO:186); |
| XLCFCRRRZCVCV (X = Cha) (Z = MePhe) | (SEQ ID NO:187); |
| RLCYCRPRFCVCVGR | (SEQ ID NO:188); |
| WLCYCRRRFCVCVGR | (SEQ ID NO:189); |
| WXCYCRRRFCVCVGR (X = Cha) | (SEQ ID NO:190); |
| RLCYCRGPFCVCR | (SEQ ID NO:191); |
| RRWCFVCYAGFCYRCR | (SEQ ID NO:192); |
| RRCYCRGRFCGCVGR | (SEQ ID NO:193); |
| RWRCYCGRRFCGCVGR | (SEQ ID NO:194); |
| RARCYCGRRFCGCVGR | (SEQ ID NO:195); |
| GWRCYCRGRFCGC | (SEQ ID NO:196); |
| RGWACYCRGRFCVC | (SEQ ID NO:197); |
| RRCYGRRRFGVCVGR | (SEQ ID NO:198); |
| RGWRLCYGRGRFKVC | (SEQ ID NO:199); |
| RGWRLCYCRGRFCVC | (SEQ ID NO:200); |
| CYCRRRFCVCF | (SEQ ID NO:201); |
| RGWRLCYCRXRFCVC (X = MeGly) | (SEQ ID NO:202); |
| RGWRGCYCRXRFCGC (X = MeGly) | (SEQ ID NO:203); |
| LCYCRPRFCVCVGR | (SEQ ID NO:204); |
| LCYCKPKFCVCVGK | (SEQ ID NO:205); |
| LCYCRGRFCVCVGR | (SEQ ID NO:206); |
| LCYCRPRFCVCVGRGR | (SEQ ID NO:207); |
| RRWCYCRPRFCVCVR | (SEQ ID NO:208); |
| WRLCYCRPRFCVCVGR | (SEQ ID NO:209); |
| GWLCYCRGRFCVCVGR | (SEQ ID NO:210); |
| RWLCYCRGRFCVCVGR | (SEQ ID NO:211); |
| RLLCYCRGRFCVCVGR | (SEQ ID NO:212); |
| RWRLCYCRPRFCVCV | (SEQ ID NO:213); |
| RXRLCYCRZRFCVCV (X = Cha) (Z = MeGly) | (SEQ ID NO:214); |
| RGWRLCYCRGRXCVCV (X = Cha) | (SEQ ID NO:215); |
| LCYCRXRFCVCV (X = D-Ala) | (SEQ ID NO:217); |
| LCYCKPKFCVCV | (SEQ ID NO:218); |
| VCYCRPRFCVCV | (SEQ ID NO:219); |
| LCYCRPRFCVCW | (SEQ ID NO:220); |
| LCYRRPRFRVCV | (SEQ ID NO:221); |
| RGWRLCYCRGRXCVCV (X = Cha) | (SEQ ID NO:222); |
| RXRLCYCRZRFCVCV (X = Cha) (Z = MeGly) | (SEQ ID NO:223); |
| RXRLCYCRGRFCVCV (X = Cha) | (SEQ ID NO:224); |
| RGGGLCYKRGFIKVCFGR | (SEQ ID NO:231); |
| RGGGLCYKRGWIKFCVGR | (SEQ ID NO:232); |
| RGGGLCYRLPKFRVCVGR | (SEQ ID NO:233); |
| RGGGLCYRLPGFRVCVGR | (SEQ ID NO:234); |
| RGWRGCYKRGRFKGCVGR | (SEQ ID NO:235); |
| LCYKRGRFKVCV | (SEQ ID NO:236); |
| ICYRPRFVCVGR | (SEQ ID NO:237); |
| WLCYCRRRFCVCV | (SEQ ID NO:238); |
| RLCYCRRRFCVCV | (SEQ ID NO:240); |
| RRRLCYCRRRFCVCVGR | (SEQ ID NO:242) | and the N-terminal acylated and C-terminal amidated or esterified forms thereof.

30. A recombinant expression system for production of the antimicrobial peptide according to claim 1, which expression system comprises a nucleotide sequence encoding said peptide operably linked to control sequences for effecting expression.

31. A recombinant host cell, or progeny thereof, modified to contain the expression system of claim 30.

32. A method of producing an antimicrobial peptide or precursor peptide therefor, said method comprising the steps of culturing the modified host cell or progeny thereof according to claim 30 under conditions wherein said peptide is produced; and recovering the antimicrobial peptide from the culture.

33. An antimicrobial pharmaceutical composition comprising an antimicrobial peptide according to claim 1 and a pharmaceutically acceptable carrier, diluent or excipient.

34. An antimicrobial environmental composition for application to plants comprising an antimicrobial peptide according to claim 1 and an environmentally acceptable carrier, diluent or excipient.

35. A method of inhibiting the growth of a microbe or the replication of a virus comprising the step of contacting said virus or microbe with an amount of an antimicrobial peptide according to claim 1 effective to inhibit said growth or said replication.

36. A method for the in vitro inactivation of an endotoxin of a Gram-negative bacteria comprising the step of contacting said endotoxin with an amount of an antimicrobial peptide according to claim 1 effective to inactivate said endotoxin.

37. A method to treat or prevent a microbial or viral infection in a subject comprising the step of administering to a subject in need of such treatment a therapeutically effective amount of an antimicrobial peptide according to claim 1.

38. The method of claim 37 wherein the microbial infection is caused by *Staphylococcus aureus*.

39. The method of claim 38, wherein the antimicrobial peptide is selected from the group consisting of:

| | |
|---|---|
| RGWRLCYCRPRFCVCVGR | (SEQ ID NO: 139); |
| GWRLCYCRPRFCVCVGR | (SEQ ID NO: 141); |
| XCYCRRRFCVCV (X = Cha) | (SEQ ID NO: 164); and |
| WLCYCRRRFCVCV | (SEQ ID NO: 180). |

40. The method of claim 37, wherein the microbial infection is caused by Pseudomonas.

41. The method of claim 37, wherein the microbial infection is caused by *H. pylori*.

42. The method of claim 41, wherein the antimicrobial peptide is selected from the group consisting of:

| | | |
|---|---|---|
| WLCYCRRRFCVCV | | (SEQ ID NO:180); |
| RXCFCRPRFCVCV | (X = Cha) | (SEQ ID NO:178); |
| RGWGLCYCRPRFCVCVGR | | (SEQ ID NO:134); |
| RLCYCRPRFCVCVGR | | (SEQ ID NO:138); |
| RGWRLCYCRGRFCVCVGR | | (SEQ ID NO:136); |
| RGLRXCYCRGRFCVCVGR | (X = Cha) | (SEQ ID NO:149); |
| GWRLCYCRPRFCVCVGR | | (SEQ ID NO:139); |
| RLCYCRRRFCVCV | | (SEQ ID NO:66); |
| WLCYCXXXFCVCV | (X = Dab) | (SEQ ID NO:29); |
| OWRLCYCRPKFCVCV | | (SEQ ID NO:33); |
| RWOLCYCRPKFCVCV | | (SEQ ID NO:37); |
| RRCYCRRRFCVCVGR | | (SEQ ID NO:82); |
| XCYCRRRFCVCV | (X = Cha) | (SEQ ID NO:164); |
| RRRLCYCRRRFCVCVGR | | (SEQ ID NO:242); and |
| RRRLCYCRRRFCVCVGR (all D) | | (SEQ ID NO:243). |

* * * * *

UNITED STATES PATENT AND TRADEMARK OFFICE
CERTIFICATE OF CORRECTION

PATENT NO.    : 5,994,306
DATED         : November 30, 1999
INVENTOR(S)   : Chang et al.

It is certified that error appears in the above-identified patent and that said Letters Patent is hereby corrected as shown below:

Title page,
Item [63], Related U.S. Application Data, should read:
-- Continuation-in-part of application No. 08/690,921, Aug. 1, 1996, abandoned, which is a continuation-in-part of application No.08/649,811, May 17, 1996, abandoned, which is a continuation-in-part of application No. 08/562,346, Nov. 22, 1995, abandoned. --

Column 1,
Lines 1-5 should read:
-- Continuation-in-part of application No. 08/690,921, Aug. 1, 1996, abandoned, which is a continuation-in-part of application No.08/649,811, May 17, 1996, abandoned, which is a continuation-in-part of application No. 08/562,346, Nov. 22, 1995, abandoned. --
Line 26, "U.S. Ser. Nos. 08/960,921" should read -- U.S. Ser. Nos. 08/690,921 --.

Figure 4B:
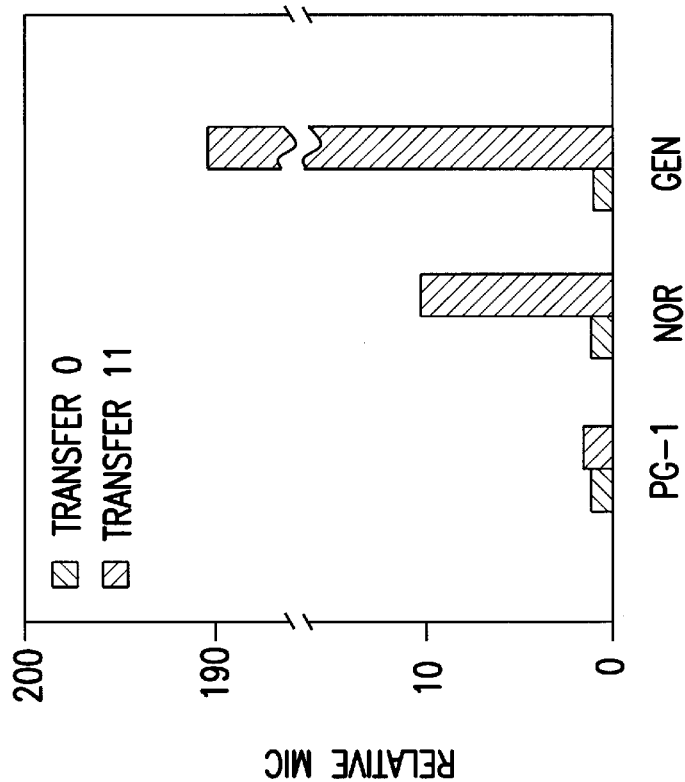
FIG. 4 is a graphical representation of the effect of serial transfer into antibiotic-containing media on the development of drug resistance in methicillin resistant *Staphylococcus aureus* (MRSA) and *Pseudomonas aeruginosa*.
Figure 4A:
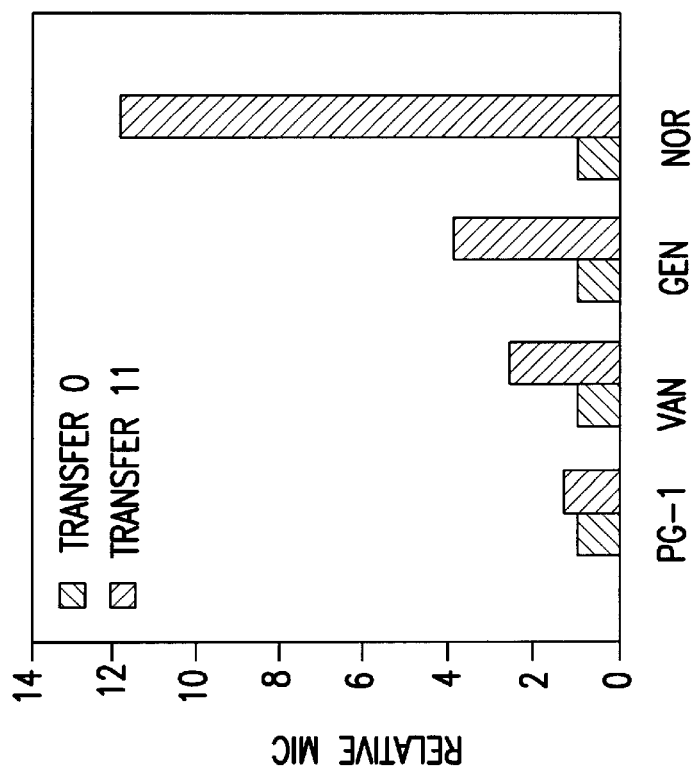

Column 4,
Line 21, "FIG. 1" should read -- FIGS. 1A and 1B --.
Line 26, "FIGS. 3a-3c" should read -- FIGS. 3A-3F --.
Line 29, "FIG. 4" should read -- FIGS. 4A and 4B --.

Column 19,
Line 13, "(SEQ ID NO: 100)" should read -- (SEQ ID NO: 110) --.

Column 28,
Line 11, "(SEQ ID NO:138)" should read -- (SEQ ID NO:188) --.
Line 17, "(SEQ ID NO:139)" should read -- (SEQ ID NO:141) --.

Column 33,
Line 38, "FIG. 1" should read -- FIGS. 1A and 1B --

Column 34,
Line 67, "FIGS. 3a-3c" should read -- FIGS. 3A-3F --

Column 188,
(SEQ ID NO:11), delete "RGVCVCFRRRCYCLW;"

UNITED STATES PATENT AND TRADEMARK OFFICE
CERTIFICATE OF CORRECTION

PATENT NO.   : 5,994,306
DATED        : November 30, 1999
INVENTOR(S)  : Chang et al.

It is certified that error appears in the above-identified patent and that said Letters Patent is hereby corrected as shown below:

<u>COLUMN 189,</u>
The sequence identifier of compound PC 90 (SEQ ID NO:100), should read
-- (SEQ ID NO:110) --
(SEQ ID: 149), under "RGLRXCYCRGRFCVCVGR (X = Cha)"
        delete "(Z = Cha)"
        delete "(Z = Cha)"
(SEQ ID NO:152), delete "RGLRXCYCRGRFCVCVGR (X=Cha)"

<u>Column 194,</u>
Line 20, "(SEQ ID NO:138)" should read -- (SEQ ID NO:188) --
Line 25, "(SEQ ID NO:139)" should read -- (SEQ ID NO:141) --
Line 38, "(SEQ ID NO:243)" should read -- all D-(SEQ ID NO:242). --

Signed and Sealed this

Twentieth Day of August, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 242

(2) INFORMATION FOR SEQ ID NO:1:

(i) SEQUENCE CHARACTERISTICS:
      (A) LENGTH: 18 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:1:

Arg Gly Gly Arg Leu Cys Tyr Cys Arg Arg Arg Phe Cys Val Cys Val
1               5                   10                  15

Gly Arg (2) INFORMATION FOR SEQ ID NO:2:

(i) SEQUENCE CHARACTERISTICS:
      (A) LENGTH: 13 amino acids
      (B) TYPE: amino acid
      (C) STRANDEDNESS: unknown (D) TOPOLOGY: unknown (ii) MOLECULE TYPE: peptide (xi) SEQUENCE DESCRIPTION: SEQ ID NO:2:

Trp Leu Cys Phe Cys Arg Arg Arg Phe Cys Val Cys Val
1               5                   10

(2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:3:

Phe Leu Cys Phe Cys Arg Arg Arg Phe Cys Val Cys Val
1               5                   10

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:4:

Trp Tyr Cys Tyr Cys Arg Arg Arg Phe Cys Val Cys Val
1               5                   10

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 2...3
        (D) OTHER INFORMATION: Xaa=cyclohexylalanine (xi) SEQUENCE DESCRIPTION: SEQ ID NO:5:

Trp Xaa Cys Tyr Cys Arg Arg Arg Phe Cys Val Cys Val
1               5                   10

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:6:

Trp Leu Cys Tyr Cys Arg Arg Arg Phe Cys Val Cys Val Gly Arg
1               5                   10                  15

(2) INFORMATION FOR SEQ ID NO:7:

```
    (i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 2...3
        (D) OTHER INFORMATION: Xaa=cyclohexylalanine (xi) SEQUENCE DESCRIPTION: SEQ ID NO:7:

Trp Xaa Cys Tyr Cys Arg Arg Arg Phe Cys Val Cys Val Gly Arg
 1               5                  10                  15

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

Arg Leu Leu Arg Leu Cys Tyr Cys Arg Arg Arg Phe Cys Val Cys Val
 1               5                  10                  15

Gly Arg (2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 14...15
        (D) OTHER INFORMATION: Xaa=N-methyl valine (xi) SEQUENCE DESCRIPTION: SEQ ID NO:9:

Arg Gly Gly Arg Leu Cys Tyr Cys Arg Arg Arg Phe Cys Xaa Cys Val
 1               5                  10                  15

Gly Arg (2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:10:

Arg Gly Val Cys Val Cys Phe Arg Arg Arg Cys Tyr Cys Leu Trp
 1               5                  10                  15

(2) INFORMATION FOR SEQ ID NO:11:

(i) SEQUENCE CHARACTERISTICS:
```

```
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:11:

Arg Gly Val Cys Val Cys Phe Arg Arg Arg Cys Tyr Cys Leu Trp
1               5                   10                  15

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:12:

Val Cys Val Cys Phe Arg Arg Arg Cys Tyr Cys Leu Trp
1               5                   10

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:13:

Phe Cys Val Cys Phe Arg Arg Arg Cys Phe Cys Leu Phe
1               5                   10

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:14:

Arg Gly Val Cys Val Cys Phe Arg Arg Arg Cys Tyr Cys Arg Gly Gly
1               5                   10                  15
Arg (2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1...18
        (D) OTHER INFORMATION: all amino acids are D amino acids (xi) SEQUENCE DESCRIPTION: SEQ ID NO:15:
```

```
Arg Gly Val Cys Val Cys Phe Arg Arg Arg Cys Tyr Cys Leu Arg Gly
1               5                   10                  15

Gly Arg
```

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:16:

```
Arg Gly Val Cys Val Cys Phe Arg Arg Arg Cys Tyr Cys Leu Trp
1               5                   10                  15
```

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 9...10
        (D) OTHER INFORMATION: Xaa=N-methylglycine (xi) SEQUENCE DESCRIPTION: SEQ ID NO:17:

```
Arg Gly Val Cys Val Cys Tyr Arg Xaa Arg Cys Tyr Cys Leu Trp
1               5                   10                  15
```

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 7
        (D) OTHER INFORMATION: Xaa=N-methylglycine
        (A) NAME/KEY: Other
        (B) LOCATION: 8
        (D) OTHER INFORMATION: Xaa=D-arginine (xi) SEQUENCE DESCRIPTION: SEQ ID NO:18:

```
Trp Leu Cys Tyr Cys Arg Xaa Xaa Tyr Cys Val Cys Val Gly Arg
1               5                   10                  15
```

(2) INFORMATION FOR SEQ ID NO:19:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:19:

```
Arg Gly Phe Cys Val Cys Phe Arg Arg Val Cys Tyr Cys Leu Trp
```

```
           1               5                  10                15

(2) INFORMATION FOR SEQ ID NO:20:

(i) SEQUENCE CHARACTERISTICS:
         (A) LENGTH: 15 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:20:

Trp Leu Cys Tyr Cys Arg Arg Arg Phe Cys Val Cys Val Gly Arg
 1               5                  10                 15

(2) INFORMATION FOR SEQ ID NO:21:

(i) SEQUENCE CHARACTERISTICS:
         (A) LENGTH: 14 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Other
         (B) LOCATION: 8...9
         (D) OTHER INFORMATION: Xaa=D-arginine (xi) SEQUENCE DESCRIPTION: SEQ ID NO:21:

Trp Leu Cys Tyr Cys Arg Arg Xaa Phe Cys Val Cys Val Arg
 1               5                  10

(2) INFORMATION FOR SEQ ID NO:22:

(i) SEQUENCE CHARACTERISTICS:
         (A) LENGTH: 15 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:22:

Trp Leu Cys Tyr Cys Lys Lys Lys Phe Cys Val Cys Val Gly Lys
 1               5                  10                 15

(2) INFORMATION FOR SEQ ID NO:23:

(i) SEQUENCE CHARACTERISTICS:
         (A) LENGTH: 15 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Other
         (B) LOCATION:
         (D) OTHER INFORMATION: N-octyl modified (xi) SEQUENCE DESCRIPTION: SEQ ID NO:23:

Xaa Leu Cys Tyr Cys Arg Arg Arg Phe Cys Val Cys Val Gly Arg
 1               5                  10                 15

(2) INFORMATION FOR SEQ ID NO:24:

(i) SEQUENCE CHARACTERISTICS:
```

(A) LENGTH: 13 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 1...2
            (D) OTHER INFORMATION: Xaa=1-naphthylalanine (xi) SEQUENCE DESCRIPTION: SEQ ID NO:24:

Xaa Leu Cys Tyr Cys Arg Arg Arg Phe Cys Val Cys Val
1               5                   10

(2) INFORMATION FOR SEQ ID NO:25:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:25:

Trp Leu Cys Arg Gly Arg Phe Cys Val Arg
1               5                   10

(2) INFORMATION FOR SEQ ID NO:26:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:26:

Trp Leu Cys Arg Gly Arg Phe Cys Phe Arg
1               5                   10

(2) INFORMATION FOR SEQ ID NO:27:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:27:

Trp Leu Cys Tyr Arg Arg Val Cys Val Arg
1               5                   10

(2) INFORMATION FOR SEQ ID NO:28:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 6...8
            (D) OTHER INFORMATION: Xaa=Ornithine (xi) SEQUENCE DESCRIPTION: SEQ ID NO:28:

Trp Leu Cys Tyr Cys Xaa Xaa Xaa Phe Cys Val Cys Val
1               5                   10

(2) INFORMATION FOR SEQ ID NO:29:

(i) SEQUENCE CHARACTERISTICS:
       (A) LENGTH: 13 amino acids
       (B) TYPE: amino acid
       (C) STRANDEDNESS: unknown
       (D) TOPOLOGY: unknown (ii) MOLECULE TYPE: peptide (ix) FEATURE:
       (A) NAME/KEY: Other
       (B) LOCATION: 6...7
       (D) OTHER INFORMATION: Xaa=2,3-diaminobutyric
           acid
       (A) NAME/KEY: Other
       (B) LOCATION: 7...8
       (D) OTHER INFORMATION: Xaa=2,3-diaminobutyric
           acid
       (A) NAME/KEY: Other
       (B) LOCATION: 8...9
       (D) OTHER INFORMATION: Xaa=2,3-diaminobutyric
           acid (xi) SEQUENCE DESCRIPTION: SEQ ID NO:29:

Trp Leu Cys Tyr Cys Xaa Xaa Xaa Phe Cys Val Cys Val
1               5                   10

(2) INFORMATION FOR SEQ ID NO:30:

(i) SEQUENCE CHARACTERISTICS:
       (A) LENGTH: 13 amino acids
       (B) TYPE: amino acid
       (C) STRANDEDNESS: unknown
       (D) TOPOLOGY: unknown (ii) MOLECULE TYPE: peptide (ix) FEATURE:
       (A) NAME/KEY: Other
       (B) LOCATION: 1...13
       (D) OTHER INFORMATION: all amino acids are D amino acids (xi) SEQUENCE DESCRIPTION: SEQ ID NO:30:

Trp Leu Cys Tyr Cys Arg Arg Arg Phe Cys Val Cys Val
1               5                   10

(2) INFORMATION FOR SEQ ID NO:31:

(i) SEQUENCE CHARACTERISTICS:
       (A) LENGTH: 15 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:31:

His Trp Arg Leu Cys Tyr Cys Arg Pro Lys Phe Cys Val Cys Val
1               5                   10                  15

(2) INFORMATION FOR SEQ ID NO:32:

(i) SEQUENCE CHARACTERISTICS:
       (A) LENGTH: 15 amino acids
       (B) TYPE: amino acid
       (C) STRANDEDNESS: unknown (D) TOPOLOGY: unknown (ii) MOLECULE TYPE: peptide (xi) SEQUENCE DESCRIPTION: SEQ ID NO:32:

Lys Trp Arg Leu Cys Tyr Cys Arg Pro Lys Phe Cys Val Cys Val
1               5                   10                  15

(2) INFORMATION FOR SEQ ID NO:33:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1
        (D) OTHER INFORMATION: Xaa=Ornithine (xi) SEQUENCE DESCRIPTION: SEQ ID NO:33:

Xaa Trp Arg Leu Cys Tyr Cys Arg Pro Lys Phe Cys Val Cys Val
1               5                   10                  15

(2) INFORMATION FOR SEQ ID NO:34:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1...2
        (D) OTHER INFORMATION: Xaa=2,3-diaminobutyric
            acid (xi) SEQUENCE DESCRIPTION: SEQ ID NO:34:

Xaa Trp Arg Leu Cys Tyr Cys Arg Pro Lys Phe Cys Val Cys Val
1               5                   10                  15

(2) INFORMATION FOR SEQ ID NO:35:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:35:

Arg Trp His Leu Cys Tyr Cys Arg Pro Lys Phe Cys Val Cys Val
1               5                   10                  15

(2) INFORMATION FOR SEQ ID NO:36:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:36:

```
Arg Trp Lys Leu Cys Tyr Cys Arg Pro Lys Phe Cys Val Cys Val
1               5                   10                  15
```

(2) INFORMATION FOR SEQ ID NO:37:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 3
        (D) OTHER INFORMATION: Xaa=Ornithine (xi) SEQUENCE DESCRIPTION: SEQ ID NO:37:

```
Arg Trp Xaa Leu Cys Tyr Cys Arg Pro Lys Phe Cys Val Cys Val
1               5                   10                  15
```

(2) INFORMATION FOR SEQ ID NO:38:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 3...4
        (D) OTHER INFORMATION: Xaa=2,3-diaminobutyric
            acid (xi) SEQUENCE DESCRIPTION: SEQ ID NO:38:

```
Arg Trp Xaa Leu Cys Tyr Cys Arg Pro Lys Phe Cys Val Cys Val
1               5                   10                  15
```

(2) INFORMATION FOR SEQ ID NO:39:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 7...8
        (D) OTHER INFORMATION:
            Xaa=1,2,3,4-tetrahydroisoquinoline-3-carboxylic
            acid (xi) SEQUENCE DESCRIPTION: SEQ ID NO:39:

```
Trp Leu Cys Tyr Cys Lys Xaa Lys Phe Cys Val Cys Val Gly Arg
1               5                   10                  15
```

(2) INFORMATION FOR SEQ ID NO:40:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide

```
        (ix) FEATURE:
              (A) NAME/KEY: Other
              (B) LOCATION: 6
              (D) OTHER INFORMATION: Xaa=Hydroxyproline (xi) SEQUENCE DESCRIPTION: SEQ ID NO:40:

Phe Cys Tyr Cys Lys Xaa Lys Phe Cys Tyr Cys Val
1               5                   10

(2) INFORMATION FOR SEQ ID NO:41:

(i) SEQUENCE CHARACTERISTICS:
              (A) LENGTH: 13 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION: 3...4
              (D) OTHER INFORMATION: Xaa=Homocysteine
              (A) NAME/KEY: Other
              (B) LOCATION: 5...6
              (D) OTHER INFORMATION: Xaa=Homocysteine
              (A) NAME/KEY: Other
              (B) LOCATION: 10...11
              (D) OTHER INFORMATION: Xaa=Homocysteine
              (A) NAME/KEY: Other
              (B) LOCATION: 12...13
              (D) OTHER INFORMATION: Xaa=Homocysteine (xi) SEQUENCE DESCRIPTION: SEQ ID NO:41:

Trp Leu Xaa Tyr Xaa Arg Arg Arg Phe Xaa Val Xaa Val
1               5                   10

(2) INFORMATION FOR SEQ ID NO:42:

(i) SEQUENCE CHARACTERISTICS:
              (A) LENGTH: 15 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION: 2
              (D) OTHER INFORMATION:Xaa=ornithine
              (A) NAME/KEY: Other
              (B) LOCATION: 7
              (D) OTHER INFORMATION:Xaa=ornithine
              (A) NAME/KEY: Other
              (B) LOCATION: 8
              (D) OTHER INFORMATION:
                   Xaa=1,2,3,4-tetrahydroisoquinoline-3-carboxylic
                   acid
              (A) NAME/KEY: Other
              (B) LOCATION: 9
              (D) OTHER INFORMATION:Xaa=ornithine
              (A) NAME/KEY: Other
              (B) LOCATION: 15
              (D) OTHER INFORMATION:Xaa=ornithine (xi) SEQUENCE DESCRIPTION: SEQ ID NO:42:

Trp Xaa Leu Cys Tyr Cys Xaa Xaa Xaa Phe Cys Val Cys Val Xaa
1               5                   10                  15

(2) INFORMATION FOR SEQ ID NO:43:

(i) SEQUENCE CHARACTERISTICS:
```

(A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1
        (D) OTHER INFORMATION:Xaa=ornithine
        (A) NAME/KEY: Other
        (B) LOCATION: 7
        (D) OTHER INFORMATION:Xaa=ornithine
        (A) NAME/KEY: Other
        (B) LOCATION: 8
        (D) OTHER INFORMATION:
            Xaa=1,2,3,4-tetrahydroisoquinoline-3-carboxylic
            acid
        (A) NAME/KEY: Other
        (B) LOCATION: 9
        (D) OTHER INFORMATION:Xaa=ornithine
        (A) NAME/KEY: Other
        (B) LOCATION: 15
        (D) OTHER INFORMATION:Xaa=ornithine (xi) SEQUENCE DESCRIPTION: SEQ ID NO:43:

Xaa Phe Cys Val Cys Val Xaa Xaa Xaa Phe Cys Val Cys Val Xaa
1               5                   10                  15

(2) INFORMATION FOR SEQ ID NO:44:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1
        (D) OTHER INFORMATION:Xaa=ornithine
        (A) NAME/KEY: Other
        (B) LOCATION: 3
        (D) OTHER INFORMATION:Xaa=ornithine
        (A) NAME/KEY: Other
        (B) LOCATION: 8
        (D) OTHER INFORMATION:Xaa=ornithine
        (A) NAME/KEY: Other
        (B) LOCATION: 9
        (D) OTHER INFORMATION:
            Xaa=1,2,3,4-tetrahydroisoquinoline-3-carboxylic acid
        (A) NAME/KEY: Other
        (B) LOCATION: 10
        (D) OTHER INFORMATION:Xaa=ornithine (xi) SEQUENCE DESCRIPTION: SEQ ID NO:44:

Xaa Trp Xaa Leu Cys Tyr Cys Xaa Xaa Xaa Phe Cys Val Cys Val
1               5                   10                  15

(2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1
        (D) OTHER INFORMATION:Xaa=ornithine (A) NAME/KEY: Other
            (B) LOCATION: 6
            (D) OTHER INFORMATION:
                Xaa=1,2,3,4-tetrahydroisoquinoline-3-carboxylic acid
            (A) NAME/KEY: Other
            (B) LOCATION: 7
            (D) OTHER INFORMATION:Xaa=ornithine
            (A) NAME/KEY: Other
            (B) LOCATION: 13
            (D) OTHER INFORMATION:Xaa=ornithine (xi) SEQUENCE DESCRIPTION: SEQ ID NO:45:

Xaa Phe Cys Val Cys Xaa Xaa Leu Cys Tyr Cys Phe Xaa
1               5                   10

(2) INFORMATION FOR SEQ ID NO:46:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:46:

Trp Leu Cys Tyr Cys Lys Lys Lys Phe Cys Val Cys Val
1               5                   10

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1
        (D) OTHER INFORMATION:Xaa=ornithine
        (A) NAME/KEY: Other
        (B) LOCATION: 3
        (D) OTHER INFORMATION:Xaa=ornithine
        (A) NAME/KEY: Other
        (B) LOCATION: 5
        (D) OTHER INFORMATION:Xaa=ornithine
        (A) NAME/KEY: Other
        (B) LOCATION: 9
        (D) OTHER INFORMATION:Xaa=ornithine
        (A) NAME/KEY: Other
        (B) LOCATION: 10
        (D) OTHER INFORMATION: Xaa=Hydroxyproline
        (A) NAME/KEY: Other
        (B) LOCATION: 11
        (D) OTHER INFORMATION:Xaa=ornithine (xi) SEQUENCE DESCRIPTION: SEQ ID NO:47:

Xaa Trp Xaa Leu Xaa Cys Tyr Cys Xaa Xaa Xaa Phe Cys Val Cys Val
1               5                   10                  15

(2) INFORMATION FOR SEQ ID NO:48:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (ix) FEATURE:

(A) NAME/KEY: Other
            (B) LOCATION: 6
            (D) OTHER INFORMATION:Xaa=ornithine
            (A) NAME/KEY: Other
            (B) LOCATION: 7
            (D) OTHER INFORMATION: Xaa=Parabenzylphenylalanine
            (A) NAME/KEY: Other
            (B) LOCATION: 8
            (D) OTHER INFORMATION:Xaa=ornithine
            (A) NAME/KEY: Other
            (B) LOCATION: 14
            (D) OTHER INFORMATION:Xaa=ornithine (xi) SEQUENCE DESCRIPTION: SEQ ID NO:48:

Trp Leu Cys Tyr Cys Xaa Xaa Xaa Phe Cys Val Cys Val Xaa
1               5                   10

(2) INFORMATION FOR SEQ ID NO:49:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 1...10
            (D) OTHER INFORMATION: All amino acids are D amino acids
            (A) NAME/KEY: Other
            (B) LOCATION: 6...8
            (D) OTHER INFORMATION:Xaa=ornithine (xi) SEQUENCE DESCRIPTION: SEQ ID NO:49:

Trp Leu Cys Tyr Cys Xaa Xaa Xaa Phe Cys Val Cys Val
1               5                   10

(2) INFORMATION FOR SEQ ID NO:50:

(i) SEQUENCE CHARACTERISTICS:
            (A) LENGTH: 14 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 1...2
            (D) OTHER INFORMATION: Xaa=D-arginine
            (A) NAME/KEY: Other
            (B) LOCATION: 8...9
            (D) OTHER INFORMATION: Xaa=D-arginine (xi) SEQUENCE DESCRIPTION: SEQ ID NO:50:

Xaa Phe Cys Tyr Cys Leu Arg Xaa Phe Cys Val Cys Val Arg
1               5                   10

(2) INFORMATION FOR SEQ ID NO:51:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 8...9

(D) OTHER INFORMATION: Xaa=D-arginine
            (A) NAME/KEY: Other
            (B) LOCATION: 13...14
            (D) OTHER INFORMATION: Xaa=N-methylglycine
            (A) NAME/KEY: Other
            (B) LOCATION: 14...15
            (D) OTHER INFORMATION: Xaa=D-arginine (xi) SEQUENCE DESCRIPTION: SEQ ID NO:51:

Trp Leu Cys Tyr Cys Arg Arg Xaa Phe Cys Val Cys Val Xaa Xaa
1               5                   10                  15

(2) INFORMATION FOR SEQ ID NO:52:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:52:

Leu Cys Tyr Cys Arg Arg Arg Phe Cys Val Cys Val Gly Arg
1               5                   10

(2) INFORMATION FOR SEQ ID NO:53:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:53:

Arg Cys Tyr Cys Arg Arg Arg Phe Cys Val Cys Val
1               5                   10

(2) INFORMATION FOR SEQ ID NO:54:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:54:

Arg Gly Gly Arg Leu Cys Tyr Cys Arg Arg Arg Phe Cys Val Cys Arg
1               5                   10                  15

(2) INFORMATION FOR SEQ ID NO:55:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:55:

Arg Cys Tyr Cys Arg Arg Arg Phe Cys Val Cys Arg
1               5                   10

(2) INFORMATION FOR SEQ ID NO:56:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:56:

Leu Cys Tyr Cys Arg Arg Arg Phe Cys Val Cys Val
 1               5                  10

(2) INFORMATION FOR SEQ ID NO:57:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:57:

Leu Cys Tyr Ala Arg Arg Arg Phe Ala Val Cys Val
 1               5                  10

(2) INFORMATION FOR SEQ ID NO:58:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:58:

Arg Cys Tyr Ala Arg Arg Arg Phe Ala Val Cys Arg
 1               5                  10

(2) INFORMATION FOR SEQ ID NO:59:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:59:

Leu Ala Tyr Cys Arg Arg Arg Phe Cys Val Ala Val
 1               5                  10

(2) INFORMATION FOR SEQ ID NO:60:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:60:

Arg Ala Tyr Cys Arg Arg Arg Phe Cys Val Ala Arg
 1               5                  10

(2) INFORMATION FOR SEQ ID NO:61:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:61:

Arg Gly Gly Arg Leu Cys Tyr Arg Arg Val Cys Val
1               5                   10

(2) INFORMATION FOR SEQ ID NO:62:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:62:

Gly Gly Arg Leu Cys Tyr Cys Arg Arg Arg Phe Cys Val Cys Val
1               5                   10                  15

(2) INFORMATION FOR SEQ ID NO:63:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:63:

Arg Gly Arg Leu Cys Tyr Cys Arg Arg Arg Phe Cys Val Cys Val
1               5                   10                  15

(2) INFORMATION FOR SEQ ID NO:64:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:64:

Gly Arg Leu Cys Tyr Cys Arg Arg Arg Phe Cys Val Cys Val
1               5                   10

(2) INFORMATION FOR SEQ ID NO:65:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:65:

Arg Arg Leu Cys Tyr Cys Arg Arg Arg Phe Cys Val Cys Val
1               5                   10

(2) INFORMATION FOR SEQ ID NO:66:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:66:

Arg Leu Cys Tyr Cys Arg Arg Arg Phe Cys Val Cys Val
 1               5                  10

(2) INFORMATION FOR SEQ ID NO:67:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:67:

Arg Arg Cys Tyr Cys Arg Arg Arg Phe Cys Val Cys Val
 1               5                  10

(2) INFORMATION FOR SEQ ID NO:68:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:68:

Cys Tyr Cys Arg Arg Arg Phe Cys Val Cys Val
 1               5                  10

(2) INFORMATION FOR SEQ ID NO:69:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:69:

Arg Gly Gly Arg Leu Cys Tyr Cys Arg Arg Arg Phe Cys Val Cys
 1               5                  10                  15

(2) INFORMATION FOR SEQ ID NO:70:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:70:

Arg Gly Gly Arg Leu Cys Tyr Arg Arg Arg Phe Val Cys Val
 1               5                  10

(2) INFORMATION FOR SEQ ID NO:71:

(i) SEQUENCE CHARACTERISTICS:
    (A) LENGTH: 16 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:71:

Arg Gly Trp Arg Leu Cys Tyr Cys Arg Arg Arg Phe Cys Val Cys Val
1               5                   10                  15

(2) INFORMATION FOR SEQ ID NO:72:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:72:

Cys Tyr Cys Arg Arg Arg Phe Cys Val Cys Val Gly Arg
1               5                   10

(2) INFORMATION FOR SEQ ID NO:73:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:73:

Arg Gly Gly Arg Leu Cys Tyr Cys Arg Arg Arg Phe Cys Val
1               5                   10

(2) INFORMATION FOR SEQ ID NO:74:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:74:

Leu Cys Tyr Cys Arg Arg Arg Phe Cys Val Cys
1               5                   10

(2) INFORMATION FOR SEQ ID NO:75:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:75:

Leu Cys Tyr Thr Arg Arg Arg Phe Thr Val Cys Val
1               5                   10

(2) INFORMATION FOR SEQ ID NO:76:

(i) SEQUENCE CHARACTERISTICS:
    (A) LENGTH: 12 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:76:

Leu Thr Tyr Cys Arg Arg Arg Phe Cys Val Thr Val
1               5                   10

(2) INFORMATION FOR SEQ ID NO:77:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:77:

Gly Gly Arg Leu Cys Tyr Cys Arg Arg Arg Phe Cys Val Cys Val Gly
1               5                   10                  15

Arg (2) INFORMATION FOR SEQ ID NO:78:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:78:

Arg Gly Arg Leu Cys Tyr Cys Arg Arg Arg Phe Cys Val Cys Val Gly
1               5                   10                  15

Arg (2) INFORMATION FOR SEQ ID NO:79:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:79:

Gly Arg Leu Cys Tyr Cys Arg Arg Arg Phe Cys Val Cys Val Gly Arg
1               5                   10                  15

(2) INFORMATION FOR SEQ ID NO:80:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:80:

Arg Arg Leu Cys Tyr Cys Arg Arg Arg Phe Cys Val Cys Val Gly Arg
1               5                   10                  15

(2) INFORMATION FOR SEQ ID NO:81:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:81:

Arg Leu Cys Tyr Cys Arg Arg Arg Phe Cys Val Cys Val Gly Arg
1               5                   10                  15

(2) INFORMATION FOR SEQ ID NO:82:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:82:

Arg Arg Cys Tyr Cys Arg Arg Arg Phe Cys Val Cys Val Gly Arg
1               5                   10                  15

(2) INFORMATION FOR SEQ ID NO:83:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:83:

Arg Gly Gly Arg Leu Cys Tyr Cys Arg Arg Arg Phe Cys Val Cys Arg
1               5                   10                  15

(2) INFORMATION FOR SEQ ID NO:84:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:84:

Arg Gly Gly Arg Leu Cys Tyr Arg Arg Arg Phe Val Cys Val Gly Arg
1               5                   10                  15

(2) INFORMATION FOR SEQ ID NO:85:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:85:

Arg Gly Trp Arg Leu Cys Tyr Cys Arg Arg Arg Phe Cys Val Cys Val
1               5                   10                  15

Gly Arg (2) INFORMATION FOR SEQ ID NO:86:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:86:

Arg Gly Trp Arg Leu Ala Tyr Cys Arg Arg Phe Cys Val Ala Val
1               5                   10                  15
Gly Arg (2) INFORMATION FOR SEQ ID NO:87:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:87:

Arg Cys Tyr Cys Arg Arg Arg Phe Cys Val Cys Val
1               5                   10

(2) INFORMATION FOR SEQ ID NO:88:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:88:

Leu Cys Tyr Cys Arg Arg Arg Phe Cys Val Cys Arg
1               5                   10

(2) INFORMATION FOR SEQ ID NO:89:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:89:

Val Cys Tyr Cys Phe Arg Arg Phe Cys Tyr Cys Val
1               5                   10

(2) INFORMATION FOR SEQ ID NO:90:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:90:

Leu Cys Tyr Thr Arg Pro Arg Phe Thr Val Cys Val
1               5                   10

(2) INFORMATION FOR SEQ ID NO:91:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:91:

Leu Cys Tyr Thr Arg Gly Arg Phe Thr Val Cys Val
1               5                   10

(2) INFORMATION FOR SEQ ID NO:92:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:92:

Leu Cys Tyr Phe Arg Arg Arg Phe Ile Val Cys Val
1               5                   10

(2) INFORMATION FOR SEQ ID NO:93:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:93:

Leu Cys Tyr Phe Arg Pro Arg Phe Ile Val Cys Val
1               5                   10

(2) INFORMATION FOR SEQ ID NO:94:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:94:

Leu Cys Tyr Thr Phe Arg Pro Arg Phe Val Cys Val
1               5                   10

(2) INFORMATION FOR SEQ ID NO:95:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:95:

Leu Cys Tyr Thr Phe Arg Gly Arg Phe Val Cys Val
1               5                   10

(2) INFORMATION FOR SEQ ID NO:96:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:96:

Cys Tyr Cys Phe Arg Arg Phe Cys Val Cys
1               5                   10

(2) INFORMATION FOR SEQ ID NO:97:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:97:

Leu Cys Tyr Cys Arg Arg Arg Arg Cys Val Cys Val
1               5                   10

(2) INFORMATION FOR SEQ ID NO:98:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:98:

Leu Cys Tyr Cys Phe Arg Arg Arg Cys Val Cys Val
1               5                   10

(2) INFORMATION FOR SEQ ID NO:99:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:99:

Leu Cys Tyr Cys Arg Phe Arg Arg Cys Val Cys Val
1               5                   10

(2) INFORMATION FOR SEQ ID NO:100:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:100:

Leu Cys Tyr Cys Arg Arg Phe Arg Cys Val Cys Val
1               5                   10

(2) INFORMATION FOR SEQ ID NO:101:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:101:

Leu Cys Tyr Cys Arg Arg Phe Phe Cys Val Cys Val
1               5                   10

(2) INFORMATION FOR SEQ ID NO:102:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:102:

Leu Cys Tyr Cys Arg Phe Phe Arg Cys Val Cys Val
1               5                   10

(2) INFORMATION FOR SEQ ID NO:103:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:103:

Leu Cys Tyr Cys Phe Phe Arg Arg Cys Val Cys Val
1               5                   10

(2) INFORMATION FOR SEQ ID NO:104:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:104:

Leu Cys Tyr Cys Phe Arg Arg Phe Cys Val Cys Val
1               5                   10

(2) INFORMATION FOR SEQ ID NO:105:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:105:

Leu Cys Tyr Cys Phe Arg Phe Arg Cys Val Cys Val
1               5                   10

(2) INFORMATION FOR SEQ ID NO:106:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:106:

Leu Cys Tyr Cys Arg Phe Arg Phe Cys Val Cys Val
1               5                   10

(2) INFORMATION FOR SEQ ID NO:107:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:107:

Leu Cys Tyr Cys Phe Arg Phe Phe Cys Val Cys Val
1               5                   10

(2) INFORMATION FOR SEQ ID NO:108:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:108:

Leu Cys Tyr Cys Phe Phe Arg Phe Cys Val Cys Val
1               5                   10

(2) INFORMATION FOR SEQ ID NO:109:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:109:

Leu Cys Tyr Cys Phe Phe Phe Arg Cys Val Cys Val
1               5                   10

(2) INFORMATION FOR SEQ ID NO:110:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:110:

Leu Cys Tyr Cys Arg Phe Phe Phe Cys Val Cys Val
1               5                   10

(2) INFORMATION FOR SEQ ID NO:111:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:111:

Arg Gly Gly Arg Leu Cys Tyr Arg Arg Val Cys Val Gly Arg
1               5                   10

(2) INFORMATION FOR SEQ ID NO:112:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:112:

Tyr Cys Tyr Cys Arg Arg Arg Phe Cys Val Cys Val Gly Arg
1               5                   10

(2) INFORMATION FOR SEQ ID NO:113:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:113:

Ile Cys Tyr Cys Arg Arg Arg Phe Cys Val Cys Val Gly Arg
1               5                   10

(2) INFORMATION FOR SEQ ID NO:114:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:114:

Phe Cys Tyr Cys Arg Arg Arg Phe Cys Val Cys Val Gly Arg
1               5                   10

(2) INFORMATION FOR SEQ ID NO:115:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:115:

Trp Cys Tyr Cys Arg Arg Arg Phe Cys Val Cys Val Gly Arg
 1               5                  10

(2) INFORMATION FOR SEQ ID NO:116:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:116:

Arg Cys Tyr Cys Arg Arg Arg Phe Cys Val Cys Val Gly Arg
 1               5                  10

(2) INFORMATION FOR SEQ ID NO:117:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:117:

Arg Leu Cys Tyr Thr Arg Gly Arg Phe Thr Val Cys Val
 1               5                  10

(2) INFORMATION FOR SEQ ID NO:118:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:118:

Leu Cys Tyr Thr Arg Gly Arg Phe Thr Val Cys Val Arg
 1               5                  10

(2) INFORMATION FOR SEQ ID NO:119:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:119:

Arg Leu Cys Tyr Thr Arg Gly Arg Phe Thr Val Cys Val Arg
 1               5                  10

(2) INFORMATION FOR SEQ ID NO:120:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:120:

Leu Cys Tyr Cys His His His Phe Cys Val Cys Val
1               5                   10

(2) INFORMATION FOR SEQ ID NO:121:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:121:

Leu Cys Tyr Thr His His His Phe Thr Val Cys Val
1               5                   10

(2) INFORMATION FOR SEQ ID NO:122:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:122:

Arg Gly Gly Leu Cys Tyr Cys Arg Arg Arg Phe Cys Val Cys Val Gly
1               5                   10                  15

Arg (2) INFORMATION FOR SEQ ID NO:123:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:123:

Arg Gly Gly Arg Leu Cys Tyr Cys Arg Arg Arg Phe Cys Val Cys Val
1               5                   10                  15

Gly Arg (2) INFORMATION FOR SEQ ID NO:124:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:124:

Arg Gly Gly Gly Leu Cys Tyr Cys Arg Arg Arg Phe Cys Val Cys Val
1               5                   10                  15

Gly Arg (2) INFORMATION FOR SEQ ID NO:125:

(i) SEQUENCE CHARACTERISTICS:
        (A) LENGTH: 18 amino acids (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:125:

Arg Gly Gly Gly Leu Cys Tyr Cys Arg Arg Gly Phe Cys Val Cys Phe
1               5                  10                  15

Gly Arg (2) INFORMATION FOR SEQ ID NO:126:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:126:

Arg Gly Gly Gly Leu Cys Tyr Cys Arg Arg Pro Phe Cys Val Cys Val
1               5                  10                  15

Gly Arg (2) INFORMATION FOR SEQ ID NO:127:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:127:

Arg Gly Gly Gly Leu Cys Tyr Cys Arg Pro Arg Phe Cys Val Cys Val
1               5                  10                  15

Gly Arg (2) INFORMATION FOR SEQ ID NO:128:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 10...11
            (D) OTHER INFORMATION: Xaa=N-methylglycine (xi) SEQUENCE DESCRIPTION: SEQ ID NO:128:

Arg Gly Gly Arg Leu Cys Tyr Cys Arg Xaa Arg Phe Cys Val Cys Val
1               5                  10                  15

Gly Arg (2) INFORMATION FOR SEQ ID NO:129:

(i) SEQUENCE CHARACTERISTICS:
            (A) LENGTH: 17 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:129:

Arg Gly Gly Leu Cys Tyr Cys Arg Gly Arg Phe Cys Val Cys Val Gly
 1               5                  10                  15

Arg (2) INFORMATION FOR SEQ ID NO:130:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 9...10
            (D) OTHER INFORMATION: Xaa=citrulline (xi) SEQUENCE DESCRIPTION: SEQ ID NO:130:

Arg Gly Gly Arg Leu Cys Tyr Cys Xaa Gly Arg Phe Cys Val Cys Val
 1               5                  10                  15

Gly Arg (2) INFORMATION FOR SEQ ID NO:131:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 1...2
            (D) OTHER INFORMATION: Xaa=citrulline (xi) SEQUENCE DESCRIPTION: SEQ ID NO:131:

Xaa Gly Gly Arg Leu Cys Tyr Cys Arg Gly Arg Phe Cys Val Cys Val
 1               5                  10                  15

Gly Arg (2) INFORMATION FOR SEQ ID NO:132:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:132:

Arg Gly Gly Arg Val Cys Tyr Cys Arg Gly Arg Phe Cys Val Cys Val
 1               5                  10                  15

Gly Arg (2) INFORMATION FOR SEQ ID NO:133:

(i) SEQUENCE CHARACTERISTICS:
            (A) LENGTH: 18 amino acids
            (B) TYPE: amino acid

```
            (C) STRANDEDNESS: unknown
            (D) TOPOLOGY: unknown (ii) MOLECULE TYPE: peptide (xi) SEQUENCE DESCRIPTION: SEQ ID NO:133:

Arg Gly Gly Gly Leu Cys Tyr Cys Phe Pro Lys Phe Cys Val Cys Val
 1               5                  10                  15

Gly Arg (2) INFORMATION FOR SEQ ID NO:134:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:134:

Arg Gly Trp Gly Leu Cys Tyr Cys Arg Pro Arg Phe Cys Val Cys Val
 1               5                  10                  15

Gly Arg (2) INFORMATION FOR SEQ ID NO:135:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 10...11
            (D) OTHER INFORMATION: Xaa=N-methylglycine (xi) SEQUENCE DESCRIPTION: SEQ ID NO:135:

Arg Gly Trp Arg Leu Cys Tyr Cys Arg Xaa Arg Phe Cys Val Cys Val
 1               5                  10                  15

Gly Arg (2) INFORMATION FOR SEQ ID NO:136:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:136:

Arg Gly Trp Arg Leu Cys Tyr Cys Arg Gly Arg Phe Cys Val Cys Val
 1               5                  10                  15

Gly Arg (2) INFORMATION FOR SEQ ID NO:137:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown
```

(ii) MOLECULE TYPE: peptide (ix) FEATURE:
            (A) NAME/KEY: Other
            (B) LOCATION: 9...10
            (D) OTHER INFORMATION: Xaa=citrulline (xi) SEQUENCE DESCRIPTION: SEQ ID NO:137:

Arg Gly Trp Arg Leu Cys Tyr Cys Xaa Pro Arg Phe Cys Val Cys Val
 1               5                  10                  15

Gly Arg (2) INFORMATION FOR SEQ ID NO:138:

(i) SEQUENCE CHARACTERISTICS:
            (A) LENGTH: 17 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:138:

Arg Trp Arg Leu Cys Tyr Cys Arg Pro Arg Phe Cys Val Cys Val Gly
 1               5                  10                  15

Arg (2) INFORMATION FOR SEQ ID NO:139:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:139:

Arg Gly Trp Arg Leu Cys Tyr Cys Arg Pro Arg Phe Cys Val Cys Val
 1               5                  10                  15

Gly Arg (2) INFORMATION FOR SEQ ID NO:140:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:140:

Arg Gly Trp Arg Ala Cys Tyr Cys Arg Pro Arg Phe Cys Ala Cys Val
 1               5                  10                  15

Gly Arg (2) INFORMATION FOR SEQ ID NO:141:

(i) SEQUENCE CHARACTERISTICS:
            (A) LENGTH: 17 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:141:

Gly Trp Arg Leu Cys Tyr Cys Arg Pro Arg Phe Cys Val Cys Val Gly
1               5                   10                  15

Arg (2) INFORMATION FOR SEQ ID NO:142:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:142:

Arg Trp Arg Leu Cys Tyr Cys Lys Gly Lys Phe Cys Val Cys Val Gly
1               5                   10                  15

Arg (2) INFORMATION FOR SEQ ID NO:143:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 10...11
        (D) OTHER INFORMATION: Xaa=N-methylglycine (xi) SEQUENCE DESCRIPTION: SEQ ID NO:143:

Arg Gly Trp Arg Leu Cys Tyr Cys Arg Xaa Arg Phe Cys Val Cys Val
1               5                   10                  15

Gly Arg (2) INFORMATION FOR SEQ ID NO:144:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:144:

Gly Gly Trp Arg Leu Cys Tyr Cys Arg Gly Arg Phe Cys Val Cys Val
1               5                   10                  15

Gly Arg (2) INFORMATION FOR SEQ ID NO:145:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:145:

Arg Gly Gly Trp Leu Cys Tyr Cys Arg Gly Arg Phe Cys Val Cys Val
1               5                   10                  15

Gly Arg (2) INFORMATION FOR SEQ ID NO:146:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 10...11
        (D) OTHER INFORMATION: Xaa=N-methylglycine (xi) SEQUENCE DESCRIPTION: SEQ ID NO:146:

Arg Leu Leu Arg Leu Cys Tyr Cys Arg Xaa Arg Phe Cys Val Cys Val
 1               5                  10                  15

Gly Arg (2) INFORMATION FOR SEQ ID NO:147:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 10...11
        (D) OTHER INFORMATION: Xaa=N-methylglycine (xi) SEQUENCE DESCRIPTION: SEQ ID NO:147:

Arg Leu Leu Arg Ala Cys Tyr Cys Arg Xaa Arg Phe Cys Val Cys Val
 1               5                  10                  15

Gly Arg (2) INFORMATION FOR SEQ ID NO:148:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:148:

Arg Leu Leu Arg Leu Cys Tyr Cys Arg Arg Arg Phe Cys Val Cys Val
 1               5                  10                  15

Gly Arg (2) INFORMATION FOR SEQ ID NO:149:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other (B) LOCATION: 5...6
            (D) OTHER INFORMATION: Xaa=cyclohexylalanine (xi) SEQUENCE DESCRIPTION: SEQ ID NO:149:

Arg Gly Leu Arg Xaa Cys Tyr Cys Arg Gly Arg Phe Cys Val Cys Val
1               5                   10                  15

Gly Arg (2) INFORMATION FOR SEQ ID NO:150:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 10...11
            (D) OTHER INFORMATION: Xaa=N-methylglycine
            (A) NAME/KEY: Other
            (B) LOCATION: 12...13
            (D) OTHER INFORMATION: Xaa=cyclohexylalanine (xi) SEQUENCE DESCRIPTION: SEQ ID NO:150:

Arg Gly Gly Arg Leu Cys Tyr Cys Arg Xaa Arg Xaa Cys Val Cys Trp
1               5                   10                  15

Gly Arg (2) INFORMATION FOR SEQ ID NO:151:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 10
            (D) OTHER INFORMATION: Xaa=N-methylglycine
            (A) NAME/KEY: Other
            (B) LOCATION: 12
            (D) OTHER INFORMATION: Xaa=cyclohexylalanine (xi) SEQUENCE DESCRIPTION: SEQ ID NO:151:

Arg Gly Gly Arg Trp Cys Val Cys Arg Xaa Arg Xaa Cys Tyr Cys Val
1               5                   10                  15

Gly Arg (2) INFORMATION FOR SEQ ID NO:152:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 5...6
            (D) OTHER INFORMATION: Xaa=cyclohexylalanine (xi) SEQUENCE DESCRIPTION: SEQ ID NO:152:

```
Arg Gly Leu Arg Xaa Cys Tyr Cys Arg Gly Arg Phe Cys Val Cys Val
 1               5                  10                  15

Gly Arg
```

(2) INFORMATION FOR SEQ ID NO:153:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 12...13
        (D) OTHER INFORMATION: Xaa=Cha=cyclohexylalanine (xi) SEQUENCE DESCRIPTION: SEQ ID NO:153:

```
Arg Gly Gly Arg Trp Cys Val Cys Arg Gly Arg Xaa Cys Tyr Cys Val
 1               5                  10                  15

Gly Arg
```

(2) INFORMATION FOR SEQ ID NO:154:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 14...15
        (D) OTHER INFORMATION: Xaa=N-methylvaline (xi) SEQUENCE DESCRIPTION: SEQ ID NO:154:

```
Arg Gly Gly Arg Leu Cys Tyr Cys Arg Arg Arg Phe Cys Xaa Cys Val
 1               5                  10                  15

Gly Arg
```

(2) INFORMATION FOR SEQ ID NO:155:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:155:

```
Leu Cys Tyr Cys Arg Arg Arg Phe Cys Val Cys Val
 1               5                  10
```

(2) INFORMATION FOR SEQ ID NO:156:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:156:

Leu Cys Tyr Cys Arg Arg Cys Phe Cys Val Cys Val
1               5                   10

(2) INFORMATION FOR SEQ ID NO:157:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:157:

Leu Cys Tyr Cys Arg Arg Arg Phe Cys Val Cys Phe
1               5                   10

(2) INFORMATION FOR SEQ ID NO:158:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:158:

Leu Cys Ala Cys Arg Arg Arg Ala Cys Val Cys Val
1               5                   10

(2) INFORMATION FOR SEQ ID NO:159:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 6...7
        (D) OTHER INFORMATION: Xaa=D-Arginine (xi) SEQUENCE DESCRIPTION: SEQ ID NO:159:

Leu Cys Tyr Cys Arg Xaa Arg Phe Cys Val Cys Val
1               5                   10

(2) INFORMATION FOR SEQ ID NO:160:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:160:

Leu Cys Trp Cys Arg Arg Arg Phe Cys Val Cys Val
1               5                   10

(2) INFORMATION FOR SEQ ID NO:161:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:161:

Trp Cys Tyr Cys Arg Arg Arg Phe Cys Val Cys Val
1               5                   10

(2) INFORMATION FOR SEQ ID NO:162:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 8...9
            (D) OTHER INFORMATION: Xaa=Homophenylalanine (xi) SEQUENCE DESCRIPTION: SEQ ID NO:162:

Leu Cys Tyr Cys Arg Arg Arg Xaa Cys Val Cys Val
1               5                   10

(2) INFORMATION FOR SEQ ID NO:163:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 8...9
            (D) OTHER INFORMATION: Xaa=4-chlorophenylalanine (xi) SEQUENCE DESCRIPTION: SEQ ID NO:163:

Leu Cys Tyr Cys Arg Arg Arg Xaa Cys Val Cys Val
1               5                   10

(2) INFORMATION FOR SEQ ID NO:164:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 1...2
            (D) OTHER INFORMATION: Xaa=cyclohexylalanine (xi) SEQUENCE DESCRIPTION: SEQ ID NO:164:

Xaa Cys Tyr Cys Arg Arg Arg Phe Cys Val Cys Val
1               5                   10

(2) INFORMATION FOR SEQ ID NO:165:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (ix) FEATURE:
              (A) NAME/KEY: Other
              (B) LOCATION: 10...11
              (D) OTHER INFORMATION: Xaa=D-Histidine (xi) SEQUENCE DESCRIPTION: SEQ ID NO:165:

Leu Cys Tyr Cys Arg Arg Arg Phe Cys Xaa Cys Val
1               5                   10

(2) INFORMATION FOR SEQ ID NO:166:

(i) SEQUENCE CHARACTERISTICS:
              (A) LENGTH: 12 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION: 9...10
              (D) OTHER INFORMATION: Xaa=MeGly=N-methylglycine (xi) SEQUENCE DESCRIPTION: SEQ ID NO:166:

Leu Cys Tyr Cys Arg Arg Arg Xaa Cys Val Cys Val
1               5                   10

(2) INFORMATION FOR SEQ ID NO:167:

(i) SEQUENCE CHARACTERISTICS:
              (A) LENGTH: 12 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION: 8...9
              (D) OTHER INFORMATION: Xaa=N-methylphenylalanine (xi) SEQUENCE DESCRIPTION: SEQ ID NO:167:

Leu Cys Tyr Cys Arg Arg Arg Xaa Cys Val Cys Val
1               5                   10

(2) INFORMATION FOR SEQ ID NO:168:

(i) SEQUENCE CHARACTERISTICS:
              (A) LENGTH: 12 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION: 10...11
              (D) OTHER INFORMATION: Xaa=N-methyl valine (xi) SEQUENCE DESCRIPTION: SEQ ID NO:168:

Leu Cys Tyr Cys Arg Arg Arg Phe Cys Xaa Cys Val
1               5                   10

(2) INFORMATION FOR SEQ ID NO:169:

(i) SEQUENCE CHARACTERISTICS:
              (A) LENGTH: 12 amino acids (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 3...4
            (D) OTHER INFORMATION: Xaa=cyclohexylalanine
            (A) NAME/KEY: Other
            (B) LOCATION: 8...9
            (D) OTHER INFORMATION: Xaa=cyclohexylalanine (xi) SEQUENCE DESCRIPTION: SEQ ID NO:169:

Leu Cys Xaa Cys Arg Arg Arg Xaa Cys Val Cys Val
 1               5                  10

(2) INFORMATION FOR SEQ ID NO:170:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:170:

Leu Cys Gly Cys Arg Arg Arg Gly Cys Val Cys Val
 1               5                  10

(2) INFORMATION FOR SEQ ID NO:171:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:171:

Leu Cys Ala Cys Arg Gly Arg Ala Cys Val Cys Val
 1               5                  10

(2) INFORMATION FOR SEQ ID NO:172:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:172:

Arg Ala Cys Tyr Cys Arg Pro Arg Phe Cys Ala Cys Val
 1               5                  10

(2) INFORMATION FOR SEQ ID NO:173:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:173:

Arg Leu Cys Tyr Cys Arg Pro Arg Phe Cys Val Cys Phe
1               5                   10

(2) INFORMATION FOR SEQ ID NO:174:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:174:

Arg Leu Cys Tyr Cys Arg Pro Arg Phe Cys Val Cys Val
1               5                   10

(2) INFORMATION FOR SEQ ID NO:175:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:175:

Lys Leu Cys Tyr Cys Lys Pro Lys Phe Cys Val Cys Val
1               5                   10

(2) INFORMATION FOR SEQ ID NO:176:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:176:

Arg Leu Cys Ala Cys Arg Gly Arg Ala Cys Val Cys Val
1               5                   10

(2) INFORMATION FOR SEQ ID NO:177:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 7...8
        (D) OTHER INFORMATION: Xaa=N-methylglycine (xi) SEQUENCE DESCRIPTION: SEQ ID NO:177:

Arg Leu Cys Tyr Cys Arg Xaa Arg Phe Cys Val Cys Val
1               5                   10

(2) INFORMATION FOR SEQ ID NO:178:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
             (A) NAME/KEY: Other
             (B) LOCATION: 2...3
             (D) OTHER INFORMATION: Xaa=cyclohexylalanine (xi) SEQUENCE DESCRIPTION: SEQ ID NO:178:

Arg Xaa Cys Phe Cys Arg Pro Arg Phe Cys Val Cys Val
1               5                   10

(2) INFORMATION FOR SEQ ID NO:179:

(i) SEQUENCE CHARACTERISTICS:
             (A) LENGTH: 13 amino acids
             (B) TYPE: amino acid
             (C) STRANDEDNESS: unknown
             (D) TOPOLOGY: unknown (ii) MOLECULE TYPE: peptide (xi) SEQUENCE DESCRIPTION: SEQ ID NO:179:

Arg Trp Cys Phe Cys Arg Pro Arg Phe Cys Val Cys Val
1               5                   10

(2) INFORMATION FOR SEQ ID NO:180:

(i) SEQUENCE CHARACTERISTICS:
             (A) LENGTH: 13 amino acids
             (B) TYPE: amino acid
             (C) STRANDEDNESS: unknown
             (D) TOPOLOGY: unknown (ii) MOLECULE TYPE: peptide (xi) SEQUENCE DESCRIPTION: SEQ ID NO:180:

Trp Leu Cys Tyr Cys Arg Arg Arg Phe Cys Val Cys Val
1               5                   10

(2) INFORMATION FOR SEQ ID NO:181:

(i) SEQUENCE CHARACTERISTICS:
             (A) LENGTH: 13 amino acids
             (B) TYPE: amino acid
             (C) STRANDEDNESS: unknown
             (D) TOPOLOGY: unknown (ii) MOLECULE TYPE: peptide (xi) SEQUENCE DESCRIPTION: SEQ ID NO:181:

Trp Leu Cys Phe Cys Arg Arg Arg Phe Cys Val Cys Val
1               5                   10

(2) INFORMATION FOR SEQ ID NO:182:

(i) SEQUENCE CHARACTERISTICS:
             (A) LENGTH: 13 amino acids
             (B) TYPE: amino acid
             (C) STRANDEDNESS: unknown
             (D) TOPOLOGY: unknown (ii) MOLECULE TYPE: peptide (xi) SEQUENCE DESCRIPTION: SEQ ID NO:182:

Phe Leu Cys Phe Cys Arg Arg Arg Phe Cys Val Cys Val
1               5                   10

(2) INFORMATION FOR SEQ ID NO:183:

```
        (i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 9...10
            (D) OTHER INFORMATION: Xaa=N-methylphenylalanine (xi) SEQUENCE DESCRIPTION: SEQ ID NO:183:

Trp Leu Cys Phe Cys Arg Arg Arg Xaa Cys Val Cys Val
 1               5                  10

(2) INFORMATION FOR SEQ ID NO:184:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:184:

Trp Tyr Cys Tyr Cys Arg Arg Arg Phe Cys Val Cys Val
 1               5                  10

(2) INFORMATION FOR SEQ ID NO:185:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 2...3
            (D) OTHER INFORMATION: Xaa=cyclohexylalanine (xi) SEQUENCE DESCRIPTION: SEQ ID NO:185:

Trp Xaa Cys Tyr Cys Arg Arg Arg Phe Cys Val Cys Val
 1               5                  10

(2) INFORMATION FOR SEQ ID NO:186:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 2...3
            (D) OTHER INFORMATION: Xaa=cyclohexylalanine
            (A) NAME/KEY: Other
            (B) LOCATION: 9...10
            (D) OTHER INFORMATION: Xaa=N-methylphenylalanine (xi) SEQUENCE DESCRIPTION: SEQ ID NO:186:

Arg Xaa Cys Phe Cys Arg Gly Arg Xaa Cys Val Cys Val
 1               5                  10
```

(2) INFORMATION FOR SEQ ID NO:187:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 1...2
        (D) OTHER INFORMATION: Xaa=cyclohexylalanine
        (A) NAME/KEY: Other
        (B) LOCATION: 9...10
        (D) OTHER INFORMATION: Xaa=N-methylphenylalanine (xi) SEQUENCE DESCRIPTION: SEQ ID NO:187:

```
Xaa Leu Cys Phe Cys Arg Arg Arg Xaa Cys Val Cys Val
 1               5                  10
```

(2) INFORMATION FOR SEQ ID NO:188:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:188:

```
Arg Leu Cys Tyr Cys Arg Pro Arg Phe Cys Val Cys Val Gly Arg
 1               5                  10                  15
```

(2) INFORMATION FOR SEQ ID NO:189:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:189:

```
Trp Leu Cys Tyr Cys Arg Arg Arg Phe Cys Val Cys Val Gly Arg
 1               5                  10                  15
```

(2) INFORMATION FOR SEQ ID NO:190:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 2...3
        (D) OTHER INFORMATION: Xaa=cyclohexylalanine (xi) SEQUENCE DESCRIPTION: SEQ ID NO:190:

```
Trp Xaa Cys Tyr Cys Arg Arg Arg Phe Cys Val Cys Val Gly Arg
 1               5                  10                  15
```

(2) INFORMATION FOR SEQ ID NO:191:

(i) SEQUENCE CHARACTERISTICS:

(A) LENGTH: 13 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:191:

Arg Leu Cys Tyr Cys Arg Gly Pro Phe Cys Val Cys Arg
1               5                   10

(2) INFORMATION FOR SEQ ID NO:192:

(i) SEQUENCE CHARACTERISTICS:
            (A) LENGTH: 16 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:192:

Arg Arg Trp Cys Phe Val Cys Tyr Ala Gly Phe Cys Tyr Arg Cys Arg
1               5                   10                  15

(2) INFORMATION FOR SEQ ID NO:193:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:193:

Arg Arg Cys Tyr Cys Arg Gly Arg Phe Cys Gly Cys Val Gly Arg
1               5                   10                  15

(2) INFORMATION FOR SEQ ID NO:194:

(i) SEQUENCE CHARACTERISTICS:
            (A) LENGTH: 16 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:194:

Arg Trp Arg Cys Tyr Cys Gly Arg Arg Phe Cys Gly Cys Val Gly Arg
1               5                   10                  15

(2) INFORMATION FOR SEQ ID NO:195:

(i) SEQUENCE CHARACTERISTICS:
            (A) LENGTH: 16 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:195:

Arg Ala Arg Cys Tyr Cys Gly Arg Arg Phe Cys Gly Cys Val Gly Arg
1               5                   10                  15

(2) INFORMATION FOR SEQ ID NO:196:

(i) SEQUENCE CHARACTERISTICS:

(A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:196:

Gly Trp Arg Cys Tyr Cys Arg Gly Arg Phe Cys Gly Cys
1               5                   10

(2) INFORMATION FOR SEQ ID NO:197:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:197:

Arg Gly Trp Ala Cys Tyr Cys Arg Gly Arg Phe Cys Val Cys
1               5                   10

(2) INFORMATION FOR SEQ ID NO:198:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:198:

Arg Arg Cys Tyr Gly Arg Arg Arg Phe Gly Val Cys Val Gly Arg
1               5                   10                  15

(2) INFORMATION FOR SEQ ID NO:199:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:199:

Arg Gly Trp Arg Leu Cys Tyr Gly Arg Gly Arg Phe Lys Val Cys
1               5                   10                  15

(2) INFORMATION FOR SEQ ID NO:200:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:200:

Arg Gly Trp Arg Leu Cys Tyr Cys Arg Gly Arg Phe Cys Val Cys
1               5                   10                  15

(2) INFORMATION FOR SEQ ID NO:201:

(i) SEQUENCE CHARACTERISTICS:

(A) LENGTH: 11 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:201:

Cys Tyr Cys Arg Arg Arg Phe Cys Val Cys Phe
1               5                   10

(2) INFORMATION FOR SEQ ID NO:202:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 10...11
            (D) OTHER INFORMATION: Xaa=N-methyglycine (xi) SEQUENCE DESCRIPTION: SEQ ID NO:202:

Arg Gly Trp Arg Leu Cys Tyr Cys Arg Xaa Arg Phe Cys Val Cys
1               5                   10                  15

(2) INFORMATION FOR SEQ ID NO:203:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 10...11
            (D) OTHER INFORMATION: Xaa=N-methylglycine or sa
                rcosine (xi) SEQUENCE DESCRIPTION: SEQ ID NO:203:

Arg Gly Trp Arg Gly Cys Tyr Cys Arg Xaa Arg Phe Cys Gly Cys
1               5                   10                  15

(2) INFORMATION FOR SEQ ID NO:204:

(i) SEQUENCE CHARACTERISTICS:
            (A) LENGTH: 14 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:204:

Leu Cys Tyr Cys Arg Pro Arg Phe Cys Val Cys Val Gly Arg
1               5                   10

(2) INFORMATION FOR SEQ ID NO:205:

(i) SEQUENCE CHARACTERISTICS:
            (A) LENGTH: 14 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:205:

Leu Cys Tyr Cys Lys Pro Lys Phe Cys Val Cys Val Gly Lys
 1               5                  10

(2) INFORMATION FOR SEQ ID NO:206:

(i) SEQUENCE CHARACTERISTICS:
         (A) LENGTH: 14 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:206:

Leu Cys Tyr Cys Arg Gly Arg Phe Cys Val Cys Val Gly Arg
 1               5                  10

(2) INFORMATION FOR SEQ ID NO:207:

(i) SEQUENCE CHARACTERISTICS:
         (A) LENGTH: 16 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:207:

Leu Cys Tyr Cys Arg Pro Arg Phe Cys Val Cys Val Gly Arg Gly Arg
 1               5                  10                  15

(2) INFORMATION FOR SEQ ID NO:208:

(i) SEQUENCE CHARACTERISTICS:
         (A) LENGTH: 15 amino acids
         (B) TYPE: amino acid
         (C) STRANDEDNESS: unknown
         (D) TOPOLOGY: unknown (ii) MOLECULE TYPE: peptide (v) FRAGMENT TYPE: internal (xi) SEQUENCE DESCRIPTION: SEQ ID NO:208:

Arg Arg Trp Cys Tyr Cys Arg Pro Arg Phe Cys Val Cys Val Arg
 1               5                  10                  15

(2) INFORMATION FOR SEQ ID NO:209:

(i) SEQUENCE CHARACTERISTICS:
         (A) LENGTH: 16 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:209:

Trp Arg Leu Cys Tyr Cys Arg Pro Arg Phe Cys Val Cys Val Gly Arg
 1               5                  10                  15

(2) INFORMATION FOR SEQ ID NO:210:

(i) SEQUENCE CHARACTERISTICS:
         (A) LENGTH: 16 amino acids
         (B) TYPE: amino acid
         (C) STRANDEDNESS: unknown (D) TOPOLOGY: unknown (ii) MOLECULE TYPE: peptide (xi) SEQUENCE DESCRIPTION: SEQ ID NO:210:

Gly Trp Leu Cys Tyr Cys Arg Gly Arg Phe Cys Val Cys Val Gly Arg
1               5                   10                  15

(2) INFORMATION FOR SEQ ID NO:211:

(i) SEQUENCE CHARACTERISTICS:
            (A) LENGTH: 16 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:211:

Arg Trp Leu Cys Tyr Cys Arg Gly Arg Phe Cys Val Cys Val Gly Arg
1               5                   10                  15

(2) INFORMATION FOR SEQ ID NO:212:

(i) SEQUENCE CHARACTERISTICS:
            (A) LENGTH: 16 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:212:

Arg Leu Leu Cys Tyr Cys Arg Gly Arg Phe Cys Val Cys Val Gly Arg
1               5                   10                  15

(2) INFORMATION FOR SEQ ID NO:213:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:213:

Arg Trp Arg Leu Cys Tyr Cys Arg Pro Arg Phe Cys Val Cys Val
1               5                   10                  15

(2) INFORMATION FOR SEQ ID NO:214:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 2...3
            (D) OTHER INFORMATION: Xaa=cyclohexylalanine
            (A) NAME/KEY: Other
            (B) LOCATION: 9...10
            (D) OTHER INFORMATION: Xaa=N-methylglycine (xi) SEQUENCE DESCRIPTION: SEQ ID NO:214:

Arg Xaa Arg Leu Cys Tyr Cys Arg Xaa Arg Phe Cys Val Cys Val
1               5                   10                  15

(2) INFORMATION FOR SEQ ID NO:215:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 12...13
        (D) OTHER INFORMATION: Xaa=cyclohexylalanine (xi) SEQUENCE DESCRIPTION: SEQ ID NO:215:

```
Arg Gly Trp Arg Leu Cys Tyr Cys Arg Gly Arg Xaa Cys Val Cys Val
1               5                   10                  15
```

(2) INFORMATION FOR SEQ ID NO:216:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:216:

```
Arg Gly Gly Arg Val Cys Tyr Cys Arg Gly Arg Phe Cys Val Cys Val
1               5                   10                  15
```

(2) INFORMATION FOR SEQ ID NO:217:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:217:

```
Leu Cys Tyr Cys Arg Xaa Arg Phe Cys Val Cys Val
1               5                   10
```

(2) INFORMATION FOR SEQ ID NO:218:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:218:

```
Leu Cys Tyr Cys Lys Pro Lys Phe Cys Val Cys Val
1               5                   10
```

(2) INFORMATION FOR SEQ ID NO:219:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:219:

Val Cys Tyr Cys Arg Pro Arg Phe Cys Val Cys Val
1               5                   10

(2) INFORMATION FOR SEQ ID NO:220:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:220:

Leu Cys Tyr Cys Arg Pro Arg Phe Cys Val Cys Trp
1               5                   10

(2) INFORMATION FOR SEQ ID NO:221:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:221:

Leu Cys Tyr Arg Arg Pro Arg Phe Arg Val Cys Val
1               5                   10

(2) INFORMATION FOR SEQ ID NO:222:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 11...12
        (D) OTHER INFORMATION: Xaa=cyclohexylalanine (xi) SEQUENCE DESCRIPTION: SEQ ID NO:222:

Arg Gly Trp Arg Leu Cys Tyr Cys Arg Gly Xaa Cys Val Cys Val
1               5                   10                  15

(2) INFORMATION FOR SEQ ID NO:223:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 2...3
        (D) OTHER INFORMATION: Xaa=cyclohexylalanine
        (A) NAME/KEY: Other
        (B) LOCATION: 9...10
        (D) OTHER INFORMATION: Xaa=N-methylglycine (xi) SEQUENCE DESCRIPTION: SEQ ID NO:223:

Arg Xaa Arg Leu Cys Tyr Cys Arg Xaa Arg Phe Cys Val Cys Val
1               5                   10                  15

(2) INFORMATION FOR SEQ ID NO:224:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 2...3
        (D) OTHER INFORMATION: Xaa=cyclohexylalanine (xi) SEQUENCE DESCRIPTION: SEQ ID NO:224:

Arg Xaa Arg Leu Cys Tyr Cys Arg Gly Arg Phe Cys Val Cys Val
1               5                   10                  15

(2) INFORMATION FOR SEQ ID NO:225:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:225:

Arg Gly Gly Gly Leu Cys Tyr Ala Arg Gly Trp Ile Ala Phe Cys Val
1               5                   10                  15

Gly Arg (2) INFORMATION FOR SEQ ID NO:226:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:226:

Arg Gly Gly Gly Leu Cys Tyr Ala Arg Gly Phe Ile Ala Val Cys Phe
1               5                   10                  15

Gly Arg (2) INFORMATION FOR SEQ ID NO:227:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:227:

Arg Gly Gly Gly Leu Cys Tyr Ala Arg Pro Arg Phe Ala Val Cys Val
1               5                   10                  15

Gly Arg (2) INFORMATION FOR SEQ ID NO:228:

(i) SEQUENCE CHARACTERISTICS:
    (A) LENGTH: 18 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:228:

```
Arg Gly Gly Gly Leu Cys Tyr Thr Arg Pro Arg Phe Thr Val Cys Val
1               5                   10                  15
Gly Arg
```

(2) INFORMATION FOR SEQ ID NO:229:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:229:

```
Arg Gly Gly Gly Leu Cys Tyr Ala Arg Lys Gly Phe Ala Val Cys Val
1               5                   10                  15
Gly Arg
```

(2) INFORMATION FOR SEQ ID NO:230:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:230:

```
Arg Gly Gly Arg Leu Cys Tyr Ala Arg Arg Arg Phe Ala Val Cys Val
1               5                   10                  15
Gly Arg
```

(2) INFORMATION FOR SEQ ID NO:231:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:231:

```
Arg Gly Gly Gly Leu Cys Tyr Lys Arg Gly Phe Ile Lys Val Cys Phe
1               5                   10                  15
Gly Arg
```

(2) INFORMATION FOR SEQ ID NO:232:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:232:

Arg Gly Gly Gly Leu Cys Tyr Lys Arg Gly Trp Ile Lys Phe Cys Val
1               5                   10                  15

Gly Arg (2) INFORMATION FOR SEQ ID NO:233:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:233:

Arg Gly Gly Gly Leu Cys Tyr Arg Leu Pro Lys Phe Arg Val Cys Val
1               5                   10                  15

Gly Arg (2) INFORMATION FOR SEQ ID NO:234:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:234:

Arg Gly Gly Gly Leu Cys Tyr Arg Leu Pro Gly Phe Arg Val Cys Val
1               5                   10                  15

Gly Arg (2) INFORMATION FOR SEQ ID NO:235:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:235:

Arg Gly Trp Arg Gly Cys Tyr Lys Arg Gly Arg Phe Lys Gly Cys Val
1               5                   10                  15

Gly Arg (2) INFORMATION FOR SEQ ID NO:236:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:236:

Leu Cys Tyr Lys Arg Gly Arg Phe Lys Val Cys Val
1               5                   10

(2) INFORMATION FOR SEQ ID NO:237:

(i) SEQUENCE CHARACTISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:237:

Ile Cys Tyr Arg Pro Arg Phe Val Cys Val Gly Arg
1               5                   10

(2) INFORMATION FOR SEQ ID NO:238:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:238:

Trp Leu Cys Tyr Cys Arg Arg Arg Phe Cys Val Cys Val
1               5                   10

(2) INFORMATION FOR SEQ ID NO:239:

(i) SEQUENCE CHARACTERISTICS:

(xi) SEQUENCE DESCRIPTION: SEQ ID NO:239:

This sequence has been intentionally skipped (2) INFORMATION FOR SEQ ID NO:240:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:240:

Arg Leu Cys Tyr Cys Arg Arg Arg Phe Cys Val Cys Val
1               5                   10

(2) INFORMATION FOR SEQ ID NO:241:

(i) SEQUENCE CHARACTERISTICS:
            (A) LENGTH: 20 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:241:

Arg Gly Arg Val Cys Leu Arg Tyr Cys Arg Gly Arg Phe Cys Val Arg
1               5                   10                  15
Leu Cys Phe Arg
            20

(2) INFORMATION FOR SEQ ID NO:242:

(i) SEQUENCE CHARACTERISTICS:
            (A) LENGTH: 17 amino acids
            (B) TYPE: amino acid (C) STRANDEDNESS: unknown
(D) TOPOLOGY: unknown (ii) MOLECULE TYPE: peptide (xi) SEQUENCE DESCRIPTION: SEQ ID NO:242:

Arg Arg Arg Leu Cys Tyr Cys Arg Arg Arg Phe Cys Val Cys Val Gly
1               5                   10                  15
Arg